(12) United States Patent
Richardson et al.

(10) Patent No.: US 8,841,120 B2
(45) Date of Patent: Sep. 23, 2014

(54) VIRUS-LIKE PARTICLES COMPRISING COMPOSITE CAPSID AMINO ACID SEQUENCES FOR ENHANCED CROSS REACTIVITY

(75) Inventors: Charles Richardson, Bozeman, MT (US); Robert F. Bargatze, Bozeman, MT (US); Joel Haynes, Bozeman, MT (US); Bryan Steadman, Bozeman, MT (US)

(73) Assignee: Takeda Vaccines, Inc., Bozeman, MT (US)

( * ) Notice: Subject to any disclaimer, the term of this patent is extended or adjusted under 35 U.S.C. 154(b) by 196 days.

(21) Appl. No.: 13/023,363

(22) Filed: Feb. 8, 2011

(65) Prior Publication Data

US 2011/0195113 A1    Aug. 11, 2011

Related U.S. Application Data

(63) Continuation-in-part of application No. PCT/US2009/053249, filed on Aug. 10, 2009.

(60) Provisional application No. 61/087,504, filed on Aug. 8, 2008, provisional application No. 61/218,603, filed on Jun. 19, 2009.

(51) Int. Cl.
| | |
|---|---|
| *C12N 15/40* | (2006.01) |
| *C07K 14/005* | (2006.01) |
| *A61K 39/12* | (2006.01) |
| *C12N 13/00* | (2006.01) |
| *A61K 39/00* | (2006.01) |

(52) U.S. Cl.
CPC ........ *A61K 39/12* (2013.01); *C12N 2770/16022* (2013.01); *C12N 2770/16023* (2013.01); *A61K 2039/5258* (2013.01); *C07K 14/005* (2013.01); *C12N 2770/16034* (2013.01)
USPC .................................... 435/320.1; 435/91.21

(58) Field of Classification Search
None
See application file for complete search history.

(56) References Cited

U.S. PATENT DOCUMENTS

| | | | |
|---|---|---|---|
| 5,645,051 A | 7/1997 | Schultz et al. | |
| 5,861,241 A | 1/1999 | Herrmann et al. | |
| 5,953,727 A | 9/1999 | Maslyn et al. | |
| 6,391,318 B1 | 5/2002 | Illum et al. | |
| 6,491,919 B2 | 12/2002 | Crane | |
| 6,572,862 B1 | 6/2003 | Estes et al. | |
| 6,602,697 B1 | 8/2003 | Cook, III | |
| 6,942,865 B2 | 9/2005 | Estes et al. | |
| 7,067,638 B1 | 6/2006 | Takeda et al. | |
| 7,481,997 B1 * | 1/2009 | Hardy | 424/93.1 |
| 7,527,801 B2 * | 5/2009 | Coit et al. | 424/216.1 |
| 7,955,603 B2 * | 6/2011 | Richardson et al. | 424/204.1 |
| 8,119,145 B2 * | 2/2012 | Coit et al. | 424/216.1 |
| 8,124,104 B2 * | 2/2012 | Coit et al. | 424/216.1 |
| 8,142,793 B2 * | 3/2012 | Coit et al. | 424/216.1 |
| 8,431,116 B2 | 4/2013 | Richardson et al. | |
| 2004/0063188 A1 | 4/2004 | Robinson et al. | |
| 2004/0265377 A1 | 12/2004 | Seager | |
| 2005/0154053 A1 | 7/2005 | Rhijn et al. | |
| 2005/0155113 A1 | 7/2005 | Hamilton et al. | |
| 2005/0215501 A1 | 9/2005 | Lipford et al. | |
| 2005/0260225 A1 | 11/2005 | Goldberg et al. | |
| 2007/0207526 A1 | 9/2007 | Coit et al. | |
| 2008/0299152 A1 | 12/2008 | Richardson et al. | |
| 2010/0266636 A1 | 10/2010 | Richardson et al. | |
| 2011/0182975 A1 | 7/2011 | Richardson et al. | |
| 2012/0093861 A1 | 4/2012 | Richardson et al. | |
| 2012/0156243 A1 | 6/2012 | Richardson et al. | |

FOREIGN PATENT DOCUMENTS

| | | |
|---|---|---|
| EP | 1186890 A1 | 3/2002 |
| EP | 2360175 A2 | 8/2011 |
| JP | H10500847 | 1/1998 |
| WO | WO 92/16543 A1 | 10/1992 |
| WO | WO 93/21325 A1 | 10/1993 |
| WO | WO 2005/060966 A1 | 7/2005 |
| WO | WO 2006/044857 A2 | 4/2006 |
| WO | WO 2006/067632 A2 | 6/2006 |
| WO | WO 2006/086188 A2 | 8/2006 |
| WO | WO 2006/091517 A2 | 8/2006 |
| WO | WO 2006/097530 A2 | 9/2006 |
| WO | WO 2006/136566 A1 | 12/2006 |
| WO | WO 2007/081447 A2 | 7/2007 |
| WO | WO 2008/042789 A1 | 4/2008 |
| WO | WO 2009/039229 A2 | 3/2009 |
| WO | WO 2010/017542 A1 | 2/2010 |

OTHER PUBLICATIONS

Nicollier-Jamot et al., "Recombinant virus-like particles of a norovirus (genogroup II strain) administered intranasally and orally with mucosal adjuvants LT and LT(R192G) in BALB/c mice induce specific humoral and cellular Th1/Th2-like immune responses," Vaccine, vol. 22: 1079-1086, 2004.

Lobue et al., "Multivalent norovirus vaccines induce strong mucosal and systemic blocking antibodies against multiple strains," Vaccine, vol. 24: 5220-5324, 2006.

(Continued)

*Primary Examiner* — Bao Li
(74) *Attorney, Agent, or Firm* — Cooley LLP

(57) ABSTRACT

The present invention provides polypeptides having a composite amino acid sequence derived from a consensus sequence representing the capsid proteins of two or more circulating strains of a non-enveloped virus. In particular, the invention provides virus-like particles comprising at least one composite polypeptide. Such virus-like particles have antigenic epitopes of two or more circulating strains of a non-enveloped virus and produce an increase in antisera cross-reactivity to one or more circulating strains of the non-enveloped virus. Methods of making composite virus-like particles and vaccine formulations comprising composite virus-like particles are also disclosed.

35 Claims, 22 Drawing Sheets

(56) References Cited

OTHER PUBLICATIONS

Tacket, C. O. et al., "Humoral, mucosal, and cellular immune responses to oral Norwalk virus-like particles in volunteers," Clinical immunology, vol. 108: 241-247, 2003.
Guerrero, R. A. et al., "Recombinant Norwalk Virus-Like Particles Administered Intranasally to Mice Induce Systemic and Mucosal (Fecal and Vaginal) Immune Responses," Journal of Virology, vol. 75: 9713-9722, 2001.
Ball, J. M. et al., "Oral Immunization with Recombinant Norwalk Virus-Like Particles Induces a Systemic and Mucosal Immune Response in Mice," Journal of Virology, vol. 72:1345-1353, 1998.
Allen et al., "Analysis of Amino Acid Variation in the P2 Domain of the GII-4 Norovirus VP1 Protein Reveals Putative Variant-Specific Epitopes," PLOS One, vol. 3: e1485, 2008.
Siebenga et al., "Epochal Evolution of GGII.4 Norovirus Capsid Proteins from 1995 to 2006," Journal of Virology, vol. 81: 9932-9941, 2007.
Lindesmith et al., "Mechanisms of GII.4 Norovirus Persistence in Human Populations," PLOS One, vol. 5: e31, 2008.
Fankhauser et al., "Molecular Epidemiology of "Norwalk-like Viruses" in Outbreaks of Gastroenteritis in the United States," The Journal of Infectious Diseases, vol. 178: 1571-1578, 1998.
Hansman et al., "Genetic and antigenic diversity among noroviruses," Journal of General Virology. vol. 87: 909-919, 2006.
Bull et al., "Emergence of a New Norovirus Genotype II.4 Variant Associated with Global Outbreaks of Gastroenteritis," Journal of Clinical Microbiology, vol. 44: 327-333, 2006.
Herbst-Kralovetz et al., "Norwalk virus-like particles as vaccines," Expert Rev. Vaccines 9(3), 299-307, 2010.
Ando et al., "Genetic Classification of 'Norwalk-like Viruses,'" The Journal of Infectious Diseases, vol. 181(Suppl 2): S336-S348, 2000.
Lindell et al., "Molecular Epidemiology of Norovirus Infections in Stockholm, Sweden, during the Years 2000 to 2003: Association of the GGIIb Genetic Cluster with Infection in Children," Journal of Clinical Microbiology, vol. 43: 1086-1092, 2005.
Young, International Search Report and Written Opinion of International Search Authority for international application No. PCT/US2007/079929 mailed Mar. 11, 2008.
Park, International Search Report and Written Opinion of International Search Authority for international application No. PCT/US2008/076763 mailed Jul. 15, 2009.
Young, International Search Report and Written Opinion of International Search Authority for international application No. PCT/US2009/053249 mailed Dec. 14, 2009.
Angioni, C.F., "Supplementary European Search Report," 9 pages, from European Patent Appl. No. 07853688.5, European Patent Office, The Hague, Netherlands (mailed Sep. 22, 2010).
Ausar et al., "Conformational stability and disassembly of norwalk virus like particles: effect of pH and temperature,"J. Biol. Chem., vol. 281: 19478-19488, 2006.
Baldrick et al., Safety evaluation of monophosphoryl lipid A (MPL): an immunostimulatory adjuvant. Regulatory Toxicology and Pharmacology 2002; vol. 35:398-413.
Baldridge et al., Monophosphoryl lipid A enhances mucosal and systemic immunity to vaccine antigens following intranasal administration. Vaccine 2000; vol. 18:2416-2425.
Ball et al., Recombinant Norwalk virus-like particles given orally to volunteers: phase I study. Gastroenterology 1999; vol. 117:40-48.
Baric et al., "Expression and Self-Assembly of Norwalk Virus Capsid Protein from Venezuelan Equine Encephalitis Virus Replicons," J. Virol. 76(6):3023-3030 (2002).
Bertolotti-Ciarlet et al., "Structural Requirements for the Assembly of Norwalk Virus-Like Particles," J. Virol. 76(8):4044-4055 (2002).
Cachia et al., "The use of synthetic peptides in the design of a consensus sequence vaccine for Pseudomonas aeruginosa," J. Pept. Res. 52(4):289-299 (1998).
Cao et al., "Structural Basis for the Recognition of Blood Group Trisaccharides by Norovirus," J. Virol. 81(11):5949-5957 (2007).
Carpenter et al., Rational design of stable lyophilized protein formulations: some practical advice, Pharmaceutical Research, vol. 14: 969-975, 1997.
Cheetham et al., "Binding patterns of human norovirus-like particles to buccal and intestinal tissues of gnotobiotic pigs in relation to A/H histo-blood group antigen expression," Journal of Virology, vol. 81: 3535-3544, 2007.
Chen et al., "X-ray structure of a native calicivirus: Structural insights into antigenic diversity and host specificity," Proc. Natl Acad. Sci. USA 103(21):8048-8053 (2006).
Childers et al., "Adjuvant activity of monophosphoryl lipid A for nasal and oral immunization with soluble or liposome-associated antigen," Infection and Immunity, vol. 68: 5509-5516, 2000.
Davis and Illum, Absorption enhancers for nasal drug delivery. Clinical Pharmacokinetics 2003; vol. 42:1107-1128.
Estes et al., Norwalk Virus Vaccines: Challenges and Progress. The Journal of Infectious Disease 2000; vol. 181(Suppl 2): S367-373.
Foubert et al., "Preclinical Development of a Broad Spectrum Norovirus Vaccine," AAPS National Biotechnology Conference, http://abstracts.aapspharmaceutica.com/ExpoNBC09/CC/forms/attendee/index.aspx?content=sessionInfo&sessionId=150 (2009).
Gray et al., Detection of immunoglobulin M (IgM), IgA, and IgG Norwalk virus-specific antibodies by indirect enzyme-linked immunosorbent assay with baculovirus-expressed Norwalk virus capsid antigen in adult volunteers challenged with Norwalk virus. Journal of Clinical Microbiology 1994; vol. 32:3059-3063.
Han et al., Immune responses to bovine norovirus-like particles with various adjuvants and analysis of protection in gnotobiotic calves. Vaccine 2006; vol. 24:317-326.
Han et al., "Thermosensitive and mucoadhesive delivery systems of mucosal vaccines," Methods, vol. 38:106-111, 2006.
Harrington et al., "Systemic, Mucosal, and Heterotypic Immune Induction in Mice Inoculated with Venezuelan Equine Encephalitis Replicons Expressing Norwalk Virus-Like Particles," J. Virol. 76(2):730-742 (2002).
Huang et al., "Noroviruses Bind to Human ABO, Lewis, and Secretor Histo-Blood Group Antigens: Identification of 4 Distinct Strain-Specific Patterns," J. Infect. Dis. 188(1):19-31 (2003).
Hutson et al., Norovirus disease: changing epidemiology and host susceptibility factors. TRENDS in Microbiology 2004; vol. 12(6):279-287.
Hutson et al., "Norwalk Virus-Like Particle Hemagglutination by Binding to H Histo-Blood Group Antigens," J. Virol. 77(1):405-415 (2003).
Illum et al., Chitosan as a novel nasal delivery system for peptide drugs. Pharmaceutical Research 1994.; vol. 11:1186-1189.
Illum et al., Chitosan as a novel nasal delivery system for vaccines. Advanced Drug Delivery Reviews 2001; vol. 51:81-96.
Illum et al., Nasal drug delivery—possibilities, problems and solutions. Journal of Controlled Release 2003; vol. 87:187-198.
International Search Report, 3 pages, PCT appl. No. PCT/US2012/046222 (mailed Oct. 2, 2012).
Jaimes et al., "Maturation and Trafficking Markers on Rotavirus-Specific B Cells during Acute Infection and Convalescence in Children," J. Virol 78:10967-10976 (2004).
Jiang et al., "Expression, Self-Assembly, and Antigenicity of the Norwalk Virus Capsid Protein," J. Virol. 66(11):6527-6532 (1992).
Jiang et al., "Norwalk virus genome cloning and characterization," Science 250:1580-1583 (1990).
Johnson et al., Multiple Challenge Study of Host Susceptibility to Norwalk Gastroenteritis in U.S. Adults. The Journal of Infectious Disease 1990; vol. 161: 18-21.
Kamata et al., "Increased Frequency of Surface IgA-Positive Plasma Cells in the Intestinal Lamina Propia and Decreased IgA Excretion in Hyper IgA (HIGA) Mice, a Murine Model of IgA Nephropathy with Hyperserum IgA," J. Immunol. 165:1387-1394 (2000).
Ligocyte Pharmaceuticals, "Ligocyte Pharmaceuticals initiates U.S. clinical trial of norovirus vaccine," http://www.ligocyte.com/news/documents/LIGOCYTE-pharmaceuticals-4-3-2007.pdf, Apr. 3, 2007, 2 pages.
Lindesmith et al., Cellular and humoral immunity following Snow Mountain virus challenge. Journal of Virology 2005; vol. 79(5): 2900-2909.

(56) References Cited

OTHER PUBLICATIONS

Lindesmith et al., Human susceptibility and resistance to Norwalk infection. Nature Medicine 2003; vol. 9(5): 548-553.

Lobue et al., "Alphavirus adjuvanted norovirus-like particle vaccines: heterologous, humoral, and mucosal immune responses protect against murine norovirus challenge," J. Virol., vol. 83(7): 3212-3227, 2009.

Malcolmson and Embleton, "Dry powder formulations for pulmonary delivery," Pharmaceutical Science and Technology Today, vol. 1:394-398, 1998.

Mason et al., "Expression of Norwalk virus capsid protein in transgenic tobacco and potato and its oral immunogenicity in mice," Proc. Natl Acad. Sci. USA 93(11):5335-5340 (1996).

Matsui et al., Immunity to Calicivirus infection. The Journal of Infectious Diseases 2000; vol. 181(S2): S331-335.

McBurney et al., "Developing Broadly Reactive HIV-1/AIDS Vaccines: A Review of Polyvalent and Centralized HIV-1 Vaccines," Curr. Pharm. Design 13(19):1957-1964 (2007).

Mead et al., Food Related Illness and Death in the U.S., Emerging Infectious Diseases 1999; vol. 5(5): 607-635.

Muthumani et al., "Immunogenicity of novel consensus-based DNA vaccines against Chikungunya virus," Vaccine 26(40):5128-5134 (2008).

Noel et al., Correlation of patient immune responses with genetically characterized small round-structured viruses involved in outbreaks of nonbacterial acute gastroenteritis in the United States, 1990 to 1995. Journal of Medical Virology 1997; vol. 53:372-383.

O'Hagan et al., "Recent developments in adjuvants for vaccines against infectious diseases," Biomol. Eng. 18(3):69-85 (2001).

Parrino et al., Clinical immunity in acute gastroenteritis caused by Norwalk agent. New England Journal of Medicine 1977; vol. 297:86-89.

Partial European Searcht Report, 7 pages, EP appl. No. 13157572.2 (Apr. 5, 2013).

Pelosi et al., "The Seroepidemiology of Genogroup 1 and Genogroup 2 Norwalk-Like Viruses in Italy," J. Med. Virol. 58:93-99 (1999).

Periwal et al., A Modified Cholera Holotoxin CT-E29H Enhances Systemic and Mucosal Immune Responses to Recombinant Norwalk Virus-like Particle Vaccine. Vaccine 2003; vol. 21:376-385.

Prasad et al., "Structural studies of recombinant norwalk capsids," J. Infect. Dis., vol. 181(s2), S317-S321, 2000.

Rasmussen et al., "In Multiple Myeloma Clonotypic $CD38^-/CD19^+/CD27^+$ Memory B Cells Recirculate Through Bone Marrow, Peripheral Blood and Lymph Nodes," Leuk. Lymph. 45(7):1413-1417 (2004).

Richardson et al., "Norovirus Vaccine Formulations," U.S. Appl. No. 12/816,495, filed Jun. 16, 2010.

Sha et al., "Activation of Airway Epithelial Cells by Toll-Like Receptor Agonists," Am. J. Respir. Cell Mol. Biol. 31(3):358-364 (2004).

Singh et al., "A preliminary evaluation of alternative adjuvants to alum using a range of established and new generation vaccine antigens," Vaccine 24(10):1680-1686 (2006).

Souza et al., "A human norovirus-like particle adjuvanted with ISCOM or mLT induces cytokine and antibody responses and protection to the homologous GII.4 human norovirus in a gnotobiotic pig disease model," Vaccine, vol. 25: 8448-8459, 2007.

Supplementary European Search Report, 13 pages, EP appl. No. 08832560.0 (Apr. 5, 2012).

Supplementary European Search Report, 8 pages, EP appl. No. 09805653.4 (Dec. 2, 2011).

Tacket et al., "Human immune responses to a novel norwalk virus vaccine delivered in transgenic potatoes.," J. Infect. Dis., vol. 182(1): 302-305, 2000.

Ugwoke et al., "Nasal mucoadhesive drug delivery: Background, applications, trends and future perspectives," Advanced Drug Delivery Reviews, vol. 57: 1640-1665, 2005.

Wang et al., "Effective synthetic peptide vaccine for foot-and-mouth disease in swine," Vaccine 20(19-20):2603-2610 (2002).

Written Opinion of the International Searching Authority, 6 pages, PCT appl. No. PCT/US2012/046222 (Oct. 2, 2012).

Wyatt et al., Comparison of three agents of acute infectious nonbacterial gastroenteritis by cross-challenge in volunteers. Journal of Infecious. Diseases 1974.; vol. 129:709-714.

Xia et al., "Norovirus Capsid Protein Expressed in Yeast Forms Virus-like Particles and Stimulates Systemic and Mucosal Immunity in Mice Following an Oral Administration of Raw Yeat Extracts," J. Med Virol. 79:74-83 (2007).

Lew, J.F. et al. "Molecular Characterization and Expression of the Capsid Protein of a Norwalk-like Virus Recovered from a Desert Stroop withi Gastroenteritis." *Virology* 200; 319-325 (1994).

\* cited by examiner

FIGURE 1

MKMAS-$X_1$-DA-$X_2$-PSDGS-$X_3$-ANLVPEVNNEVMALEPVVGAAIAAPVAGQQNVIDPWIRNNFVQAPGG
EFTVSPRNAPGEILWSAPLGPDLNPYLSHLARMYNGYAGGFEVQVILAGNAFTAGKIIFAAVPPNFPTEG
LSPSQVTMFPHIIVDVRQLEPVLIPLPDVRNNFYHYNQSND-$X_4$-TIKLIAMLYTPLRANNAG-$X_5$-DVFT
VSCRVLTRPSPDFDFIFLVPPTVESRTKPF-$X_6$-VPILTVEEMTNSRFPIPLEKLFTGPS-$X_7$-AFVVQPQ
NGRCTTDGVLLGTTQLSPVNICTFRGDVTHIAG-$X_8$-$X_9$-$X_{10}$-YTMNLAS-$X_{11}$-NWNNYDPTEEIPAPLGT
PDFVGKIQGVLTQTT-$X_{12}$-$X_{13}$-DGSTRGHKATV-$X_{14}$-TGS-$X_{15}$-$X_{16}$-FTPKLG-$X_{17}$-$X_{18}$-QF-$X_{19}$-TD
T-$X_{20}$-ND-$X_{21}$-ET-$X_{22}$-QNT-$X_{23}$-FTPVGV-$X_{24}$-QDG-$X_{25}$-$X_{26}$-$X_{27}$-H-$X_{28}$-NEPQQWVLP-$X_{29}$-YSG
R-$X_{30}$-$X_{31}$-HNVHLAPAVAP-$X_{32}$-FPGEQLLFFRSTMPGCSGYPNM-$X_{33}$-LDCLLPQEWV-$X_{34}$-HFYQEA
APAQSDVALLRFVNPDTGRVLFECKLHKSGYVTVAHTG-$X_{35}$-HDLVIPPNGYFRFDSWVNQFYTLAPMGN
G-$X_{36}$-GRRRA, wherein $X_1$ = S or N; $X_2$ = S or N; $X_3$ = T or A; $X_4$ = S or P; $X_5$ = D or E; $X_6$ = S or T; $X_7$ = G or S; $X_8$ = S or T; $X_9$ = Q, R, or H; $X_{10}$ = E, D, or N; $X_{11}$ = Q or L; $X_{12}$ = R or K; $X_{13}$ = G or R; $X_{14}$ = S or Y; $X_{15}$ = V or A; $X_{16}$ = P or H; $X_{17}$ = S or R; $X_{18}$ = V or I; $X_{19}$ = S or T; $X_{20}$ = S, E, or N; $X_{21}$ = F or L; $X_{22}$ = G or H; $X_{23}$ = R or K; $X_{24}$ = V or I; $X_{25}$ = S or N; $X_{26}$ = S or T; $X_{27}$ = A or T; $X_{28}$ = Q or R; $X_{29}$ = D, S, or N; $X_{30}$ = D, N, or T; $X_{31}$ = S, V, or G; $X_{32}$ = S or T; $X_{33}$ = N or D; $X_{34}$ = Q or L; $X_{35}$ = Q or P; and $X_{36}$ = T or A. (SEQ ID NO: 2)

FIGURE 2

```
TTAATTAAGCGGCCGCCCCCTTCACCATGAAGATGGCTTCCTCCGACGCTAACCCCTCCG
ACGGTTCCACCGCTAACCTGGTGCCCGAGGTGAACAACGAGGTGATGGCTCTCGAGCCCG
TGGTGGGCGCTGCTATCGCTGCTCCCGTGGCTGGCCAGCAGAACGTGATCGACCCCTGGA
TCCGTAACAACTTCGTGCAGGCTCCCGGTGGCGAGTTCACCGTGTCCCCCCGTAACGCTC
CCGGCGAGATCCTGTGGTCCGCTCCCCTGGGTCCCGACCTGAACCCCTACCTGTCCCACC
TGGCTCGTATGTACAACGGTTACGCTGGCGGTTTCGAGGTGCAGGTGATCCTGGCTGGTA
ACGCTTTCACCGCTGGCAAGATCATCTTCGCTGCTGTGCCCCCAACTTCCCCACCGAGG
GCCTGAGCCCCTCCCAGGTGACCATGTTCCCCCACATCATCGTGGACGTGCGCCAGCTCG
AGCCTGTGCTGATCCCCCTGCCCGACGTGCGCAACAACTTCTACCACTACAACCAGTCCA
ACGACCCCACCATCAAGCTGATCGCTATGCTGTACACCCCCCTGCGTGCTAACAACGCTG
GTGACGACGTGTTCACTGTGTCCTGCCGTGTGCTGACCCGTCCCTCCCCGACTTCGACT
TCATCTTCCTGGTGCCCCCTACCGTGGAGTCCCGTACCAAGCCCTTCACCGTGCCCATCC
TGACCGTGGAGGAGATGACCAACTCCCGTTTCCCCATCCCCCTCGAGAAGCTGTTCACCG
GTCCCTCCGGTGCTTTCGTGGTGCAGCCCCAGAACGGTCGTTGCACCACCGACGGTGTCC
TGCTGGGCACCACTCAGCTGTCCCCCGTGAACATCTGCACCTTCCGTGGTGACGTGACCC
ACATCGCTGGCACCCAAGAGTACACCATGAACCTGGCCTCCCAGAACTGGAACAACTACG
ACCCTACCGAGGAGATCCCCGCTCCTCTGGGCACCCCTGACTTCGTGGGCAAGATCCAGG
GTGTCCTGACCCAGACCACCCGCGGTGACGGCTCCACCCGTGGTCACAAGGCTACCGTGT
CCACCGGTTCCGTGCACTTCACCCCCAAGCTGGGTTCCGTCCAGTTCTCCACCGACACCT
CCAACGACTTCGAGACTGGCCAGAACACCAAGTTCACCCCCGTGGGTGTGGTGCAGGACG
GTTCTACCACCCACCAGAACGAGCCCCAGCAGTGGGTGCTGCCTGACTACTCCGGTCGTG
ACTCCCACAACGTGCACCTGGCTCCCGCTGTGGCTCCCACCTTCCCCGGCGAGCAGCTGC
TGTTCTTCCGTTCCACCATGCCCGGTTGCTCCGGTTACCCCAACATGAACCTCGACTGCC
TGCTGCCTCAGGAGTGGGTCCAGCACTTCTACCAGGAGGCTGCTCCCGCTCAGTCCGACG
TGGCTCTGCTGCGTTTCGTGAACCCCGACACCGGTCGTGTGCTGTTCGAGTGCAAGCTGC
ACAAGTCCGGTTACGTGACCGTGGCTCACACCGGCCAGCACGACCTGGTGATCCCTCCCA
ACGGTTACTTCCGTTTCGACTCCTGGGTGAACCAGTTCTACACCCTGGCTCCCATGGGTA
ACGGCACCGGTCGTCGTCGTGCTCTGTAATGGCTGGAGCTTTCTTTGCTGGATTGGCATC
TGATGTCCTTGGCTCTGGACTTGGTTCCCTAATCAATGCTGGGCTGGGCCATCAACCA
AAAAGTTGAATTTGAAAATAACAGAAAATTGCAACAAGCTTGGCGCGCC    (SEQ ID NO: 3)
```

| Lane 1 | Molecular weight marker |
| Lane 2 | Sucrose gradient fraction 1 |
| Lane 3 | Sucrose gradient fraction 2 |
| Lane 4 | Sucrose gradient fraction 3 |
| Lane 5 | Sucrose gradient fraction 4 |
| Lane 6 | Sucrose gradient fraction 5 |
| Lane 7 | Sucrose gradient fraction 6 |
| Lane 8 | Sucrose gradient fraction 7 |
| Lane 9 | Sucrose gradient fraction 8 |

FIGURE 20

MKMASNDAAPSNDGAAGLVPExNNExMALEPVAGAAIAAPLTGQxNIIDPWIRxNFVQAPNGEFTVSPRNSPGEVLL
NLELGPELNPYLAHLARMYNGYAGGxEVQVxLAGNAFTAGKLVFAAIPPHFPIxNLSPxQITMFPHVIIDVRTLEPV
LLPLPDVRNNFFHYNQxxDPRMRLVAMLYTPLRSNGSGDDVFTVSCRVLTRPSPDFDFNYLVPPTVESKTKPFTLPI
LTIGELSNSRFPVPIDxLYTSPNExIVVQCQNGRxTLDGELxGTTQLxPSxICAFRGxxTRxxAHLSDQxN------
-xHRWNIQxTNLNGTPFDPxEDIPAPLGTPDFxGxVFGVxSQRNPDNT-------xRAHDAxVxTxSxxFTPKLGSV
xIGTWExxDFDxNQPTKFTPV—GLxDTxHFNQWVLPxYSGALTLNMNLAPSVAPxFPGEQLLFFRSxLPLKGGxSNG
AIDCLLPQEWVQHFYQESAPSxTxVALVRYxNPDTGRVLFEAKLHRxGFMTVAxNGSxPIVVPPNGYFRFDSWVNQF
YSLAPMGTGNGRRRI (SEQ ID NO: 7)

FIGURE 21

MMMASKDATxSADGASGAGQLVPEVNTADPLPMDPVAGSSTAVATAGQVNxIDPWIINNFVQAPQGEFTISPNNTP
GDVLFDLQLGPHLNPFLSHLSQMYNGWVGNMRVRIxLAGNAFTAGKIIVCCVPPGFxSxxLTIAQATLFPHVIADVR
TLDPIEVPLEDVRNVLYHNND-NQPTMRLVCMLYTPLRTGGGSGxxDSFVVAGRVLTCPSPDFNFLFLVPPTVEQKT
RPFTVPNIPLxxLSNSRxPxPIxGMxLSPDxxQxVQFQNGRCTIDGQLLGTTPVSxSQLxKxRGxITSGxRVLNLTE
LDGxPFMAFxxPAPxGFPDLGxCDWHIxMSKxPNSSxQxxPxxxxSVxTNxQxFVPHLGSIQxDExxS-xxGDYIGT
IxWISPPSxPxGxxxNLWKIPDYGSSLxEAxxLAPxVYPPGFGEVLVYFMSxxPGPNxxGAPNxVPCLLPQEYITHF
xSEQAPTxGEAALLHYVDPDTNRNLGEFKLYPGGYLTCVPNGxSxGPQQLPLNGVFVFVSWVSRFYQLKPVGTASxA
RGRLGVRR (SEQ ID NO: 12)

FIGURE 22

```
MCLYTRVLILHYHLLPLYGPLYHPRPLPxxxxxxxYxxxxIxCxxxxxxxxxxVNVxxIFxQMxLWRPSDxTVYLPPP
-PVSKVVxTDxYVxRTNIFYHAGSSRLLAVGHPYFxIKKxxxNKxxVPKVSGYQYRVFRVxLPDPNKFGLPDTSxYN
PxTQRLVWACxGVEVGRGQPLGVGxSGHPLLNKLDDTENSxAYxxNxGxDNRxNVSMDYKQTQLCxxGCAPPIGEHW
GKGTxCxNxxVxxGDCPPLELINTVIQDGDMVDTGFGAMDFxTLQxNKSEVPLDICxSICKYPDYLQMxADPYGDSL
FFYLRREQMFARHFFNRAGTVGExVPDDLYIKGxGxxASxASSxYxPTPSGSxVTSDAQLFNKPYWLQKAQGHNNGI
CWGNQLFVTVVDTTRSTNMTLCAS-xSxS

VIRUS-LIKE PARTICLES COMPRISING COMPOSITE CAPSID AMINO ACID SEQUENCES FOR ENHANCED CROSS REACTIVITY

CROSS-REFERENCE TO RELATED APPLICATIONS

This application is a continuation-in-part of International Application No. PCT/US2009/053249, filed Aug. 10, 2009, which claims the benefit of U.S. Provisional Application No. 61/087,504, filed Aug. 8, 2008, and U.S. Provisional Application No. 61/218,603, filed Jun. 19, 2009, all of which are herein incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LIGO_022_02US_SeqList_ST25.txt, date recorded: Feb. 8, 2011, file size 120 kilobytes).

FIELD OF THE INVENTION

The invention is in the field of vaccines, particularly vaccines comprising virus-like particles with a composite amino acid sequence derived from a consensus sequence representing two or more capsid proteins from non-enveloped viruses. In addition, the invention relates to methods of preparing vaccine compositions and methods of inducing a protective immune response using the vaccine compositions of the invention.

BACKGROUND OF THE INVENTION

The prevalent approach to preparing vaccines for viruses with seasonal or year-to-year patterns is modeled by commercial Influenza vaccines which require the anticipation, publication, and subsequent synthesis of a new vaccine when the virus evolves to present a different antigenic profile. This approach causes significant timeline delays and cost as new antigens are synthesized in anticipation of the next years viral strain. Further, as evidenced by the failings of the 2008 influenza vaccine, errors in the predicted strain can result in significant disease related costs as patients are under-protected. Thus, improved methods for designing and preparing vaccines to protect against multiple circulating strains of disease-causing virus is desirable.

Noroviruses are non-cultivatable human Caliciviruses that have emerged as the single most important cause of epidemic outbreaks of nonbacterial gastroenteritis (Glass et al. (2000) J Infect Dis, Vol. 181 (Sup 2): S254-S261; Hardy et al. (1999) Clin Lab Med, Vol. 19(3): 675-90). These viruses have been grouped into five different genogroups of which genogroups I and II are further subdivided into greater than 25 genotypes and are the agents for the vast majority of illness in humans attributed to this virus. There are significant challenges to the development of vaccines against Norovirus, including the inability to propagate the virus in culture and suitable animal models of acute gastroenteritis. Standard virologic techniques including viral attenuation or in vitro neutralization assays are therefore not possible today.

Noroviruses contain a 7.5 Kb single strand positive sense RNA genome that contains three open reading frames. The major viral capsid protein (VP1) is encoded by ORF2 and expression of this protein results in the spontaneous assembly of virus-like particles (VLPs), which mimic the structure of the virus but are incapable of replication. This structure is composed of 180 monomeric subunits of VP1 and are candidate vaccines to prevent acute gastroenteritis. The VP1 monomer has two domains: a shell (S) domain that forms the inner viral core and a prominent protruding (P) domain linked by a flexible hinge. The P domain is further subdivided into two subdomains P1 and P2, which is the most surface exposed region and is thought to contain important cell recognition and antigenic sites. Homology analysis indicates that the majority of the hypervariable amino acid regions of VP1 are located in the P2 domain (Allen et al. (2008) PLoS One, Vol. 1:1-9).

Recent epidemiology studies have lead to the hypothesis that Norovirus evolution is epochal with periods of stasis followed by emergence of novel epidemic strains, similar to that observed for Influenza virus. Most recent outbreaks appear to be related to emergence of variant virus in the GII.4 genotype at a persistence interval of around two years. There is a need in the art for a vaccine candidate that provides antigenic epitopes that would be cross protective for multiple Norovirus, or other non-enveloped virus strains, which would obviate the need for construction of vaccines for each contemporary outbreak strain.

SUMMARY OF THE INVENTION

The present invention is based, in part, on the discovery that a polypeptide comprising a composite capsid sequence, which combines epitopes from a number of circulating viral strains, can be used to produce a more robust immunological response to multiple viral strains. Such a polypeptide can be used to prepare vaccine formulations that are protective against several circulating strains of the virus, and therefore improve strain-to-strain and year-to-year protection.

The present invention provides at least one polypeptide having a composite amino acid sequence, wherein said composite amino acid sequence is derived from a consensus sequence representing the capsid proteins of two or more circulating strains of a non-enveloped virus, and wherein the at least one polypeptide forms a virus-like particle when expressed in a host cell and contains at least 1 different amino acid as compared to each of the capsid sequences of said two or more circulating strains. In one embodiment, the virus-like particle comprising the at least one composite polypeptide has antigenic properties of the two or more circulating strains of the non-enveloped virus. In another embodiment, the composite polypeptide or composite virus-like particle provides an increase in antisera cross-reactivity to one or more circulating strains of the non-enveloped virus as compared to the antisera cross-reactivity obtained by immunizing with a virus-like particle containing only protein from said one or more circulating strains.

The virus-like particle may comprise at least one polypeptide having a composite amino acid sequence derived from a consensus sequence representing capsid proteins of two or more circulating strains of a non-enveloped virus, wherein the non-enveloped virus is selected from the group consisting of Calicivirus, Picornavirus, Astrovirus, Adenovirus, Reovirus, Polyomavirus, Papillomavirus, Parvovirus, and Hepatitis E virus. In one embodiment, the non-enveloped virus is a Calicivirus. In another embodiment, the Calicivirus is a Norovirus or Sapovirus. The Norovirus may be a genogroup I or genogroup II Norovirus.

The consensus sequence may be derived from two or more Norovirus strains classified in the same genogroup and genotype. In one embodiment, the consensus sequence is derived from genogroup II, genotype 4 Norovirus strains, such as Houston (GenBank Sequence ABY27560), Minerva (also known as Den Haag; GenBank Sequence ABL74395), and Laurens (also known as Yerseke; GenBank Sequence ABL74391) strains. In another embodiment, the consensus sequence is derived from Norovirus strains from at least two different genotypes within a genogroup. In still another embodiment, the consensus sequence is derived from Norovirus strains from at least two different genogroups.

The present invention also encompasses a virus-like particle comprising at least one composite polypeptide derived from two or more circulating Calicivirus strains and a capsid protein from a second non-enveloped virus, such as Norovirus. The capsid protein may be a VP1 and/or VP2 protein from a genogroup I or genogroup II Norovirus. In another embodiment, the virus-like particle comprises at least one composite polypeptide derived from two or more circulating strains of a Calicivirus and a second composite polypeptide derived from two or more circulating strains of a second Calicivirus. Preferably, the virus-like particle has antigenic properties of the two or more circulating strains of the first Calicivirus and the two or more circulating strains of the second Calicivirus.

The present invention also provides an isolated polypeptide or fragment thereof having a composite amino acid sequence, wherein said composite amino acid sequence is derived from a consensus sequence representing the capsid proteins of two or more circulating strains of a non-enveloped virus, and wherein the polypeptide contains at least 1 different amino acid as compared to each of the capsid sequences of said two or more circulating strains. The non-enveloped virus may be a Calicivirus, such as a Sapovirus or Norovirus. Alternatively, the non-enveloped virus may be a Papillomavirus.

The present invention contemplates vaccine formulations comprising one or more composite polypeptides or composite virus-like particles of the invention. Each of the composite virus-like particles comprises at least one polypeptide having a composite amino acid sequence derived from a consensus sequence representing the capsid proteins from two or more circulating strains of a non-enveloped virus. The non-enveloped virus may be a genogroup I or genogroup II Norovirus. In some embodiments, the vaccine formulation further comprises an adjuvant. In other embodiments, the vaccine formulation further comprises a delivery agent. In still other embodiments, the vaccine formulation further comprises a pharmaceutically acceptable carrier. The vaccine formulation may be a liquid formulation or a dry powder formulation.

The invention also provides a method of inducing a protective immunity to a viral infection in a subject comprising administering to the subject a vaccine formulation disclosed herein. In one embodiment, the viral infection is a Norovirus infection. In another embodiment, the vaccine formulation confers protection from one or more symptoms of Norovirus infection.

The present invention also contemplates a method of making a composite virus-like particle. In one embodiment, the method comprises aligning amino acid sequences of capsid proteins from two or more circulating strains of a non-enveloped virus; determining a consensus sequence from said aligned amino acid sequences; preparing a composite sequence based on said consensus sequence that contains at least 1 different amino acid as compared to each of the capsid sequences of said two or more circulating strains; and expressing said composite sequence in a host cell, thereby producing a virus-like particle. The non-enveloped virus may be a Calicivirus, Picornavirus, Astrovirus, Adenovirus, Reovirus, Polyomavirus, Papillomavirus, Parvovirus, and Hepatitis E virus.

BRIEF DESCRIPTION OF THE FIGURES

FIG. 1. Amino acid consensus sequence of VP1 proteins from genogroup II, genotype 4 Norovirus (SEQ ID NO: 2). The consensus sequence was determined from an alignment of Houston (GenBank Sequence ABY27560), Minerva (also known as Den Haag and GenBank Sequence ABL74395), and Laurens (also known as Yerseke and GenBank Sequence ABL74391) strains.

FIG. 2. Nucleotide sequence encoding the composite VP1 protein from genogroup II, genotype 4 Norovirus (SEQ ID NO: 3). The amino acid sequence encoded by this nucleotide sequence is provided as SEQ ID NO: 22.

FIG. 20. Amino acid consensus sequence of VP1 proteins from genogroup II Norovirus (SEQ ID NO: 7). The consensus sequence was determined from an alignment of GII.1 (Accession Number: AAL13001), GII.2 Snow Mountain (Accession Number: AAB61685), and GII.3 (Accession Number: AAL12998) strains. The "x" indicates positions in which the amino acid differed among all three strains.

FIG. 21. Amino acid consensus sequence of VP1 proteins from genogroup I Norovirus (SEQ ID NO: 12). The consensus sequence was determined from an alignment of Norwalk virus (Accession Number: M87661), Southampton (Accession Number: Q04542), and Chiba virus (Accession Number: BAB18267) strains. The "x" indicates positions in which the amino acid differed among all three strains.

FIG. 22. Amino acid consensus sequence of L1 proteins from Human Papillomavirus (SEQ ID NO: 17). The consensus sequence was determined from an alignment of HPV-11, HPV-16, and HPV-18 viral strains. The "x" indicates positions in which the amino acid differed among all three strains.

DETAILED DESCRIPTION OF THE INVENTION

Figure 3:
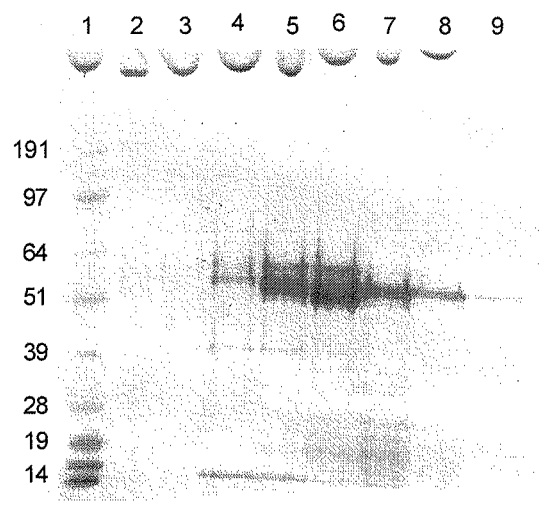
FIG. 3. SDS-PAGE/Coomassie analysis of sucrose gradient purified composite VLPs.

The present invention provides vaccine formulations comprising a polypeptide having a composite amino acid sequence, wherein the composite amino acid sequence is derived from capsid sequences of circulating strains of non-enveloped virus. Virus-like particles produced from such polypeptide sequences provide antigenic epitopes for several viral strains and can be used to induce an immune response that is protective against viral infection from multiple strains. Accordingly, the present invention provides a virus-like particle comprising at least one polypeptide having a composite amino acid sequence. A "composite amino acid sequence" or "composite sequence", as used herein, is a sequence derived from a consensus sequence of at least two viral protein sequences. In one embodiment, the viral protein sequences are capsid sequences. A composite amino acid sequence may be derived from a consensus sequence by selecting one of two or more amino acids at the variable positions in the consensus sequence.

As used herein, a "consensus sequence" is a sequence containing one or more variable amino acids, and is determined by aligning and comparing the viral protein sequences of two or more viruses. A consensus sequence may also be determined by aligning and comparing the nucleotide sequences of two or more viruses. The consensus sequence may be determined from protein or nucleotide sequences of two or more, three or more, four or more, five or more, six or more, seven or more, eight or more, or nine or more circulating strains of a non-enveloped virus.

The polypeptide having a composite amino acid sequence may contain at least one different, at least two different, at least three different, at least four different, at least five different, at least six different, at least seven different, at least eight different, at least nine different, at least ten different, at least fifteen different, at least twenty different, at least twenty-five different, at least thirty different, at least thirty-five different, at least forty different, at least forty-five different, or at least fifty different amino acids as compared to each of the protein sequences of the two or more circulating strains used to determine the consensus sequence. In some embodiments, the polypeptide having a composite amino acid sequence may form a virus-like particle when expressed in a host cell.

In one embodiment of the invention, the virus-like particle (VLP) comprises at least one polypeptide having a composite amino acid sequence, wherein said composite amino acid sequence is derived from a consensus sequence representing the capsid proteins of two or more circulating strains of a non-enveloped virus, and wherein the at least one polypeptide forms a virus-like particle when expressed in a host cell and contains at least 1 different amino acid as compared to each of the capsid sequences of said two or more circulating strains. Preferably, the virus-like particle has antigenic properties of the two or more, three or more, four or more, five or more, six or more, seven or more, eight or more, or nine or more circulating strains of a non-enveloped virus. In some embodiments, the virus-like particle provides an increase in antisera cross-reactivity to one or more, two or more, three or more, four or more, five or more, six or more, seven or more, eight or more, or nine or more circulating strains of the non-enveloped virus as compared to the antisera cross-reactivity obtained by immunizing with a virus-like particle containing only protein from one or more circulating strains. In one embodiment, the virus-like particle provides at least a two-fold increase in antisera cross-reactivity.

In another embodiment, the virus-like particle comprises at least one polypeptide having a composite amino acid sequence derived from a consensus sequence representing the capsid proteins of two or more circulating strains of a non-enveloped virus, wherein the non-enveloped virus is selected from the group consisting of Calicivirus, Picornavirus, Astrovirus, Adenovirus, Reovirus, Polyomavirus, Papillomavirus, Parvovirus, and Hepatitis E virus. The invention also includes strains of non-enveloped viruses that have not yet been characterized or discovered at the time of filing. In some embodiments, among others, the non-enveloped virus is a Calicivirus. Caliciviruses are divided into four genera: Norovirus and Sapovirus, which cause infection in humans, and Lagovirus and Vesivirus, which are associated with veterinary infections. In preferred embodiments, the Calicivirus is a Sapovirus or Norovirus.

The Norovirus genus is split primarily into two major genogroups (GI and GII). Two other genogroups (GIII and GIV) are proposed, but generally accepted. Representative of GIII is the bovine, Jena strain. GIV contains one virus, Alphatron, at this time. The GI and GII groups may be further segregated into clusters or genotypes based on genetic classification (Ando et al. (2000) J. Infectious Diseases, Vol. 181(Supp2):S336-S348; Lindell et al. (2005) J. Clin. Microbiol., Vol. 43(3): 1086-1092). As used herein, the term genetic clusters is used interchangeably with the term genotypes. Within genogroup I, there are 6 GI clusters (with prototype virus strain name): GI.1 (Norwalk); GI.2 (Southhampton); GI.3 (Desert Shield); GI.4 (Cruise Ship virus/Chiba); GI.5 (318/Musgrove); and GI.6 (Hesse). Within genogroup II, there are 9 GII clusters (with prototype virus strain name): GII.1 (Hawaii); 011.2 (Snow Mountain/Melksham); 011.3 (Toronto); GII.4 (Bristol/Lordsdale); GII.5 (290/Hillingdon); 011.6 (269/Seacroft); GII.7 (273/Leeds); GII.8 (539/Amsterdam); and GII.9 (378). The circulating Norovirus strains are classified through comparison to prototype strains belonging to these genetic clusters. The most prevalent circulating strains belong to genogroup II.

Nucleic acid and protein sequences for a number of Norovirus isolates are known. Additional representative, non-limiting sequences, including sequences of ORF1, ORF2, ORF3, and their encoded polypeptides from Norovirus isolates are listed in the National Center for Biotechnology Information (NCBI) database. In one embodiment of the invention, the Norovirus may be a genogroup I or genogroup II Norovirus. Composite and consensus amino acid sequences may be determined from any of the known Norovirus strains. See, for example, GenBank entries: Norovirus genogroup 1 strain Hu/NoV/West Chester/2001/USA, GenBank Accession No. AY502016; Norovirus genogroup 2 strain Hu/NoV/Braddock Heights/1999/USA, GenBank Accession No. AY502015; Norovirus genogroup 2 strain Hu/NoV/Fayette/1999/USA, GenBank Accession No. AY502014; Norovirus genogroup 2 strain Hu/NoV/Fairfield/1999/USA, GenBank Accession No. AY502013; Norovirus genogroup 2 strain Hu/NoV/Sandusky/1999/USA, GenBank Accession No. AY502012; Norovirus genogroup 2 strain Hu/NoV/Canton/1999/USA, GenBank Accession No. AY502011; Norovirus genogroup 2 strain Hu/NoV/Tiffin/1999/USA, GenBank Accession No. AY502010; Norovirus genogroup 2 strain Hu/NoV/CS-E1/2002/USA, GenBank Accession No. AY50200; Norovirus genogroup 1 strain Hu/NoV/Wisconsin/2001/USA, GenBank Accession No. AY502008; Norovirus genogroup 1 strain Hu/NoV/CS-841/2001/USA, GenBank Accession No. AY502007; Norovirus genogroup 2 strain Hu/NoV/Hiram/2000/USA, GenBank Accession No. AY502006; Norovirus genogroup 2 strain Hu/NoV/Tontogany/1999/USA, GenBank Accession No. AY502005; Norwalk virus, complete genome, GenBank Accession No. NC.sub.--001959; Norovirus Hu/GI/Otofuke/1979/JP genomic RNA, complete genome, GenBank Accession No. AB 187514; Norovirus Hu/Hokkaido/133/2003/JP, GenBank Accession No. AB212306; Norovirus Sydney 2212, GenBank Accession No. AY588132; Norwalk virus strain SN2000JA, GenBank Accession No. AB190457; Lordsdale virus complete genome, GenBank Accession No. X86557; Norwalk-like virus genomic RNA, Gifu'96, GenBank Accession No. AB045603; Norwalk virus strain Vietnam 026, complete genome, GenBank Accession No. AF504671; Norovirus Hu/GII.4/2004/N/L, GenBank Accession No. AY883096; Norovirus Hu/GII/Hokushin/03/JP, GenBank Accession No. AB 195227; Norovirus Hu/GII/Kamo/03/JP, GenBank Accession No. AB195228; Norovirus Hu/GII/Sinsiro/97/JP, GenBank Accession No. AB 195226; Norovirus Hu/GII/Ina/02/JP, GenBank Accession No. AB195225; Norovirus Hu/NLV/GII/Neustrelitz260/2000/DE, GenBank Accession No. AY772730; Norovirus Hu/NLV/Dresden174/pUS-NorII/1997/GE, GenBank Accession No. AY741811; Norovirus Hu/NLV/Oxford/B2S16/2002/UK, GenBank Accession No. AY587989; Norovirus Hu/NLV/Oxford/B4S7/2002/UK, GenBank Accession No. AY587987; Norovirus Hu/NLV/Witney/B7S2/2003/UK, GenBank Accession No. AY588030; Norovirus Hu/NLV/Banbury/B9S23/2003/UK, GenBank Accession No. AY588029; Norovirus Hu/NLV/Chipping-Norton/2003/UK, GenBank Accession No. AY588028; Norovirus Hu/NLV/Didcot/B9S2/2003/UK, GenBank Accession No. AY588027; Norovirus Hu/NLV/Oxford/B8S5/2002/UK, GenBank Accession No. AY588026; Norovirus Hu/NLV/Oxford/B6S4/2003/UK, GenBank Accession No. AY588025; Norovirus Hu/NLV/Oxford/B6S5/2003/UK, GenBank Accession No. AY588024; Norovirus Hu/NLV/Oxford/B5S23/2003/UK, GenBank Accession No. AY588023; Norovirus Hu/NLV/Oxford/B6S2/2003/UK, GenBank Accession No. AY588022; Norovirus Hu/NLV/Oxford/B6S6/2003/UK, GenBank Accession No. AY588021; Norwalk-like virus isolate Bo/Thirsk10/00/UK, GenBank Accession No. AY126468; Norwalk-like virus isolate Bo/Penrith55/00/UK, GenBank Accession No. AY126476; Norwalk-like virus isolate Bo/Aberystwyth24/00/UK, GenBank Accession No. AY126475; Norwalk-like virus isolate Bo/Dumfries/94/UK, GenBank Accession No. AY126474; Norovirus NLV/IF2036/2003/Iraq, GenBank Accession No. AY675555; Norovirus NLV/IF1998/2003/Iraq, GenBank Accession No. AY675554; Norovirus NLV/BUDS/2002/USA, GenBank Accession No. AY660568; Norovirus NLV/Paris Island/2003/USA, GenBank Accession No. AY652979; Snow Mountain virus, complete genome, GenBank Accession No. AY134748; Norwalk-like virus NLV/Fort Lauderdale/560/1998/US, GenBank Accession No. AF414426; HuNorovirus/hiroshima/1999/JP (9912-02F), GenBank Accession No. AB044366; Norwalk-like virus strain 11MSU-MW, GenBank Accession No. AY274820; Norwalk-like virus strain B-1SVD, GenBank Accession No. AY274819; Norovirus genogroup 2 strain Hu/NoV/Farmington Hills/2002/USA, GenBank Accession No. AY502023; Norovirus genogroup 2 strain Hu/NoV/CS-G4/2002/USA, GenBank Accession No. AY502022; Norovirus genogroup 2 strain Hu/NoV/CS-G2/2002/USA, GenBank Accession No. AY502021; Norovirus genogroup 2 strain Hu/NoV/CS-G12002/USA, GenBank Accession No. AY502020; Norovirus genogroup 2 strain Hu/NoV/Anchorage/2002/USA, GenBank Accession No. AY502019; Norovirus genogroup 2 strain Hu/NoV/CS-D1/2002/CAN, GenBank Accession No. AY502018; Norovirus genogroup 2 strain HuNoV/Germanton/2002/USA, GenBank Accession No. AY502017; Human calicivirus NLV/GII/Langen1061/2002/DE, complete genome, GenBank Accession No. AY485642; Murine norovirus 1 polyprotein, GenBank Accession No. AY228235; Norwalk virus, GenBank Accession No. AB067536; Human calicivirus NLV/Mex7076/1999, GenBank Accession No. AF542090; Human calicivirus NLV/Oberhausen 455/01/DE, GenBank Accession No. AF539440; Human calicivirus NLV/Herzberg 385/01/DE, GenBank Accession No. AF539439; Human calicivirus NLV/Boxer/2001/US, GenBank Accession No. AF538679; Norwalk-like virus genomic RNA, complete genome, GenBank Accession No. AB081723; Norwalk-like virus genomic RNA, complete genome, isolate:Saitama U201, GenBank Accession No. AB039782; Norwalk-like virus genomic RNA, complete genome, isolate:Saitama U18, GenBank Accession No. AB039781; Norwalk-like virus genomic RNA, complete genome, isolate:Saitama U25, GenBank Accession No. AB039780; Norwalk virus strain:U25GII, GenBank Accession No. AB067543; Norwalk virus strain: U201 GII, GenBank Accession No. AB067542; Norwalk-like viruses strain 416/97003156/1996/LA, GenBank Accession No. AF080559; Norwalk-like viruses strain 408/97003012/1996/FL, GenBank Accession No. AF080558; Norwalk-like virus NLV/Burwash Landing/331/1995/US, GenBank Accession No. AF414425; Norwalk-like virus NLV/Miami Beach/326/1995/US, GenBank Accession No. AF414424; Norwalk-like virus NLV/White River/290/1994/US, GenBank Accession No. AF414423; Norwalk-like virus NLV/New Orleans/306/1994/US, GenBank Accession No. AF414422; Norwalk-like virus NLV/Port Canaveral/301/1994/US, GenBank Accession No. AF414421; Norwalk-like virus NLV/Honolulu/314/1994/US, GenBank Accession No. AF414420; Norwalk-like virus NLV/Richmond/283/1994/US, GenBank Accession No. AF414419; Norwalk-like virus NLV/Westover/302/1994/US, GenBank Accession No. AF414418; Norwalk-like virus NLV/UK3-17/12700/1992/GB, GenBank Accession No. AF414417; Norwalk-like virus NLV/Miami/81/1986/US, GenBank Accession No. AF414416; Snow Mountain strain, GenBank Accession No. U70059; Desert Shield virus DSV395, GenBank Accession No. U04469; Norwalk virus, complete genome, GenBank Accession No. AF093797; Hawaii calicivirus, GenBank Accession No. U07611; Southampton virus, GenBank Accession No. L07418; Norwalk virus (SRSV-KY-89/89/J), GenBank Accession No. L23828; Norwalk virus (SRSV-SMA/76/US), GenBank Accession No. L23831; Camberwell virus, GenBank Accession No. U46500; Human calicivirus strain Melksham, GenBank Accession No. X81879; Human calicivirus strain MX, GenBank Accession No. U22498; Minireovirus TV24, GenBank Accession No. U02030; and Norwalk-like virus NLV/Gwynedd/273/1994/US, GenBank Accession No. AF414409; sequences of all of which (as entered by the date of filing of this application) are herein incorporated by reference. Additional Norovirus sequences are disclosed in the following patent publications: WO 2005/030806, WO 2000/79280, JP2002020399, US2003129588, U.S. Pat. No. 6,572,862, WO 1994/05700, and WO 05/032457, all of which are herein incorporated by reference in their entireties. See also Green et al. (2000) J. Infect. Dis., Vol. 181(Suppl. 2):S322-330; Wang et al. (1994) J. Virol., Vol. 68:5982-5990; Chen et al. (2004) J. Virol., Vol. 78: 6469-6479; Chakravarty et al. (2005) J. Virol., Vol. 79: 554-568; Hansman et al. (2006) J. Gen. Virol., Vol. 87:909-919; Bull et al. (2006) J. Clin. Micro., Vol. 44(2):327-333; Siebenga, et al. (2007) J. Virol., Vol. 81(18):9932-9941, and Fankhauser et al. (1998) J. Infect. Dis., Vol. 178:1571-1578; for sequence comparisons and a discussion of genetic diversity and phylogenetic analysis of Noroviruses.

Nucleic acid and protein sequences for a number of Sapovirus isolates are also known. Representative Sapovirus sequences, including sequences of ORF1 and ORF2, and their encoded polypeptides from Sapovirus isolates are listed in the National Center for Biotechnology Information (NCBI) database. See, for example, GenBank entries: Sapovirus Mc10, GenBank Accession No. NC.sub.--010624; Sapporo virus, GenBank Accession No. U65427; Sapovirus Mc10, GenBank Accession No. AY237420; Sapovirus SaKaeo-15/Thailand, GenBank Accession No. AY646855; Sapporo virus, GenBank Accession No. NC.sub.--006269; Sapovirus C12, GenBank Accession No. NC.sub.--006554; Sapovirus C12, GenBank Accession No. AY603425; Sapovirus Hu/Dresden/pJG-Sap01/DE, GenBank Accession No. AY694184; Human calicivirus SLV/cruise ship/2000/USA, GenBank Accession No. AY289804; Human calicivirus SLV/Arg39, GenBank Accession No. AY289803; Porcine enteric calicivirus strain LL14, GenBank Accession No. AY425671; Porcine enteric calicivirus, GenBank Accession No. NC.sub.--000940; Human calicivirus strain Mc37, GenBank Accession No. AY237415; Mink enteric calicivirus strain Canada 151A, GenBank Accession No. AY144337; Human calicivirus SLV/Hou7-1181, GenBank Accession No. AF435814; Human calicivirus SLV/Mex14917/2000, GenBank Accession No. AF435813; Human calicivirus SLV/Mex340/1990, GenBank Accession No. AF435812; Porcine enteric calicivirus, GenBank Accession No. AF182760; Sapporo virus-London/29845, GenBank Accession No. U95645; Sapporo virus-Manchester, GenBank Accession No. X86560; Sapporo virus-Houston/86, GenBank Accession No. U95643; Sapporo virus-Houston/90, GenBank Accession No. U95644; and Human calicivirus strain HuCV/Potsdam/2000/DEU, GenBank Accession No. AF294739; sequences of all of which (as entered by the date of filing of this application) are herein incorporated by reference. See also Schuffenecker et al. (2001) Arch Virol., Vol. 146(11): 2115-2132; Zintz et al. (2005) Infect. Genet. Evol., Vol. 5:281-290; Farkas et al. (2004) Arch. Virol., Vol. 149:1309-1323; for sequence comparisons and a discussion of genetic diversity and phylogenetic analysis of Sapoviruses.

The composite and consensus amino acid sequences may be derived from capsid sequences of at least two Norovirus genogroup I or genogroup II strains. In one embodiment, the VLP comprises a polypeptide having a composite sequence derived from a consensus sequence of the capsid proteins from two or more genogroup II, genotype 4 Norovirus strains. Non-limiting examples of genogroup II, genotype 4 Norovirus strains include Houston strain, Minerva strain, Laurens strain, Bristol strain, Lordsdale strain, Farmington Hills strain, Hunter strain, Carlow strain, and the US95/96-US, 2006a, and 2006b strains.

In another embodiment of the invention, the virus-like particle is comprised of at least one composite polypeptide wherein the sequence of the composite polypeptide is derived from the VP1 sequences of Houston, Minerva, and Laurens. In another embodiment, the composite sequence comprises or consists of SEQ ID NO: 1 or SEQ ID NO: 22. In still another embodiment, composite sequences based on Houston, Minerva, and Laurens may be derived from the consensus sequence defined by SEQ ID NO: 2.

In some embodiments, the consensus sequence may be determined from Norovirus strains from at least two different genotypes or at least two different genogroups. In one embodiment of the present invention the virus-like particle is comprised of at least one polypeptide having a composite amino acid sequence, wherein the composite amino acid sequence is derived from a consensus sequence of capsid proteins of Norovirus strains from at least two different genotypes within a genogroup. By way of example, the consensus sequence may be derived from the capsid sequences of genogroup II, genotype 2 and genogroup II, genotype 4 Norovirus strains. In another embodiment, the consensus sequence may be derived from the capsid sequences of three or more genotypes within a genogroup.

In other embodiments, the consensus sequence may be determined from Norovirus strains from at least two different genogroups. One such embodiment, among others, would be a VLP comprising a polypeptide having a composite amino acid sequence, wherein said composite amino acid sequence is derived from a consensus sequence of capsid proteins of genogroup I, genotype 1 and genogroup II, genotype 4 Norovirus strains.

The present invention also provides a virus-like particle (VLP) comprising a composite polypeptide derived from a consensus sequence of capsid proteins from two or more circulating strains of Norovirus and a capsid protein from a second Norovirus. The second Norovirus may be a genogroup I or genogroup II Norovirus. The capsid protein from the second Norovirus can be the major capsid protein, VP1, which is encoded by ORF 2, or the minor capsid protein, VP2, which is encoded by ORF 3, or combinations of VP1 and VP2. In one embodiment, the capsid protein from the second Norovirus is a VP1 protein from a genogroup I Norovirus.

In another embodiment, the invention provides a VLP comprising a composite polypeptide derived from a consensus sequence representing the capsid proteins of two or more circulating strains of Calicivirus and a second polypeptide having a second composite amino acid sequence, wherein said second composite amino acid sequence is derived from a consensus sequence representing the capsid proteins of two or more circulating strains of a second Calicivirus. Preferably, the virus-like particle has antigenic properties of the two or more circulating strains of the first Calicivirus and the two or more circulating strains of the second Calicivirus.

The second polypeptide contains at least one different, at least three different, at least five different, at least ten different, at least fifteen different, at least twenty different, at least twenty-five different, at least thirty different, at least thirty-five different, at least forty different, at least forty-five different, or at least fifty different amino acids as compared to each of the capsid sequences of said two or more circulating strains of the second Calicivirus. In some embodiments, the second polypeptide forms a virus-like particle when expressed in a host cell. In another embodiment, the second Calicivirus is a Norovirus. In another embodiment, the Norovirus is a genogroup I Norovirus. The genogroup I Norovirus may be any of the genogroup I strains disclosed herein. In one embodiment, the genogroup I Norovirus is selected from the group consisting of Norwalk virus, Southampton virus, Hesse virus, and Chiba virus.

The present invention also encompasses isolated polypeptides or fragments thereof having the composite amino acid sequences defined here in, as well as nucleic acids or vectors encoding the same. In one embodiment, the isolated polypeptide or fragment thereof has a composite amino acid sequence, wherein said composite amino acid sequence is derived from a consensus sequence representing the capsid proteins of two or more circulating strains of a non-enveloped virus, and wherein the polypeptide contains at least 1 different amino acid as compared to each of the capsid sequences of said two or more circulating strains. In another embodiment, the composite sequence contains at least 3 different amino acids compared to the capsid sequence of one or more circulating strains of the non-enveloped virus. In another embodiment, the composite sequence contains 5-50 different amino acids compared to the capsid sequence of one or more circulating strains of the non-enveloped virus. In still another embodiment, the consensus sequence is SEQ ID NO: 2.

The composite polypeptide may have a sequence derived from two or more circulating strains of any non-enveloped virus disclosed herein. In one embodiment, the non-enveloped virus is a Calicivirus. In another embodiment, the Calicivirus is a Norovirus or Sapovirus. In another embodiment, the Norovirus is a genogroup I or genogroup II Norovirus, or combinations thereof. In yet another embodiment, the isolated polypeptide comprises the amino acid sequence of SEQ ID NO: 1 or SEQ ID NO: 22.

In one embodiment, the present invention provides an isolated nucleic acid encoding the polypeptide having a composite amino acid sequence, wherein said composite amino acid sequence is derived from a consensus sequence representing the capsid proteins of two or more circulating strains of a non-enveloped virus, and wherein the polypeptide contains at least 1 different amino acid as compared to each of the capsid sequences of said two or more circulating strains. In another embodiment, the nucleic acid has the sequence of SEQ ID NO: 3. In another embodiment, the invention provides a vector comprising an isolated nucleic acid encoding a composite polypeptide. In yet another embodiment, the invention provides a host cell comprising a vector encoding a composite polypeptide.

The antigenic molecules of the present invention (e.g. VLPs, polypeptides, and fragments thereof) can be prepared by isolation and purification from the organisms in which they occur naturally, or they may be prepared by recombinant techniques. Once coding sequences for the desired particle-forming polypeptides have been isolated or synthesized, they can be cloned into any suitable vector or replicon for expression. Numerous cloning vectors are known to those of skill in the art, and the selection of an appropriate cloning vector is within the skill of an ordinary artisan. The vector is then used to transform an appropriate host cell. Suitable recombinant expression systems include, but are not limited to, bacterial (e.g. *E. coli, Bacillus subtilis*, and *Streptococcus*), baculovirus/insect, vaccinia, Semliki Forest virus (SFV), Alphaviruses (such as, Sindbis, Venezuelan Equine Encephalitis (VEE)), mammalian (e.g. Chinese hamster ovary (CHO) cells, HEK-293 cells, HeLa cells, baby hamster kidney (BHK) cells, mouse myeloma (SB20), and monkey kidney cells (COS)), yeast (e.g. *S. cerevisiae, S. pombe, Pichia pastori* and other *Pichia* expression systems), plant, and *Xenopus* expression systems, as well as others known in the art. Particularly preferred expression systems are mammalian cell lines, bacteria, insect cells, and yeast expression systems.

Each of the aforementioned antigens (e.g. VLPs, polypeptides, or fragments thereof) is preferably used in the substantially pure state. Depending on the expression system and host selected, VLPs are produced by growing host cells transformed by an expression vector under conditions whereby the particle-forming polypeptide is expressed and VLPs can be formed. The selection of the appropriate growth conditions is within the skill of the art.

Preferably the VLP antigens are prepared from insect cells such as Sf9, High Five, TniPro, *Aedes aegypti, Autographa*

*californica, Bombyx mori, Drosophila melanogaster, Spodoptera frugiperda*, and *Trichoplusia ni*. The procedures for producing VLPs in insect cell culture is well known in the art (see, for example, U.S. Pat. No. 6,942,865, which is incorporated herein by reference in its entirety). Briefly, the recombinant baculoviruses carrying the composite capsid sequence are constructed from the sythetic cDNAs. The recombinant baculovirus are then used to infect insect cell cultures (e.g. Sf9, High Five and TniPro cells) and composite VLPs can be isolated from the cell culture. A "composite VLP" is a VLP comprising at least one polypeptide having a composite amino acid sequence derived from a consensus sequence representing the capsid proteins of two or more circulating strains of a non-enveloped virus.

If the VLPs are formed intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990).

The particles are then isolated (or substantially purified) using methods that preserve the integrity thereof, such as, by density gradient centrifugation, e.g., sucrose gradients, PEG-precipitation, pelleting, and the like (see, e.g., Kirnbauer et al. J. Virol. (1993) 67:6929-6936), as well as standard purification techniques including, e.g., ion exchange and gel filtration chromatography.

General texts which describe molecular biological techniques, which are applicable to the present invention, such as cloning, mutation, and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and expression of capsid proteins of non-enveloped viruses, such as Calicivirus.

In some embodiments, the antigenic molecules of the present invention (e.g. VLPs, polypeptides, and fragments thereof) are produced in vivo by administration of a vector comprising an isolated nucleic acid encoding a composite polypeptide. Suitable vectors include, but are not limited to, viral vectors, such as Vesicular Stomatitis Virus (VSV) vector, Equine Encephalitis Virus (EEV) vector, Poxvirus vector, Adenovirus vector, Adeno-Associated Virus (AAV), retrovirus vector, and expression plasmids, such as pFastBacl, pWI-NEO, pSV2CAT, pOG44, pXT1, pSG, pSVK3, pBPV, pMSG, and pSVL. Other suitable vectors will be readily apparent to the skilled artisan.

The present invention also encompasses a vaccine formulation comprising the VLPs, polypeptides, or nucleic acids described herein. In one embodiment, the vaccine formulation comprises a composite VLP and a second virus-like particle, wherein said second virus-like particle comprises a capsid protein from a Norovirus. The second VLP may comprise a native capsid protein from a genogroup I or genogroup II Norovirus. The second VLP may comprise a full length Norovirus capsid protein such as VP1 and/or VP2 protein or certain VP1 or VP2 derivatives. Alternatively, the second VLP comprises a truncated capsid protein, such as a truncated VP1 protein. The truncation may be an N- or C-terminal truncation. Truncated capsid proteins are suitably functional capsid protein derivatives. Functional capsid protein derivatives are capable of raising an immune response in the same way as the immune response is raised by a VLP consisting of the full length capsid protein. Vaccine formulations comprising mixtures of VLPs are described in WO 2008/042789, which is herein incorporated by reference in its entirety. Purely by way of example the vaccine formulation can contain VLPs from one or more strains of Norovirus genogroup I together with VLPs comprising a composite protein from one or more strains of Norovirus genogroup II. Preferably, the Norovirus VLP mixture is composed of the strains of Norwalk and genogroup II, genotype 4 Noroviruses. In another embodiment, the vaccine formulation comprises a composite VLP and a Norwalk VLP, wherein the composite VLP comprises a polypeptide having an amino acid sequence of SEQ ID NO: 1 or SEQ ID NO: 22. In still another embodiment, the vaccine formulation comprises a first composite VLP and a second composite VLP, wherein said first and second composite VLPs comprise at least one polypeptide derived from different consensus sequences. For instance, a first composite VLP comprises a composite protein from one or more strains of Norovirus genogroup I and a second composite VLP comprises a composite protein from one or more strains of Norovirus genogroup II. In one embodiment, the first composite VLP comprises a composite protein from one or more strains of Norovirus genogroup I, genotype 1 (GI.1) and a second composite VLP comprises a composite protein from one or more strains of Norovirus genogroup II, genotype 4 (GII.4).

In some embodiments, the vaccine formulation further comprises an adjuvant. Most adjuvants contain a substance designed to protect the antigen from rapid catabolism, such as aluminum hydroxide or mineral oil, and a stimulator of immune responses, such as *Bordatella pertussis* or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); mineral salts, including aluminum salts such as aluminum hydroxide gel (alum) or aluminum phosphate and salts of calcium, iron or zinc; an insoluble suspension of acylated tyrosine acylated sugars; cationically or anionically derivatized polysaccharides; polyphosphazenes; biodegradable microspheres; and Quil A.

Suitable adjuvants also include, but are not limited to, toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, oil-in-water emulsion, MF59, and squalene. In some embodiments, the adjuvants are bacterially-derived exotoxins. In other embodiments, adjuvants which stimulate a Th1 type response, such as 3DMPL or QS21, may be used. In certain embodiments, the adjuvant is a combination of MPL and aluminum hydroxide.

In some embodiments, the adjuvant is monophosphoryl lipid A (MPL). MPL is a non-toxic derivative of lipid A from *Salmonella*, is a potent TLR-4 agonist that has been developed as a vaccine adjuvant (Evans et al. (2003) Expert Rev Vaccines, Vol. 2: 219-229). In pre-clinical murine studies intranasal MPL has been shown to enhance secretory, as well as systemic, humoral responses (Baldridge et al. (2000) Vaccine, Vol. 18: 2416-2425; Yang et al. (2002) Infect Immun., Vol. 70: 3557-3565). It has also been proven to be safe and effective as a vaccine adjuvant in clinical studies of greater than 120,000 patients (Baldrick et al. (2002) Regul Toxicol Pharmacol, Vol. 35: 398-413). MPL stimulates the induction of innate immunity through the TLR-4 receptor and is thus capable of eliciting nonspecific immune responses against a wide range of infectious pathogens, including both gram negative and gram positive bacteria, viruses, and parasites (Persing et al. (2002) Trends Microbiol, Vol. 10: S32-37). Inclusion of MPL in intranasal formulations should provide rapid induction of innate responses, eliciting nonspecific immune responses from viral challenge while enhancing the specific responses generated by the antigenic components of the vaccine. In some embodiments, MPL can be combined with one or more additional adjuvants. For instance, MPL can be combined with aluminum hydroxide to create a suitable adjuvant for intramuscular administration of a vaccine formulation.

In other embodiments, the adjuvant is a naturally occurring oil, such as squalene. Squalene is a triterpenoid hydrocarbon oil ($C_{30}H_{50}$) produced by plants and is present in many foods. Squalene is also produced abundantly by human beings, for whom it serves as a precursor of cholesterol and steroid hormones. It is synthesized in the liver and the skin, transported in the blood by very-low-density lipoproteins (VLDL) and low-density lipoproteins (LDL), and secreted in large amounts by sebaceous glands.

Since it is a natural component of the human body and is biodegradable, squalene has been used as a component of vaccine adjuvants. One of these squalene adjuvants is MF59, an oil-in-water emulsion developed by Chiron. MF59 has been shown in various preclinical and clinical studies to significantly enhance the immune response to a wide variety of vaccine antigens. MF59 is a part of an influenza subunit vaccine, which has been licensed in various European countries since 1997. More than 20 million doses of this vaccine have been given, and it has been shown to have an excellent safety profile. The safety of vaccines with the MF59 adjuvant has also been shown by various investigational clinical studies using recombinant antigens from hepatitis B virus, hepatitis C virus, cytomegalovirus, herpes simplex virus, human immunodeficiency virus, uropathogenic *Escherichia coli*, etc., in various age groups, including 1- to 3-day-old newborns.

The term "effective adjuvant amount" or "effective amount of adjuvant" will be well understood by those skilled in the art, and includes an amount of one or more adjuvants which is capable of stimulating the immune response to an administered antigen, i.e., an amount that increases the immune response of an administered antigen composition, as measured in terms of the IgA levels in the nasal washings, serum IgG or IgM levels, or B and T-Cell proliferation. Suitably effective increases in immunoglobulin levels include by more than 5%, preferably by more than 25%, and in particular by more than 50%, as compared to the same antigen composition without any adjuvant.

In another embodiment of the invention, the vaccine formulation may further comprise a delivery agent, which functions to enhance antigen uptake based upon, but not restricted to, increased fluid viscosity due to the single or combined effect of partial dehydration of host mucopolysaccharides, the physical properties of the delivery agent, or through ionic interactions between the delivery agent and host tissues at the site of exposure, which provides a depot effect. Alternatively, the delivery agent can increase antigen retention time at the site of delivery (e.g., delay expulsion of the antigen). Such a delivery agent may be a bioadhesive agent. In some embodiments, the bioadhesive may be a mucoadhesive agent selected from the group consisting of glycosaminoglycans (e.g., chondroitin sulfate, dermatan sulfate chondroitin, keratan sulfate, heparin, heparan sulfate, hyaluronan), carbohydrate polymers (e.g., pectin, alginate, glycogen, amylase, amylopectin, cellulose, chitin, stachyose, unulin, dextrin, dextran), cross-linked derivatives of poly(acrylic acid), polyvinyl alcohol, polyvinyl pyrollidone, polysaccharides (including mucin, other mucopolysaccharides, and GelSite®, a natural acidic polysaccharide extracted from the aloe plant), polyions, cellulose derivatives (e.g., hydroxypropyl methylcellulose, carboxymethylcellulose), proteins (e.g. lectins, fimbrial proteins), and deoxyribonucleic acid. In one embodiment, the vaccine formulations comprise a polysaccharide such as chitosan, chitosan salt, chitosan base, or a natural polysaccharide (e.g. GelSite®).

Chitosan, a positively charged linear polysaccharide derived from chitin in the shells of crustaceans, is a bioadhesive for epithelial cells and their overlaying mucus layer. Formulation of antigens with chitosan increases their contact time with the nasal membrane, thus increasing uptake by virtue of a depot effect (Illum et al. (2001) Adv Drug Deliv Rev, Vol. 51: 81-96; Illum et al. (2003) J Control Release, Vol. 87: 187-198; Davis et al. (1999) Pharm Sci Technol Today, Vol. 2: 450-456; Bacon et al. (2000) Infect Immun., Vol. 68: 5764-5770; van der Lubben et al. (2001) Adv Drug Deliv Rev, Vol. 52: 139-144; van der Lubben et al. (2001) Eur J Pharm Sci, Vol. 14: 201-207; Lim et al. (2001) AAPS Pharm Sci Tech, Vol. 2: 20). Chitosan has been tested as a nasal delivery system for several vaccines, including influenza, pertussis and diphtheria, in both animal models and humans (Ilium et al. (2001) Adv Drug Deliv Rev, Vol. 51: 81-96; Illum et al. (2003) J Control Release, Vol. 87: 187-198; Bacon et al. (2000) Infect Immun., Vol. 68: 5764-5770; Jabbal-Gill et al. (1998) Vaccine, Vol. 16: 2039-2046; Mills et al. (2003) A Infect Immun, Vol. 71: 726-732; McNeela et al. (2004) Vaccine, Vol. 22: 909-914). In these trials, chitosan was shown to enhance systemic immune responses to levels equivalent to parenteral vaccination. In addition, significant antigen-specific IgA levels were also measured in mucosal secretions. Thus, chitosan can greatly enhance a nasal vaccine's effectiveness. Moreover, due to its physical characteristics, chitosan is particularly well suited to intranasal vaccines formulated as powders (van der Lubben et al. (2001) Eur J Pharm Sci, Vol. 14: 201-207; Mikszta et al. (2005) J Infect Dis, Vol. 191: 278-288; Huang et al. (2004) Vaccine, Vol. 23: 794-801).

In another embodiment of the invention, the vaccine formulation may further comprise a pharmaceutically acceptable carrier. A pharmaceutically acceptable carrier, including any suitable diluent or excipient, includes any pharmaceutical agent that does not itself induce the production of an immune response harmful to the subject receiving the vaccine formulation, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. Pharmaceutically acceptable carriers include, but are not limited to, saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably the formulation is sterile, non-particulate and/or non-pyrogenic. The vaccine formulation, if desired, can also contain minor amounts of wetting or emulsifying agents, or pH buffering agents.

In some embodiments of the present invention, among others, vaccine formulations comprise chitosan, a chitosan salt, or a chitosan base. The molecular weight of the chitosan may be between 10 kDa and 800 kDa, preferably between 100 kDa and 700 kDa and more preferably between 200 kDa and 600 kDa. The concentration of chitosan in the composition will typically be up to about 80% (w/w), for example, 5%, 10%, 30%, 50%, 70% or 80%. The chitosan is one which is preferably at least 75% deacetylated, for example 80-90%, more preferably 82-88% deacetylated, particular examples being 83%, 84%, 85%, 86% and 87% deacetylation.

The compositions of the invention can be formulated for administration as vaccines or antigenic formulations. As used herein, the term "vaccine" refers to a formulation which contains VLPs or other antigens of the present invention as described above, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs or antigen. As used herein, the term "antigenic formulation" or "antigenic composition" refers to a preparation which, when administered to a vertebrate, e.g. a mammal, will induce an immune response. As used herein, the term "immune response" refers to both the humoral immune response and the cell-mediated immune response. The humoral immune response involves the stimulation of the production of antibodies by B lymphocytes that, for example, neutralize infectious agents, block infectious agents from entering cells, block replication of said infectious agents, and/or protect host cells from infection and destruction. The cell-mediated immune response refers to an immune response that is mediated by T-lymphocytes and/or other cells, such as macrophages, against an infectious agent, exhibited by a vertebrate (e.g., a human), that prevents or ameliorates infection or reduces at least one symptom thereof. In particular, "protective immunity" or "protective immune response" refers to immunity or eliciting an immune response against an infectious agent, which is exhibited by a vertebrate (e.g., a human), that prevents or ameliorates an infection or reduces at least one symptom thereof. Specifically, induction of a protective immune response from administration of the vaccine is evident by elimination or reduction of the presence of one or more symptoms of gastroenteritis or a reduction in the duration or severity of such symptoms. Clinical symptoms of gastroenteritis from Norovirus include nausea, diarrhea, loose stool, vomiting, fever, and general malaise. A protective immune response that reduces or eliminates disease symptoms will reduce or stop the spread of a Norovirus outbreak in a population. Vaccine preparation is generally described in Vaccine Design ("The subunit and adjuvant approach" (eds Powell M. F. & Newman M. J.) (1995) Plenum Press New York). The compositions of the present invention can be formulated, for example, for administration to a subject by mucosal or parenteral (e.g. intramuscular, intravenous, subcutaneous, intradermal, subdermal, or transdermal) routes of administration. Such mucosal administration could be, but is not limited to, through gastro-intestinal, intranasal, oral, or vaginal delivery. In one embodiment, the vaccine formulation is in the form of a nasal spray, nasal drops or dry powder. In another embodiment, the vaccine formulation is in a form suitable for intramuscular administration.

Vaccine formulations of the invention may be liquid formulations or dry powder formulations. Where the composition is intended for delivery to the respiratory (e.g. nasal) mucosa, typically it is formulated as an aqueous solution for administration as an aerosol or nasal drops, or alternatively, as a dry powder, e.g. for rapid deposition within the nasal passage. Compositions for administration as nasal drops may contain one or more excipients of the type usually included in such compositions, for example preservatives, viscosity adjusting agents, tonicity adjusting agents, buffering agents, and the like. Viscosity agents can be microcrystalline cellulose, chitosan, starches, polysaccharides, and the like. Compositions for administration as dry powder may also contain one or more excipients usually included in such compositions, for example, mucoadhesive agents, bulking agents, and agents to deliver appropriate powder flow and size characteristics. Bulking and powder flow and size agents may include mannitol, sucrose, trehalose, and xylitol.

In one embodiment, the vaccine formulation contains one or more composite VLPs as the immunogen, an adjuvant such as MPL®, squalene, or MF59®, a biopolymer such as chitosan or GelSite® to promote adhesion to mucosal surfaces, and bulking agents such as mannitol and sucrose.

For example, a vaccine may be formulated as 10 mg of a dry powder containing one or more composite VPLs as discussed herein, such as the GII.4 composite VPL, MPL® adjuvant, chitosan mucoadhesive, and mannitol and sucrose as bulking agents and to provide proper flow characteristics. The formulation may comprise about 7.0 mg (25 to 90% w/w range) chitosan, about 1.5 mg mannitol (0 to 50% w/w range), about 1.5 mg sucrose (0 to 50% w/w range), about 25 µg MPL® (0.1 to 5% w/w range), and about 100 µg composite VLP antigen (0.05 to 5% w/w range).

Composite VLPs/antigens may be present in a concentration of from about 0.01% (w/w) to about 80% (w/w). In one embodiment, VLPs can be formulated at dosages of about 5 µg, about 15 µg, about 25 µg, about 50 µg, about 100 µg, about 200 about 500 µg, and about 1 mg per 10 mg dry powder formulation (0.05, 0.15, 0.25, 0.5, 1.0, 2.0, 5.0, and 10.0% w/w) for administration into both nostrils (10 mg per nostril) or about 10 µg, about 30 µg, about 50 µg, about 100 µg, about 200 µg, about 400 µg, about 1 mg, and about 2 mgs (0.1, 0.3, 0.5, 1.0, 2.0, 4.0, 10.0 and 20.0% w/w) per 20 mg dry powder formulation for administration into one nostril. The formulation may be given in one or both nostrils during each administration. There may be a booster administration 1 to 12 weeks after the first administration to improve the immune response. The content of each VLP/antigen in the vaccine and antigenic formulations may be in the range of 1 µg to 100 mg, preferably in the range 1-1000 µg, more preferably 5-500 µb, most typically in the range 10-200 µg. Total VLP/antigen administered at each dose can be either about 10 µg, about 30 µg, about 200 µg, about 250 µg, about 400 µg, about 500 µg, or about 1000 µg. The total vaccine dose can be administered into one nostril or can be split in half for administration to both nostrils. Dry powder characteristics are such that less than 10% of the particles are less than 10 µm in diameter. Mean particle sizes range from 10 to 500 µm in diameter.

In another embodiment of the invention, the dry powder formulation may be in combination with one or more devices for administering one or more doses of the formulation. Such a device may be a single-use nasal administrative device. In another embodiment, one or more doses are unit doses.

In some embodiments, the antigenic and vaccine formulations are liquid formulations for subsequent administration to a subject. A liquid formulation intended for intranasal administration would comprise composite VLP/antigen(s), adjuvant, and a delivery agent such as chitosan. Liquid formulations for parenteral (e.g., subcutaneous, intradermal, or intramuscular (i.m.)) administration would comprise composite VLP/antigen(s), adjuvant, and a buffer, without a delivery agent (e.g., chitosan).

Preferably the antigenic and vaccine formulations hereinbefore described are lyophilized and stored anhydrous until they are ready to be used, at which point they are reconstituted with diluent. Alternatively, different components of the composition may be stored separately in a kit (any or all components being lyophilized). The components may remain in lyophilized form for dry formulation or be reconstituted for liquid formulations, and either mixed prior to use or administered separately to the patient. For dry powder administration, the vaccine or antigenic formulation may be preloaded into an intranasal delivery device and stored until use. Preferably, such intranasal delivery device would protect and ensure the stability of its contents.

The invention also encompasses compositions comprising one or more of the immunogenic nucleic acids, polypeptides, and/or VLPs, described herein. Different polypeptides, including composite polypeptides and capsid polypeptides or fragments thereof may be mixed together in a single formulation. Within such combinations, an antigen of the immunogenic composition may be present in more than one polypeptide, or multiple epitope polypeptide.

The immunogenic compositions may comprise a mixture of composite polypeptides and nucleic acids encoding composite polypeptides, which in turn may be delivered using the same or different vehicles. Antigens may be administered individually or in combination, in e.g., prophylactic (i.e., to prevent infection) or therapeutic (to treat infection) immunogenic compositions. The immunogenic composition may be given more than once (e.g., a "prime" administration followed by one or more "boosts") to achieve the desired effects. The same composition can be administered in one or more priming and one or more boosting steps. Alternatively, different compositions can be used for priming and boosting.

The present invention also contemplates a method of inducing protective immunity to a viral infection in a subject comprising administering any of the vaccine formulations described herein. In one embodiment, the viral infection is a Norovirus infection. In another embodiment, the vaccine formulation confers protection from one or more symptoms of Norovirus infection.

The present invention also provides a method for making a VLP comprising a composite polypeptide. In one embodiment, the method comprises aligning amino acid sequences of capsid proteins from two or more circulating strains of a non-enveloped virus; determining a consensus sequence from said aligned amino acid sequences; preparing a composite sequence based on said consensus sequence that contains at least one different amino acid as compared to each of the capsid sequences of said two or more circulating strains; and expressing said composite sequence in a host cell, thereby producing a virus-like particle. In another embodiment, the composite sequence contains at least three different amino acids as compared to each of the capsid sequences of said two or more circulating strains. In another embodiment, the composite sequence contains at least five different amino acids as compared to each of the capsid sequences of said two or more circulating strains. In yet another embodiment, the composite sequence contains at least nine different amino acids as compared to each of the capsid sequences of said two or more circulating strains. In some embodiments, the consensus sequence may be determined from aligning nucleotide sequences of capsid proteins from two or more circulating strains of a non-enveloped virus; and preparing a composite nucleotide sequence based on said consensus sequence. Non-limiting examples of a non-enveloped virus suitable for use in the method are Calicivirus, Picornavirus, Astrovirus, Adenovirus, Reovirus, Polyomavirus, Papillomavirus, Parvovirus, and Hepatitis E virus. In some embodiments, the non-enveloped virus is a Calicivirus. The Calicivirus may be a Norovirus or Sapovirus. In another embodiment, the Norovirus is a genogroup I or genogroup II Norovirus.

The invention will now be illustrated in greater detail by reference to the specific embodiments described in the following examples. The examples are intended to be purely illustrative of the invention and are not intended to limit its scope in any way.

EXAMPLES

Example 1

Design of a Norovirus GII.4 Consensus Gene

A consensus amino acid sequence for the major capsid protein (VP1) of genogroup II, genotype 4 (GII.4) Norovirus was determined by homology comparison of two recently circulating GII.4 Strains, Minerva, AKA 2006-b, DenHaag, and GenBank Sequence ABL74395; and Laurens, AKA 2006-a, Yerseke, and GenBank Sequence ABL74391, with a GII.4 Houston strain, GenBank Sequence ABY27560, obtained in 2002. The alignment of the three different Norovirus GII.4 isolates is shown below. The consensus sequence (SEQ ID NO: 2) determined from the homology comparison of the three GII.4 strains is shown in FIG. 1.

A composite sequence was derived from the consensus sequence by selecting amino acids from the Laurens sequence in variable positions of the consensus sequence where all three strains differed. The chosen amino acids were present in antigenic regions near to but not including the proposed carbohydrate binding domain. The composite GII.4 sequence was used for the production of a synthetic gene encoding a composite GII.4 Norovirus VP1 protein (SEQ ID NO: 1). The GII.4 composite VP1 amino acid sequence (GII.4 Comp) is shown in the alignment below as SEQ ID NO: 1 with the amino acid sequences of the VP1 proteins from Houston, Laurens, and Minerva virus (SEQ ID NOs: 4, 5, and 6, respectively). The DNA sequence encoding the GII.4 composite VP1 (SEQ ID NO: 3) is shown in FIG. 2.

```
Houston    MKMASSDASPSDGSTANLVPEVNNEVMALEPVVGAAIAAPVAGQQNVIDPWIR 53
Laurens    MKMASSDANPSDGSTANLVPEVNNEVMALEPVVGAAIAAPVAGQQNVIDPWIR 53
Minerva    MKMASNDANPSDGSAANLVPEVNNEVMALEPVVGAAIAAPVAGQQNVIDPWIR 53
GII.4 Comp MKMASSDANPSDGSTANLVPEVNNEVMALEPVVGAAIAAPVAGQQNVIDPWIR 53

Houston    NNFVQAPGGEFTVSPRNAPGEILWSAPLGPDLNPYLSHLARMYNGYAGGFEVQ 106
Laurens    NNFVQAPGGEFTVSPRNAPGEILWSAPLGPDLNPYLSHLARMYNGYAGGFEVQ 106
Minerva    NNFVQAPGGEFTVSPRNAPGEILWSAPLGPDLNPYLSHLARMYNGYAGGFEVQ 106
GII.4 Comp NNFVQAPGGEFTVSPRNAPGEILWSAPLGPDLNPYLSHLARMYNGYAGGFEVQ 106
```

-continued

```
    Houston VILAGNAFTAGKIIFAAVPPNFPTEGLSPSQVTMFPHIIVDVRQLEPVLIPLP 159
    Laurens VILAGNAFTAGKIIFAAVPPNFPTEGLSPSQVTMFPHIIVDVRQLEPVLIPLP 159
    Minerva VILAGNAFTAGKIIFAAVPPNFPTEGLSPSQVTMFPHIIVDVRQLEPVLIPLP 159
GII.4 Comp VILAGNAFTAGKIIFAAVPPNFPTEGLSPSQVTMFPHIIVDVRQLEPVLIPLP 159

Houston DVRNNFYHYNQSNDPTIKLIAMLYTPLRANNAGDDVFTVSCRVLTRPSPDFDF 212
    Laurens DVRNNFYHYNQSNDPTIKLIAMLYTPLRANNAGDDVFTVSCRVLTRPSPDFDF 212
    Minerva DVRNNFYHYNQSNDSTIKLIAMLYTPLRANNAGEDVFTVSCRVLTRPSPDFDF 212
GII.4 Comp DVRNNFYHYNQSNDPTIKLIAMLYTPLRANNAGDDVFTVSCRVLTRPSPDFDF 212

Houston IFLVPPTVESRTKPFTVPILTVEEMTNSRFPIPLEKLFTGPSGAFVVQPQNGR 265
    Laurens IFLVPPTVESRTKPFSVPILTVEEMTNSRFPIPLEKLFTGPSSAFVVQPQNGR 265
    Minerva IFLVPPTVESRTKPFTVPILTVEEMTNSRFPIPLEKLFTGPSGAFVVQPQNGR 265
GII.4 Comp IFLVPPTVESRTKPFTVPILTVEEMTNSRFPIPLEKLFTGPSGAFVVQPQNGR 265

Houston CTTDGVLLGTTQLSPVNICTFRGDVTHIAGTHDYTMNLASQNWNNYDPTEEIP 318
    Laurens CTTDGVLLGTTQLSPVNICTFRGDVTHIAGTQEYTMNLASQNWNNYDPTEEIP 318
    Minerva CTTDGVLLGTTQLSPVNICTFRGDVTHIAGSRNYTMNLASLNWNNYDPTEEIP 318
GII.4 Comp CTTDGVLLGTTQLSPVNICTFRGDVTHIAGTQEYTMNLASQNWNNYDPTEEIP 318

Houston APLGTPDFVGKIQGVLTQTTRGDGSTRGHKATVSTGSVHFTPKLGSVQFTTDT 371
    Laurens APLGTPDFVGKIQGVLTQTTRRDGSTRGHKATVSTGSVHFTPKLGRIQFSTDT 371
    Minerva APLGTPDFVGKIQGVLTQTTKGDGSTRGHKATVYTGSAPFTPKLGSVQFSTDT 371
GII.4 Comp APLGTPDFVGKIQGVLTQTTRGDGSTRGHKATVSTGSVHFTPKLGSVQFSTDT 371

Houston NNDLETGQNTKFTPVGVVQDGNSAHQNEPQQWVLPNYSGRTGHNVHLAPAVAP 424
    Laurens SNDFETGQNTRFTPVGVVQDGSTTHQNEPQQWVLPDYSGRDSHNVHLAPAVAP 424
    Minerva ENDFETHQNTKFTPVGVIQDGSTTHRNEPQQWVLPSYSGRNVHNVHLAPAVAP 424
GII.4 Comp SNDFETGQNTKFTPVGVVQDGSTTHQNEPQQWVLPDYSGRDSHNVHLAPAVAP 424

Houston TFPGEQLLFFRSTMPGCSGYPNMNLDCLLPQEWVLHFYQEAAPAQSDVALLRF 477
    Laurens SFPGEQLLFFRSTMPGCSGYPNMNLDCLLPQEWVQHFYQEAAPAQSDVALLRF 477
    Minerva TFPGEQLLFFRSTMPGCSGYPNMDLDCLLPQEWVQHFYQEAAPAQSDVALLRF 477
GII.4 Comp TFPGEQLLFFRSTMPGCSGYPNMNLDCLLPQEWVQHFYQEAAPAQSDVALLRF 477

Houston VNPDTGRVLFECKLHKSGYVTVAHTGPHDLVIPPNGYFRFDSWVNQFYTLAPM 530
    Laurens VNPDTGRVLFECKLHKSGYVTVAHTGQHDLVIPPNGYFRFDSWVNQFYTLAPM 530
    Minerva VNPDTGRVLFECKLHKSGYVTVAHTGQHDLVIPPNGYFRFDSWVNQFYTLAPM 530
GII.4 Comp VNPDTGRVLFECKLHKSGYVTVAHTGQHDLVIPPNGYFRFDSWVNQFYTLAPM 530

Houston GNGAGRRRA (SEQ ID NO: 4)                               539
    Laurens GNGTGRRRA (SEQ ID NO: 5)                               539
    Minerva GNGTGRRRA (SEQ ID NO: 6)                               539
GII.4 Comp GNGTGRRRA (SEQ ID NO: 1)                               539
```

Example 2

Purification of Composite VLPs

Synthetic gene construct of Norovirus GII.4 composite sequence for capsid domains described in Example 1 was cloned into recombinant Baculovirus. Infection of insect cells demonstrated high yield of production of VLP. A 40 mL aliquot of a P2 pFastBac recombinant baculovirus stock for the composite VLP VP1 gene was processed with a sucrose gradient to verify the expression and assembly of composite VLPs. The conditioned media was first layered onto a 30% sucrose cushion and then centrifuged at 140 K×g to pellet the VLP. The pellet was resuspended, layered onto a sucrose gradient and then centrifuged at 140 K×g. A visible white layer was observed within the gradient after centrifugation. 500 µL fractions from the gradient were collected and then analyzed by SDS-PAGE/Coomassie gel (FIG. 3). The expected banding pattern for composite VLP at ~56 kDa was observed within the sucrose gradient fractions.

Figure 4:
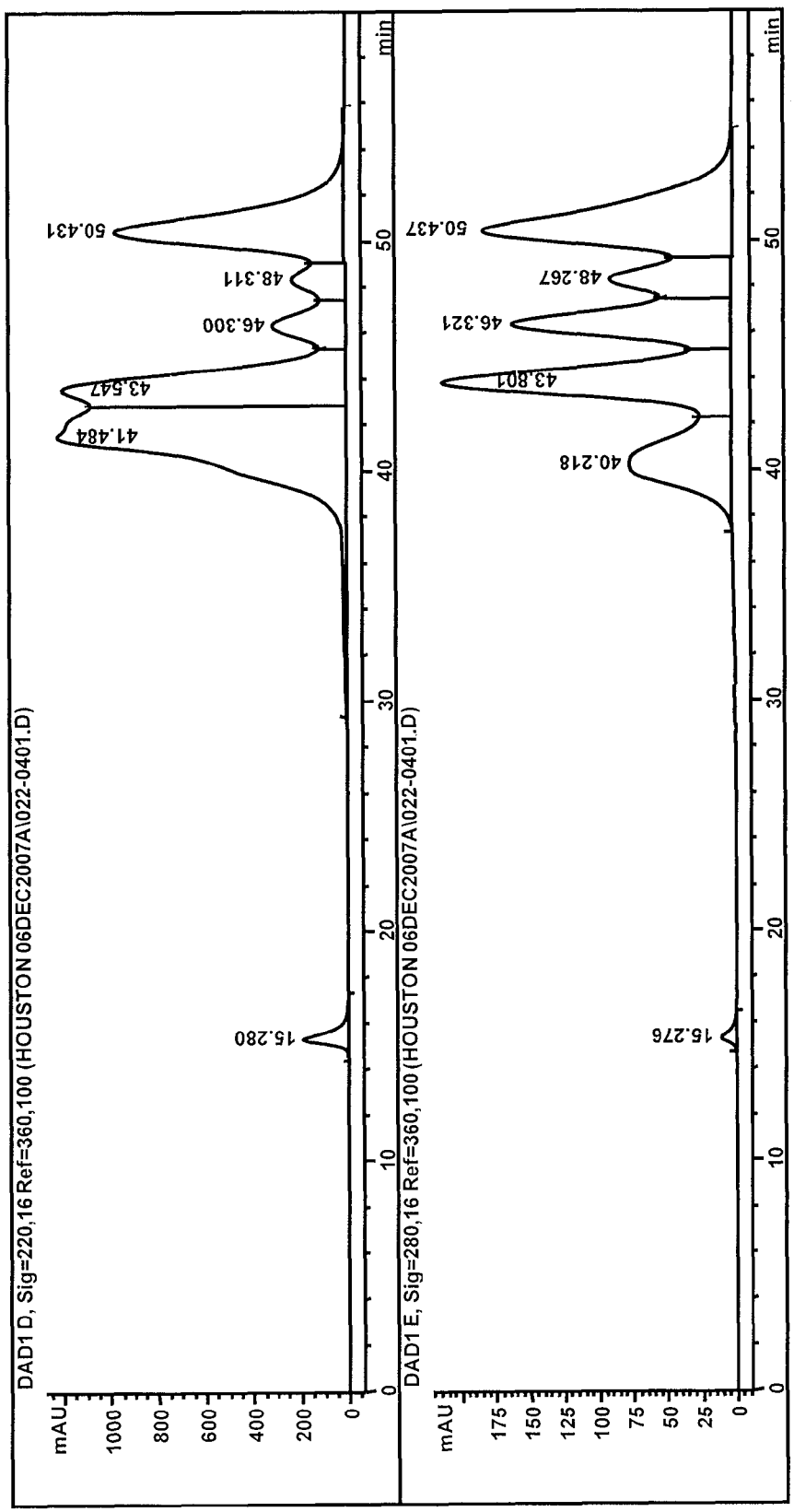
FIG. 4. HPLC SEC chromatogram of readings at 220 nm (top) and 280 nm (bottom) of composite expression cell culture supernatant purified by sucrose gradient.

Using a high pressure liquid chromatography system with a running buffer of 20 mM Tris 150 mM NaCl pH 7 at a flow rate of 0.5 mL/minute, a 50 µL aliquot of the composite expression cell culture supernatant was loaded on to a Superose-6 size exclusion column. An intact VLP peak was observed at ~15.3 minutes at 280 nm and 220 nm confirming integrity of the composite VLPs (FIG. 4).

Figure 5:
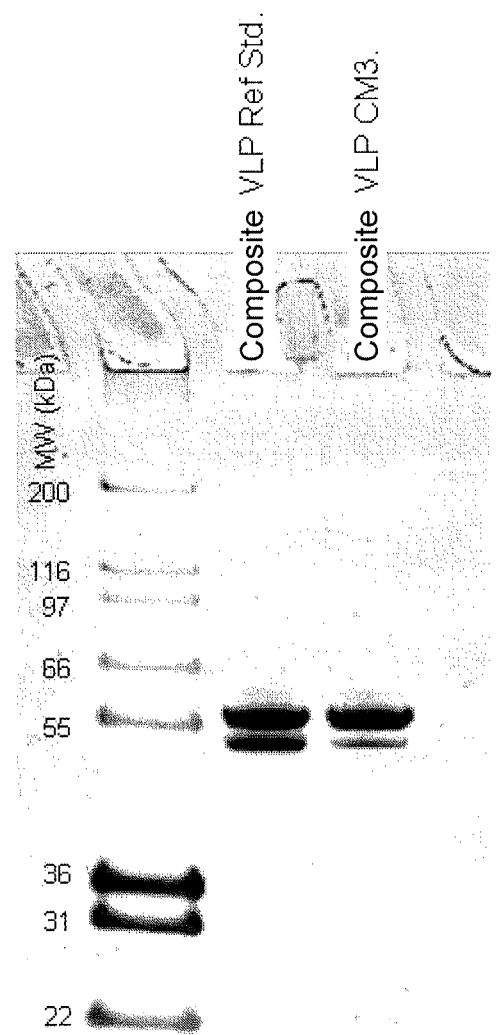
FIG. 5. SDS-PAGE/Silver-stain analysis of composite sequence VLPs purified by column chromatography.

Composite VLPs were also purified from conditioned media using column chromatography. Conditioned media was processed by cation exchange chromatography. The cation exchange elution fraction was further purified by hydrophobic interaction chromatography (HIC). The HIC elution fraction was concentrated and buffer exchanged by tangential flow filtration. The final product was sterile filtered and stored at 4° C. 500 ng of the purified composite VLPs (CM3 lot) was analyzed by silver-stained SDS-PAGE (FIG. 5).

Figure 6:
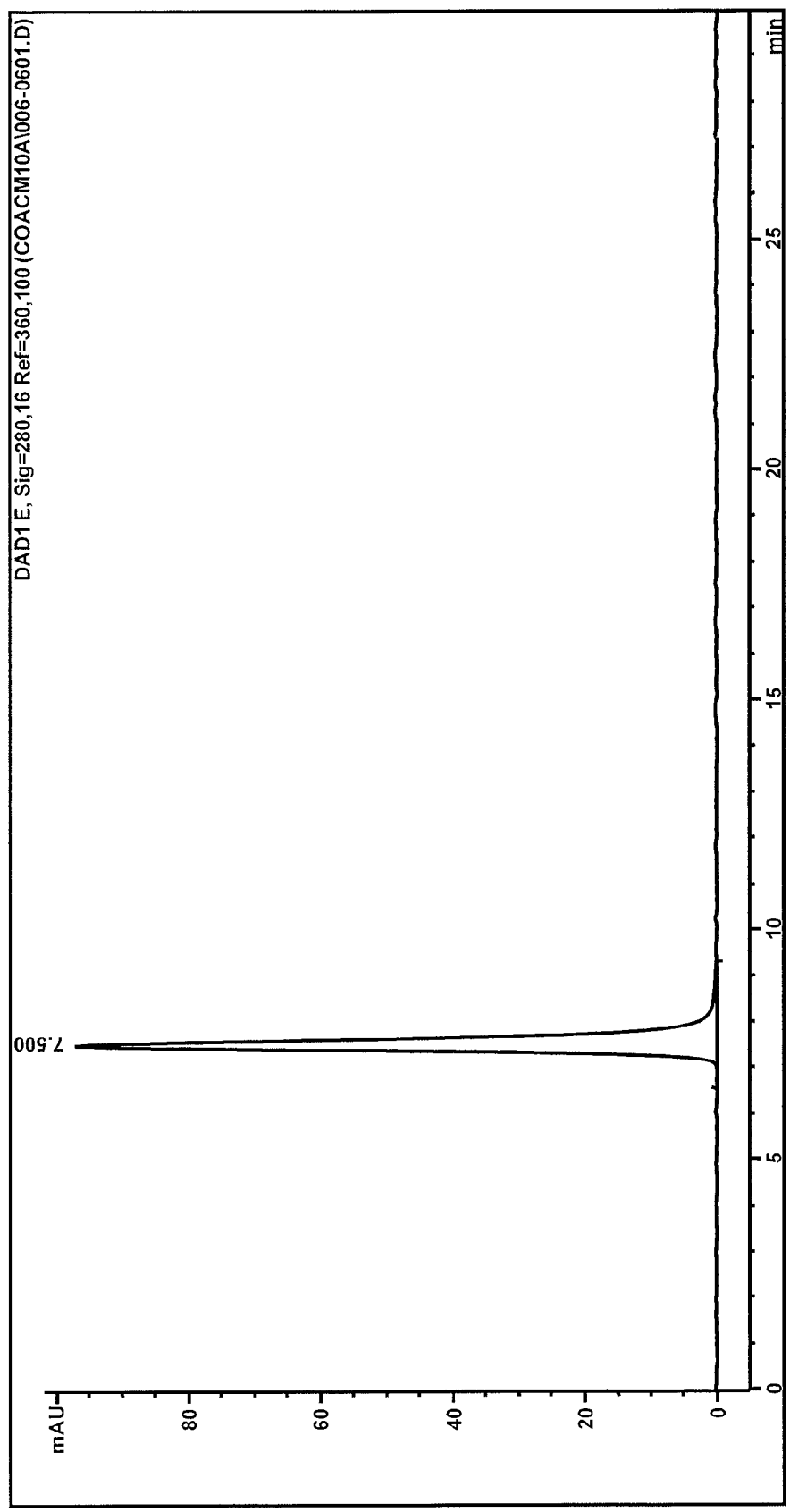
FIG. 6. HPLC SEC chromatogram of readings at 280 nm of composite VLPs.

Using a high pressure liquid chromatography system with a running buffer of 20 mM Tris 150 mM NaCl pH 7 at a flow rate of 1.0 mL/minute, a 50 µL aliquot of the purified CM3 composite VLPs was loaded on to a Superose-6 size exclusion column. An intact VLP peak was observed at ~7.5 minutes at 280 nm confirming integrity of the composite VLPs (FIG. 6).

Example 3

Composite Immunogenicity

Figure 7:
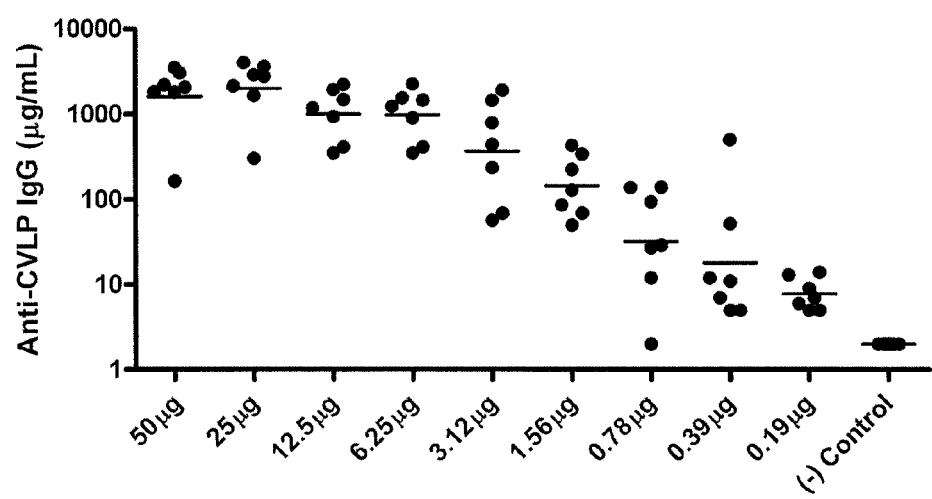
FIG. 7. Immunization with composite VLP (CVLP) elicits antigen-specific IgG. Groups of 7 mice were immunized (i.p.) with various concentrations of CVLP (indicated on the X axis) on days 0 and 7. Serum was collected on day 14 and CVLP-specific IgG was measured by ELISA. Horizontal lines indicate geometric means of each treatment group.

Female C57BL/6 mice approximately 8-10 weeks of age were immunized intraperitoneally with decreasing concentrations of composite VLP (CVLP) starting with 50 µg and decreasing 2 fold to 0.19 µg. The CVLP contained a polypeptide having the sequence of SEQ ID NO: 1 as described in Example 1. A group of animals immunized with PBS alone was included as a negative control. Serum samples were collected and analyzed for the presence of CVLP-specific IgG by ELISA (FIG. 7). The results from this experiment indicate that the linear range of the dose curve is between approximately 6 µg and 0.2 µg. Doses above 6.25 µg of CVLP do not appear to enhance immune responses in a dose-dependent manner. The $EC_{50}$ value (defined as the effective dose yielding a 50% response) was calculated to be approximately 1.0 µg/mL using Softmax Pro software (Molecular Devices Corporation, Sunnyvale, Calif.).

Example 4

Multiple Antigen Effect of Composite VLPs

Figure 8:
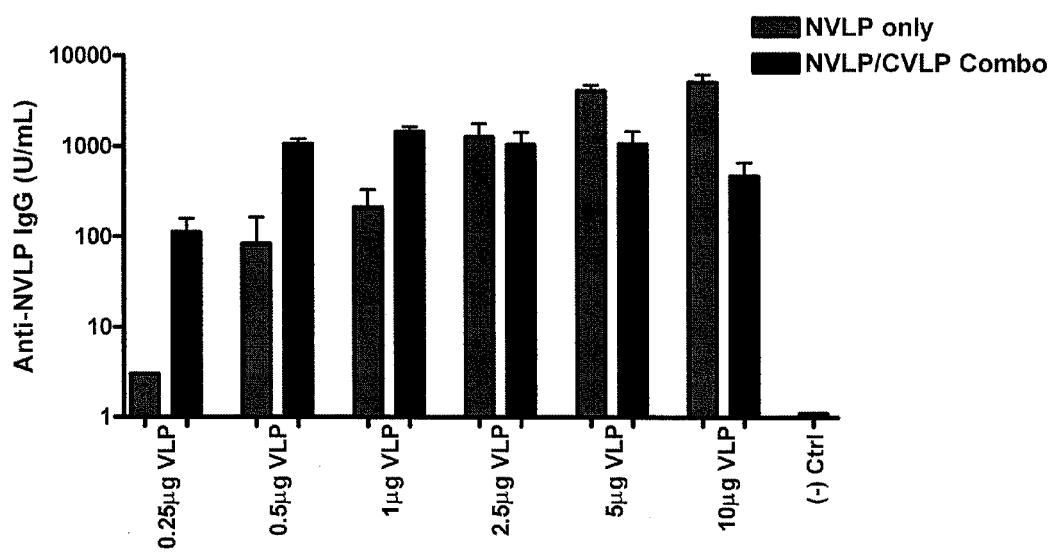
FIG. 8. Immunization with composite VLP/Norwalk VLP (CVLP/NVLP) combination elicits NVLP-specific IgG. Groups of 7 mice were immunized (i.p.) with various concentrations of NVLP alone (purple bars) or in combination with equal amounts of CVLP (black bars) on days 0 and 14. Serum was collected on day 21 and NVLP-specific IgG was measured by ELISA. Data is reported as the mean+standard error of the mean (SEM).
Figure 9:
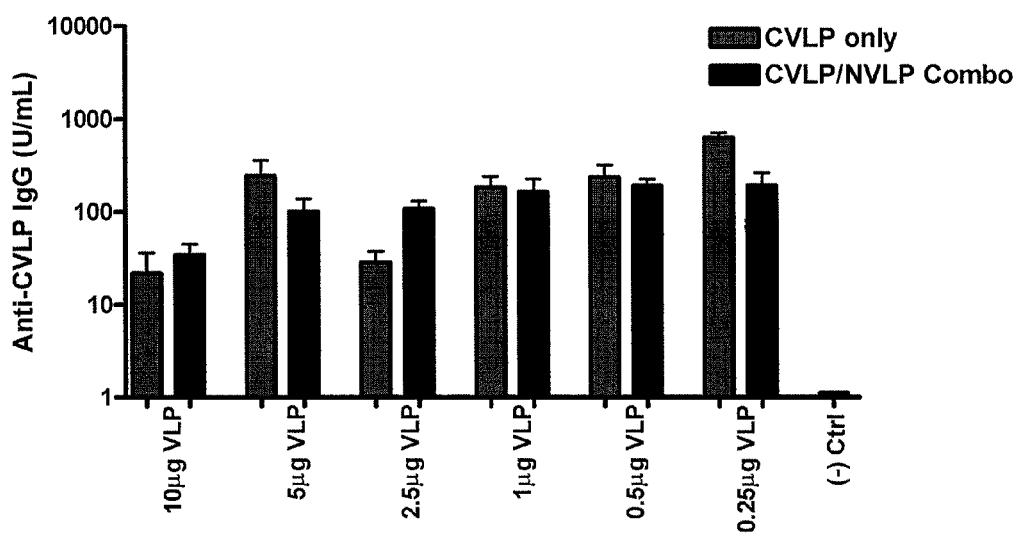
FIG. 9. Immunization with composite VLP/Norwalk VLP (CVLP/NVLP) combination elicits CVLP-specific IgG. Groups of 7 mice were immunized (i.p.) with various concentrations of either composite VLP alone (green bars) or in combination with equal amounts of NVLP (black bars) on days 0 and 14. Serum was collected on day 21 and CVLP-specific IgG was measured by ELISA. Data is reported as the mean+standard error of the mean (SEM).

Female C57BL/6 mice (8-10 weeks of age) were immunized intraperitoneally with varying doses of either Norwalk VLP alone (NVLP), composite VLP (CVLP) alone or in combination. A group of animals immunized with PBS alone was included as a negative control. Serum samples were collected and analyzed for the presence of antigen-specific IgG by ELISA (FIGS. 8 and 9). The results indicate that immunizing with the combination of the CVLP and NVLP enhances the immune response such that a higher IgG level is achieved with a lower dose of antigen. For example, immunizing with 1 µg of each NVLP and CVLP elicits a more robust immune response then administering with either VLP alone. The antibodies from animals immunized with CVLP did not cross-react with NVLP and vise versa (data not shown).

Example 5

Composite VLPs Elicit Cross-Reactivite Antibodies

Figure 10:
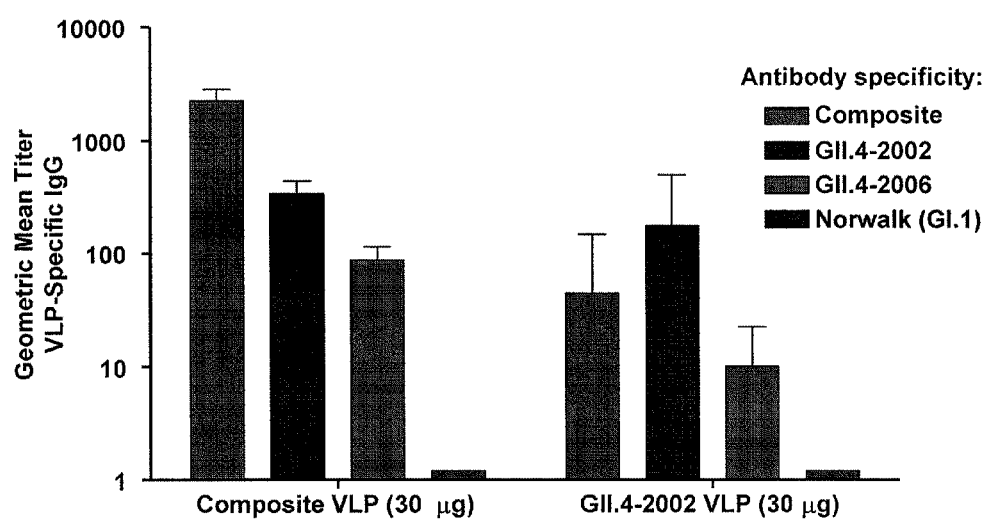
FIG. 10. CVLP-specific IgG cross-reacts with other Norovirus isolates. Antibody titers measured 21 days after a single immunization with the either Composite VLPs or GII.4 2002 VLPs show that Composite VLPs elicit~10 fold higher titers as compared to the GII.4 2002 VLPs. Antibody titers for animals immunized with all GII.4 VLPs show poor cross reactivity to GI.1 VLPs. Data are expressed as geometric mean+standard error of the mean (SEM).

Female C57/BL6 mice, approximately 10-12 weeks of age, were immunized intraperitoneally with either 30 µg Houston VLPs or composite VLPs formulated with MPL (20 µg) as an adjuvant. The composite VLPs contained a polypeptide having the sequence of SEQ ID NO: 1 as described in Example 1. The mice were bled on day 21 following immunization and the sera were assayed in an antigen-specific ELISA to determine antibody titers for composite, Houston, Laurens, and Norwalk VLPs. The data are shown in FIG. 10. Immunization with composite VLP induces a broader response across more serotypes as evidenced by the greater response to the Laurens strain while maintaining response to the Houston strain. Immunization with Houston VLPs also induces cross-reactive antibodies against composite and Laurens but the magnitude of the response is not as great as that observed with immunization with the composite VLPs. There was no detectable response to Norwalk VLP, which is a GI.1 Norovirus.

Example 6

Efficacy of Bivalent Vaccine in Rabbits

A study was performed to evaluate the efficacy of a bivalent Norovirus vaccine comprising Norovirus GII.4 composite VLPs (CVLPS) as described in Example 2 and Norwalk VLPs (NVLPs, GI.1). Rabbits were intramuscularly immunized with this bivalent vaccine on days 0 and 21. VLP doses ranged from 20 µg to 0.002 µg of each type of VLP and each vaccine formulation contained 25 µg MPL and 250 µg AlOH. Serum was collected from each rabbit on day 28 and VLP-specific IgG was evaluated. Spleens and mesenteric lymph nodes were collected on day 75 and evaluated for the presence antigen-specific cellular immunity.

Figure 11:
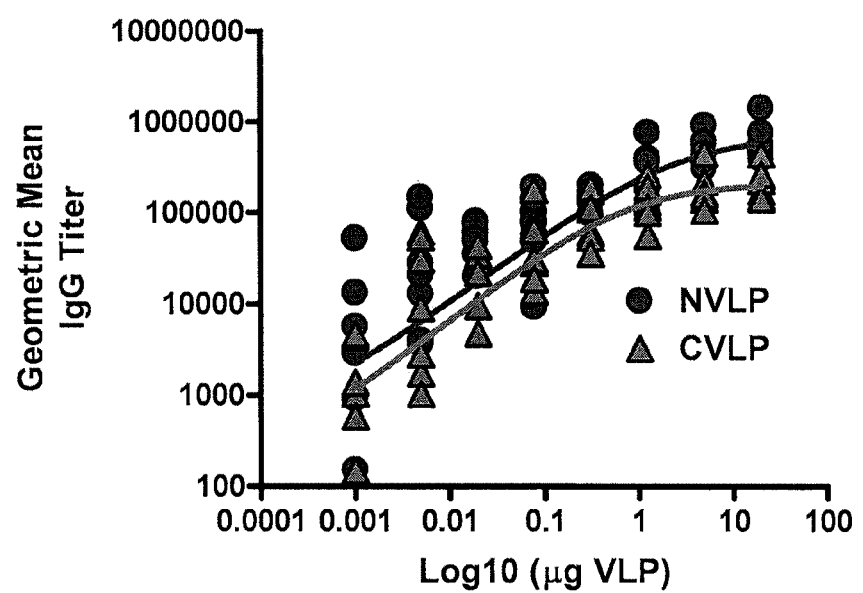
FIG. 11. Rabbits were immunized IM on day 0 and 21 with equal amounts of Norwalk VLP (NVLP) and composite VLP (CVLP). Serum was collected on day 28 and VLP-specific IgG was evaluated. The resulting data was log transformed and evaluated by linear regression analysis. IgG titers are expressed as reciprocal dilutions and shown as geometric mean titers.
Figure 12:
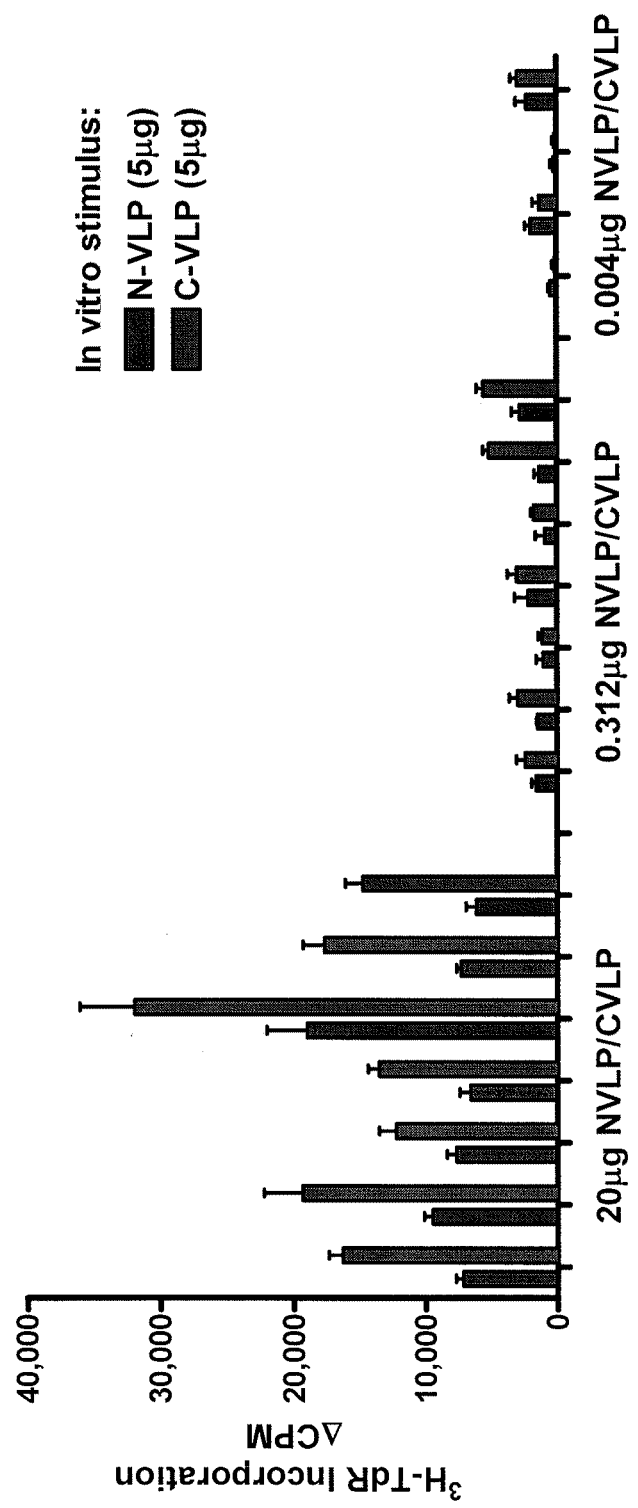
FIG. 12. Rabbits were immunized IM on day 0 and 21 with equal amounts of Norwalk VLP (NVLP) and composite VLP (CVLP). Spleens were collected on day 75 and unfractionated cells were stimulated in culture for 5 days with either NVLP or CVLP and the amount of thymidine incorporation was measured. The mean and SD are shown for each rabbit in the treatment groups indicated on the X axis. Data are expressed as mean+SD.
Figure 13:
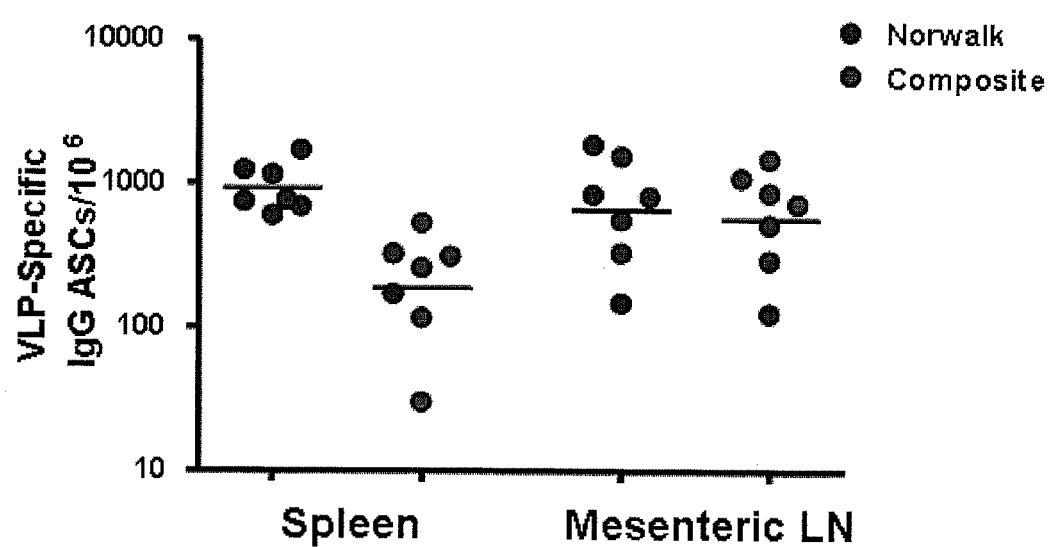
FIG. 13. Rabbits were immunized IM on day 0 and 21 with equal amounts of Norwalk VLP (NVLP) and composite VLP (CVLP). Spleens and mesenteric lymph nodes (LN) were collected on day 75 and analyzed for the presence of VLP-specific memory B-cells by ELISPOT. Individual responses are shown for NVLP and CVLP. Data are represented as the number of VLP-specific IgG secreting cells per million cells present.

Serum IgG titers were measured by ELISA using microtiter plates coated with either NVLP or CVLP as a capture. Titers are expressed as reciprocal dilutions (FIG. 11). Antigen-specific T-cell responsiveness was evaluated by tritiated thymidine incorporation after a 5-day in vitro stimulation with 5 µg of either NVLP or CVLP (FIG. 12). Memory B-cells were evaluated by VLP-specific ELISPOT and results are expressed as antibody-secreting cells per million cells (FIG. 13).

The results of this study demonstrate that the IM bivalent norovirus vaccine formulated with the adjuvants MPL and AlOH elicits high VLP-specific IgG responses, responsive T-cells and memory B-cells capable of responding to stimulation with both NVLP and CVLP.

Example 7

High-Dose Bivalent Vaccination in Rabbits

Figure 14:
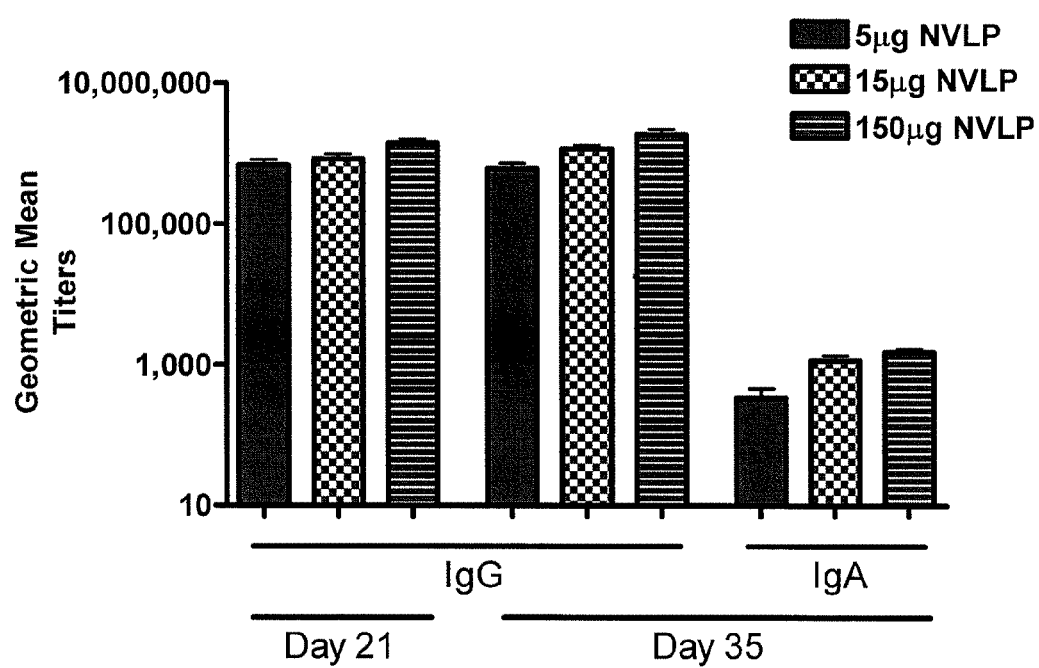
FIG. 14. Rabbits were immunized IM on days 0, 14, and 21 with equal amounts of Norwalk VLP (NVLP) and composite VLP (CVLP) as indicated in the legend. Serum was collected on day 21 and 35 and NVLP-specific IgG and IgA was measured by ELISA. Results are displayed as geometric group means+SEM.
Figure 15:
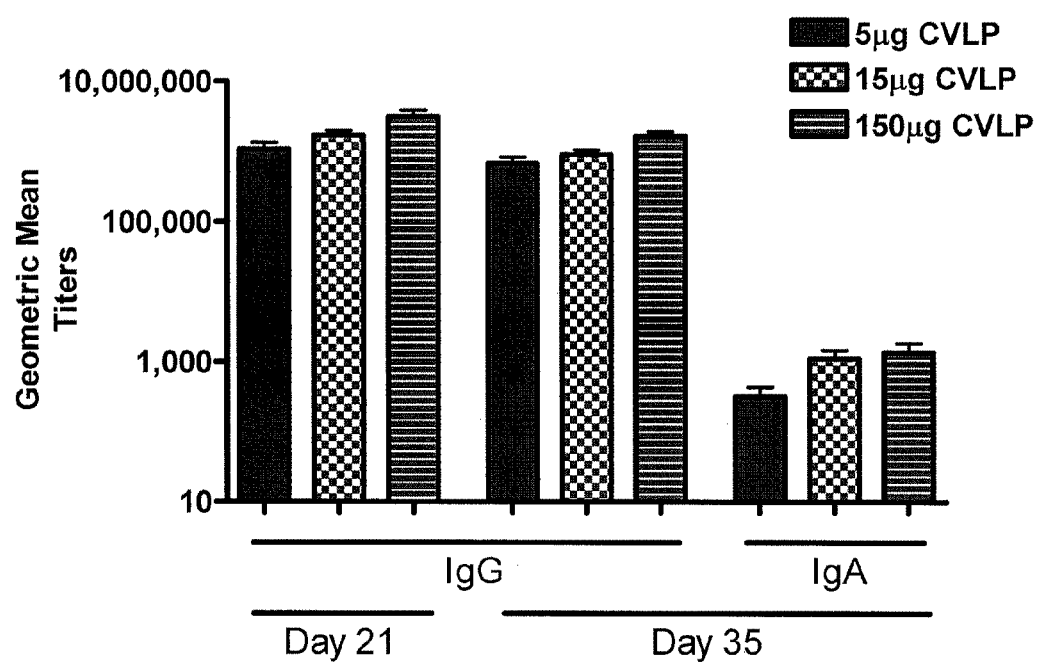
FIG. 15. Rabbits were immunized IM on days 0, 14, and 21 with equal amounts of Norwalk VLP (NVLP) and composite VLP (CVLP) as indicated in the legend. Serum was collected on day 21 and 35 and CVLP-specific IgG and IgA was measured by ELISA. Results are displayed as geometric group means+SEM.
Figure 16:
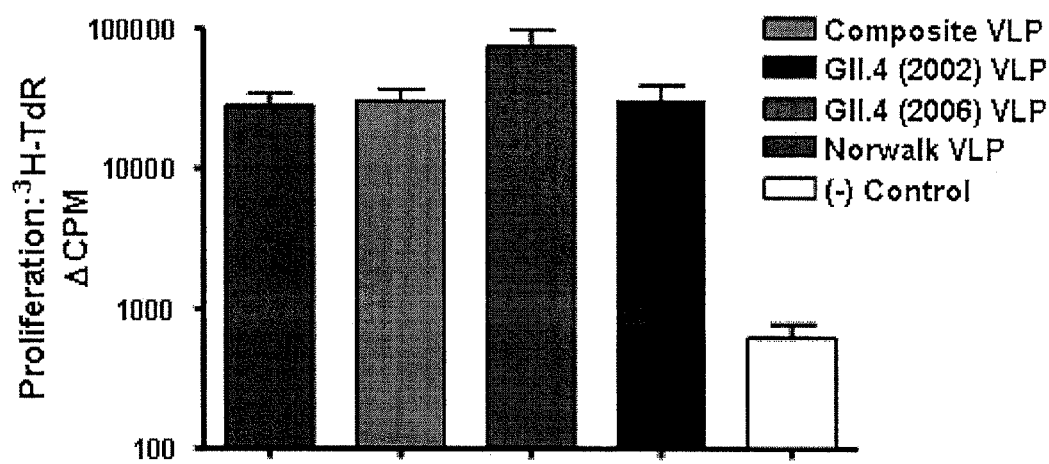
FIG. 16. Rabbits were immunized IM on days 0, 14, and 21 with equal amounts of Norwalk VLP (NVLP) and composite VLP (CVLP). Spleens were collected on day 35 and unfractionated cells were stimulated in vitro for 5 days. Splenocytes were stimulated with various VLPs from the two genogroups as indicated in the graph legend. Results are displayed as geometric group means+SD.

This example outlines experiments designed to determine if high doses of the composite and Norwalk VLPs in the bivalent vaccine would lead to any adverse events. Rabbits were intramuscularly immunized with the bivalent vaccine (see Example 6) on days 0, 14, and 21. VLP doses ranged from 150 µg to 5 µg of each VLP (Norwalk and composite) and each formulation contained 50 µg MPL and 500 µg AlOH. The general health, coat condition, and injection site of the immunized rabbits were monitored every 12 hours for the first 72 hours and then daily thereafter. Serum was collected from each rabbit on day 21 and day 35 and Norwalk VLP (NVLP)-specific (FIG. 14) and composite VLP (CVLP)-specific (FIG. 15) IgG and IgA were evaluated. Spleens were also harvested on day 35 and evaluated for the presence of antigen-specific cellular immunity (FIG. 16).

Serum IgG titers were measured by ELISA using microtiter plates coated with either NVLP or CVLP as a capture. Titers are expressed as reciprocal dilutions. Antigen-specific T-cell responsiveness was evaluated by tritiated thymidine incorporation after a 5-day in vitro stimulation with the indicated antigens (e.g. composite VLPs, GII.4 (2002) VLPs, GII.4 (2006 VLPs, and Norwalk VLPs).

The results from this study shows that the Norovirus bivalent vaccine is safe at the tested doses as evidenced by the fact that all rabbits appeared healthy throughout the study duration and no injection site reactions were observed. The immune responses measured from vaccinated rabbits confirm that the bivalent Norovirus vaccine is effective for eliciting both VLP-specific antibodies as well as VLP-responsive T-cells.

Example 8

Mouse Potency Assay for Norovirus Vaccine Efficacy

Figure 17:
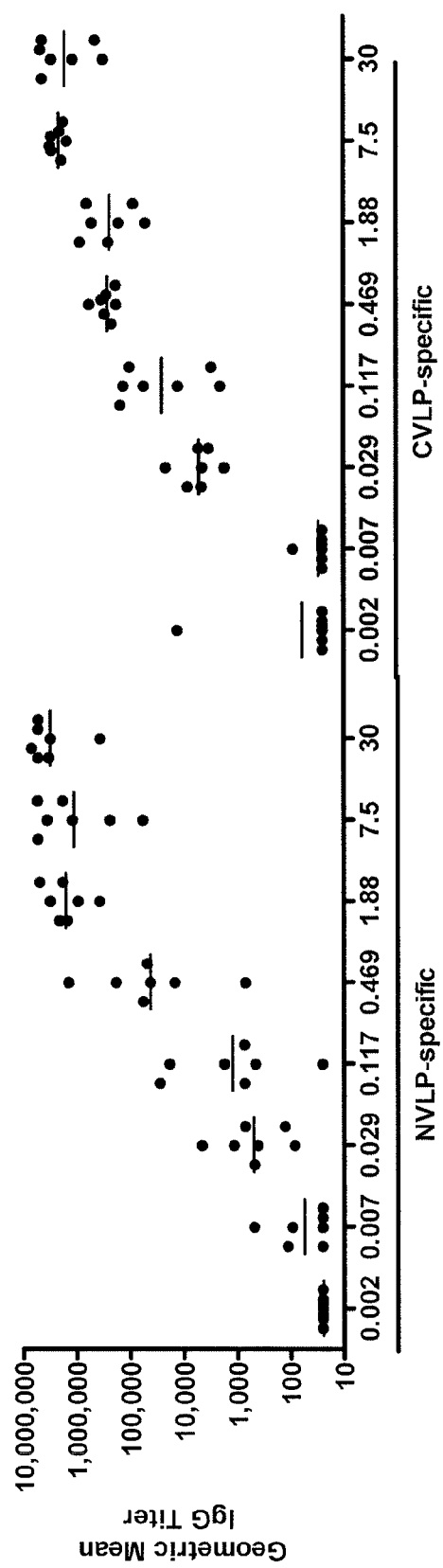
FIG. 17. Mice were immunized IP on days 0 and 7 with equal amounts of Norwalk VLP (NVLP) and composite VLP (CVLP) as indicated on the X axis. Serum was collected on day 14 and analyzed for the presence of VLP-specific IgG by ELISA. Individual responses are shown and titers are expressed as reciprocal dilutions. Horizontal bars represent geometric group means.
Figure 18:
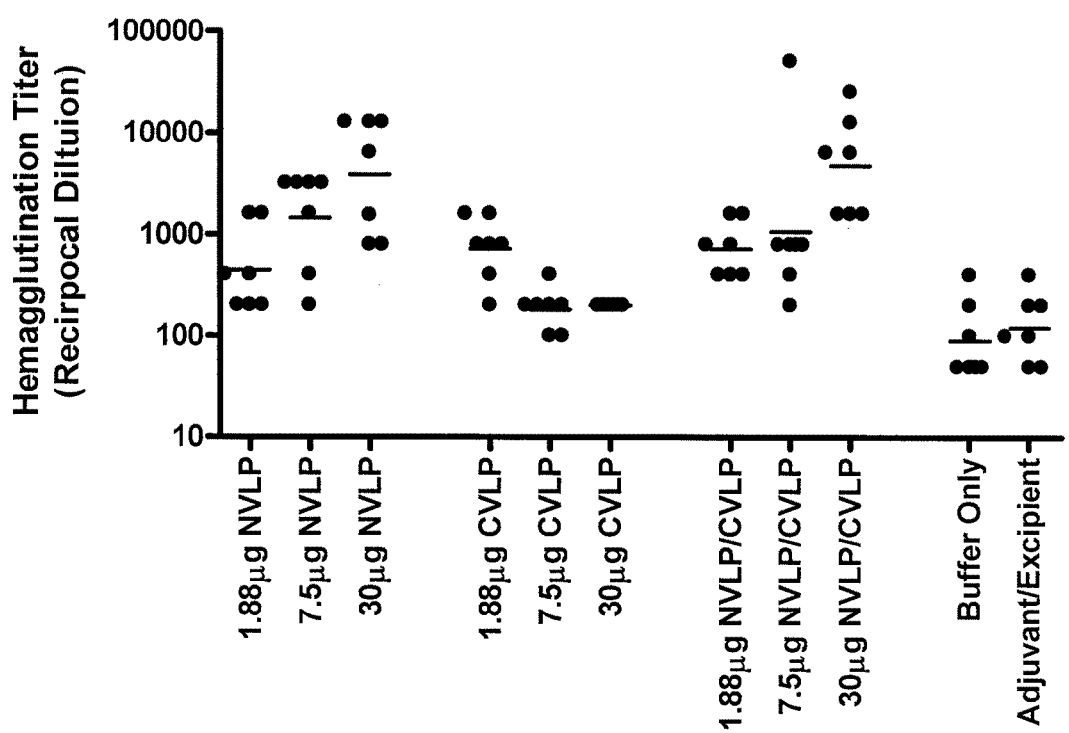
FIG. 18. Mice were immunized IP on days 0 and 7 with equal amounts of Norwalk VLP (NVLP) and composite VLP (CVLP) as indicated on the X axis. Serum was collected on day 14 and analyzed for the presence of antibodies capable of inhibiting hemagglutination of human red blood cells (type O positive). Individual responses are shown and titers are expressed as reciprocal dilutions. Horizontal bars represent geometric group means.

This example outlines the development of a mouse potency assay to evaluate the potency of the bivalent Norovirus vaccine. Mice were immunized IP on day 0 and 7 with equal concentrations ranging from 0.002 µg to 30 µg of Norwalk VLP (NVLP) and composite VLP (CVLP). Serum was collected from each mouse on day 14 and VLP-specific IgG was evaluated (FIG. 17). The neutralizing activity of the antibodies was also measured by hemagglutination inhibition assay (HAI) using Type O positive human red blood cells (FIG. 18). Only Norwalk-specific HAI titers could be assessed because the GII.4 genotypes do not hemagglutinate red blood cells.

Serum IgG titers were measured by ELISA using microtiter plates coated with either NVLP or CVLP as a capture. Titers are expressed as reciprocal dilutions. HAI titers were measured by using a standard hemagglutination assay.

The results from this study indicate that vaccination with the bivalent Norovirus vaccine elicits potent and functional IgG titers such that they are capable of inhibiting hemagglutination of human red blood cells. These results are of particular importance because they demonstrate that the antibodies elicited in response to the vaccination have functionality, which may lead to neutralization of the actual virus during an infection.

Example 9

Chitosan Formulations of a Norovirus Bivalent Vaccine

Figure 19:
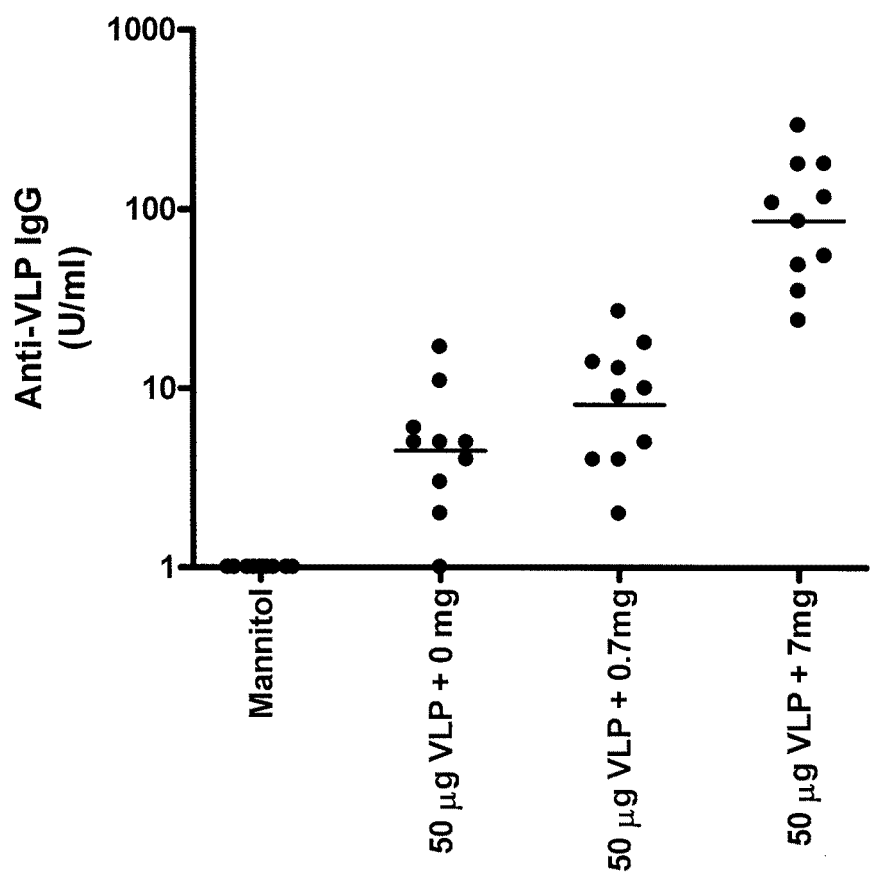
FIG. 19. Serum anti-VLP IgG in rabbits intranasally immunized on days 0 and 21 with 50 µg of VLP vaccine formulation (Norwalk VLPs+composite GII.4 VLPs). Individual responses are shown and expressed in µg/mL from serum collected on day 35. Bars indicate the geometric group means.

A study was performed in rabbits with the bivalent Norovirus VLP vaccine to evaluate the role of chitosan in this vaccine formulation. The formulation contained equal amounts of a Norwalk VP1 VLP and a composite GII.4 VLP (see Example 2). Rabbits were intranasally immunized with dry powder formulations on days 0 and 21. VLP doses ranged from 150 µg to 5 µg of each type of VLP and each formulation contained 50 µg MPL. Chitosan concentration was varied for each dose range (7 mg, 0.7 mg and 0 mg) to determine its role in immunogenicity. Serum was collected from each rabbit and VLP-specific IgG was evaluated (FIG. 19).

Serum IgG titers were measured by ELISA using microtiter plates coated with VLP as a capture. Serial dilutions of a proprietary in-house rabbit anti-VLP serum were used to generate standard curves. Titers are expressed in Units anti-VLP/mL (one Unit is approximately equal to 1 µg).

Results from these experiments indicate that chitosan at the highest dose (7 mg) is required to achieve maximum immunogenicity. The IgG data for the 50 µg dose is shown in FIG. 19 and results are represented as U/ml. The IgA antibody response is shown below in Table 1.

TABLE 1

| Antigen-Specific IgA Responses. | | | |
|---|---|---|---|
| VLP (µg) | 50 | 50 | 50 |
| Chitosan (mg) | 7 | 0.7 | 0 |

TABLE 1-continued

| Antigen-Specific IgA Responses. | | | |
|---|---|---|---|
| Geometric Mean IgA Titers (95% CI) | 770 (474, 1253) | 67 (32, 142) | 83 (38, 179) |

Example 10

Design of a Norovirus GII Consensus Gene

The methods of the present invention may also be used to generate capsid consensus sequences amongst Norovirus GII isolates from different GII genotypes, GII.1, GII.2, GII.3. The following alignment was generated from VP1 sequences from three different Norovirus GII isolates. The consensus sequence (SEQ ID NO: 7) determined from the homology comparison of the three GII strains is shown in FIG. 20.

A composite sequence is derived from the consensus sequence by selecting amino acids from a sequence of one of the strains for variable positions of the consensus sequence where two or more strains differ. Preferably the sequence from which amino acids are selected is a recently circulating strain, or a strain that is more commonly associated with disease or more commonly occurring amongst the strains being evaluated. In this Example, amino acids were selected from the Snow Mountain sequence at variable positions of the consensus sequence at which all three strains differed to generate a composite VP1 GII sequence. The composite GII sequence is used for production of a synthetic gene encoding a composite GII VP1 protein for induction of cross-immunity amongst GII Norovirus isolates.

The composite GII VP1 amino acid sequence (Composite) is shown in the alignment below as SEQ ID NO: 11 with the amino acid sequences of the VP1 proteins from GII.1 (Accession Number: AAL13001), GII.2 Snow Mountain (Accession Number: AAB61685), and GII.3 virus (Accession Number: AAL12998) (SEQ ID NOs: 8, 9, and 10, respectively).

```
Composite  MKMASNDAAPSNDGAAGLVPESNNEVMALEPVAGAAIAAPLTGQTNIIDPWIR  53
     GII.1  MKMASNDAAPSNDGAAGLVPEVNNETMALEPVAGASIAAPLTGQNNVIDPWIR  53
 GII.2 Snow MKMASNDAAPSTDGAAGLVPESNNEVMALEPVAGAALAAPVTGQTNIIDPWIR  53
     GII.3  MKMASNDAAPSNDGAAGLVPEINNEAMALEPVAGAAIAAPLTGQQNIIDPWIM  53

Composite  ANFVQAPNGEFTVSPRNSPGEVLLNLELGPELNPYLAHLARMYNGYAGGMEVQ  106
     GII.1  MNFVQAPNGEFTVSPRNSPGEILLNLELGPELNPFLAHLSRMYNGYAGGVEVQ  106
 GII.2 Snow ANFVQAPNGEFTVSPRNAPGEVLLNLELGPELNPYLAHLARMYNGYAGGMEVQ  106
     GII.3  NNFVQAPGGEFTVSPRNSPGEVLLNLELGPEINPYLAHLARMYNGYAGGFEVQ  106

Composite  VMLAGNAFTAGKLVFAAIPPHFPIENLSPQQITMFPHVIIDVRTLEPVLLPLP  159
     GII.1  VLLAGNAFTAGKLVFAAIPPHFPIGNLSPGQIAMFPHVIIDVRTLEPVLLPLP  159
 GII.2 Snow VMLAGNAFTAGKLVFAAVPPHFPVENLSPQQITMFPHVIIDVRTLEPVLLPLP  159
     GII.3  AVLAGNAFTAGKVIFAAIPPNFPIDNLSAAQITMCPHVIVDVRQLEPINLPMP  159

Composite  DVRNNFFHYNQKDDPRMRLVAMLYTPLRSNGSGDDVFTVSCRVLTRPSPDFDF  212
     GII.1  DVRNNFFHYNQEPEPRMRLVAMLYTPLRSNGSGDDVFTVSCRVLTRPSPDFDF  212
 GII.2 Snow DVRNNFFHYNQKDDPKMRIVAMLYTPLRSNGSGDDVFTVSCRVLTRPSPDFDF  212
     GII.3  DVRNNFFHYNQGSDSRLRLIAMLYTPLRANNSGDDVFTVSCRVLTRPSPDFSF  212

Composite  NYLVPPTVESKTKPFTLPILTIGELSNSRFPVPIDQLYTSPNEVIVVQCQNGR  265
     GII.1  NYLVPPTVESKTKPFTLPILTIGELSNSRFPVPIDELYTSPNEGLVVQPQNGR  265
 GII.2 Snow TYLVPPTVESKTKPFTLPILTLGELSNSRFPVSIDQMYTSPNEVISVQCQNGR  265
     GII.3  NFLVPPTVESKTKLFTLPILTISEMSNSRFPVPIDSLHTSPTENIVVQCQNGR  265

Composite  CTLDGELQGTTQLQPSGICAFRGEVTR--AHLSDQDN-------DHRWNIQIT  318
     GII.1  STLDGELLGTTQLVPSNICSLRG--RINAHLSD--N-------QHRWNMQVT  306
 GII.2 Snow CTLDGELQGTTQLQVSGICAFKGEVT--AHL--QDN-------DHLYNITIT  306
     GII.3  VTLDGELMGTTQLLPSQICAFRGTLTRSTSRASDQADTPTPRLFNHRWHIQLD  318

Composite  NLNGTPFDPSEDIPAPLGTPDFQGRVFGVISQRNPDNT-------NRAHDAVV  371
     GII.1  NANGTPFDPTEDVPAPLGTPDFLANIYGVTSQRNPDNT-------CRAHDGIL  352
 GII.2 Snow NLNGSPFDPSEDIPAPLGVPDFQGRVFGVITQRDKQNAAGQSQPANRGHDAVV  359
     GII.3  NLNGTPYDPAEDIPAPLGTPDFRGKVFGVASQRNPDST-------TRAHEAKV  364
```

-continued

```
  Composite PTYSAQFTPKLGSVQIGTWETDDFDVNQPTKFTPV--GLNDTBHFNQWVLPRY 424
       GII.1 ATWSPKFTPKLGSVVLGTWEDRDFDINQPTRFTPV--GLYDTDHFNQWVLPYY 403
  GII.2 Snow PTYTAQYTPKLGQVQIGTWQTDDLKVNQPVKFTPV--GLNDTBHFNQWVVPRY 410
       GII.3 DTTSDRFTPKLGSLEIIT-ESGDFDTNQSTKFTPVGIGVDNEAEFQQWSLPNY 416
  Composite SGALTLNMNLAPSVAPVFPGEQLLFFRSYLPLKGGYSNGAIDCLLPQEWVQHF 477
       GII.1 SGALTLNMNLAPSVAPLFPGEQLLFFRSHVPLKGGTSNGAIDCLLPQEWVQHF 456
  GII.2 Snow AGALNLNTNLAPSVAPVFPGERLLFFRSYLPLKGGYGNPAIDCLLPQEWVQHF 463
       GII.3 SGQFTHNMNLAPAVAPNFPGEQLLFFRSQLPSSGGRSNGVLDCLVPQEWVQHF 469
  Composite YQESAPSMTEVALVRYINPDTGRVLFEAKLHRAGFMTVASNGSAPIVVPPNGY 530
       GII.1 YQESAPSSTDVALIRYTNPDTGRVLFEAKLHRQGFITVANSGSRPIVVPPNGY 509
  GII.2 Snow YQEAAPSMSEVALVRYINPDTGRALFEAKLHRAGFMTVSSNTSAPVVVPANGY 516
       GII.3 YQESAPAQTQVALVRYVNPDTGRVLFEAKLHKLGFMTIAKNGDSPITVPPNGY 522
  Composite FRFDSWVNQFYSLAPMGTGNGRRRI (SEQ ID NO: 11)           555
       GII.1 FRFDSWVNQFYSLAPMGTGNGRRRV (SEQ ID NO: 8)            534
  GII.2 Snow FRFDSWVNQFYSLAPMGTGNGRRRI (SEQ ID NO: 9)            541
       GII.3 FRFESWVNPFYTLAPMGTGNGRRRI (SEQ ID NO: 10)           547
```

Example 11

Design of a Norovirus GI Consensus Gene

The methods of the present invention may also be used to generate capsid consensus sequences amongst Norovirus GI isolates. The following alignment was generated from VP1 sequences from three different Norovirus GI isolates. The consensus GI sequence (SEQ ID NO: 12) determined from the homology comparison of the three GI strains is shown in FIG. 21.

A composite sequence is derived from the consensus sequence by selecting amino acids from a sequence of one of the strains for variable positions of the consensus sequence where two or more strains differ. Preferably the sequence from which amino acids are selected is a recently circulating strain, or a strain that is more commonly associated with disease or more commonly occurring amongst the strains being evaluated. In this Example, amino acids were selected from the Southampton sequence at variable positions of the consensus sequence at which all three strains differed to generate a composite VP1 GI sequence. The composite GI sequence is used for production of a synthetic gene encoding a composite GI VP1 protein for induction of cross-immunity amongst GI Norovirus isolates.

The composite GI VP1 amino acid sequence (Composite) is shown in the alignment below as SEQ ID NO: 16 with the amino acid sequences of the VP1 proteins from Norwalk virus (Accession Number: M87661), Southampton (Accession Number: Q04542), and Chiba virus (Accession Number: BAB18267) (SEQ ID NOs: 13, 14, and 15, respectively).

```
  Composite MMMASKDATQSADGASGAGQLVPEVNTADPLPMDPVAGSSTAVATAGQVNMID 53
 Norwalk VP MMMASKDATSSVDGASGAGQLVPEVNASDPLAMDPVAGSSTAVATAGQVNPID 53
 Southampto MMMASKDAPQSADGASGAGQLVPEVNTADPLPMEPVAGPTTAVATAGQVNMID 53
  Chiba VP1 MMMASKDATPSADGATGAGQLVPEVNTADPIPIDPVAGSSTALATAGQVNLID 53

Composite PWIINNFVQAPQGEFTISPNNTPGDVLFDLQLGPHLNPFLSHLSQMYNGWVGN 106
 Norwalk VP PWIINNFVQAPQGEFTISPNNTPGDVLFDLSLGPHLNPFLLHLSQMYNGWVGN 106
 Southampto PWIVNNFVQSPQGEFTISPNNTPGDILFDLQLGPHLNPFLSHLSQMYNGWVGN 106
  Chiba VP1 PWIINNFVQAPQGEFTISPNNTPGDVLFDLQLGPHLNPFLSHLSQMYNGWVGN 106

Composite MRVRILLAGNAFTAGKIIVCCVPPGFTSSSLTIAQATLFPHVIADVRTLDPIE 159
 Norwalk VP MRVRIMLAGNAFTAGKIIVSCIPPGFGSHNLTIAQATLFPHVIADVRTLDPIE 159
 Southampto MRVRILLAGNAFSAGKIIVCCVPPGFTSSSLTIAQATLFPHVIADVRTLEPIE 159
  Chiba VP1 MRVRVVLAGNAFTAGKVIICCVPPGFQSRTLSIAQATLFPHVIADVRTLDPVE 159

Composite VPLEDVRNVLYHNND-NQPTMRLVCMLYTPLRTGGGSGNSDSFVVAGRVLTCP 212
 Norwalk VP VPLEDVRNVLFHNNDRNQQTMRLVCMLYTPLRTGGGTG--DSFVVAGRVMTCP 210
 Southampto MPLEDVRNVLYHTND-NQPTMRLVCMLTYPLRTGGGSGNSDSFVVAGRVLTAP 211
  Chiba VP1 VPLEDVRNVLYHNND-TQPTMRLLCMLYTPLRTGGASGGTDSFVVAGRVLTCP 211

Composite SPDFNFLFLVPPTVEQKTRPFTVPNIPLQTLSNSRFPSPIQGMILSPDASQVV 265
 Norwalk VP SPDFNFLFLVPPTVEQKTRPFTLPNLPLSSLSNSRAPLPISSIGISPDNVQSV 263
 Southampto SSDFSFLFLVPPTIEQKTRAFTVPNIPLQTLSNSRFPSLIQGMILSPDASQVV 264
  Chiba VP1 GPDFNFLFLVPPTVEQKTRPFTVPNIPLKYLSNSRIPNPIEGMSLSPDQTQNV 264

Composite QFQNGRCTIDGQLLGTTPVSxSQLFKVRGKITSGARVLNLTELDGKPFMAFDS 318
 Norwalk VP QFQNGRCTLDGRLVGTTPVSLSHVAKIRG--TSNGTVINLTELDGTPFHPFEG 314
 Southampto QFQNGRCLIDGQLLGTTPATSGQLFRVRGKINQGARTLNLTEVDGKPFMAFDS 317
  Chiba VP1 QFQNGRCTIDGQPLGTTPVSVSQLCKFRGRITSGQRVLNLTELDGSPFMAFAA 317

Composite PAPVGFPDLGKCDWHIRMSKTPNSSGQGDPMRSVSVQTNVQGFVPHLGSIQFD 371
 Norwalk VP PAPIGFPDLGGCDWHINMTQFGHSS-QTQ-----YDVDTTPDTFVPHLGSIQAN 362
 Southampto PAPVGFPDFGKCDWHMRISKTPNNTGSGDPMRSVSVQTNVQGFVPHLGSIQFD 370
  Chiba VP1 PAPAGFPDLGSCDWHIEMSKIPNSSTQNNPIVTNSVKPNSQQFVPHLSSITLD 370

Composite EVFS-PTGDYIGTIEWISPPSTPPGTDINLWKIPDYGSSLSEAANLAPPVYPP 424
 Norwalk VP GIGS---GNYVGVLSWISPPSHPSGSQVDLWKIPNYGSSITEATHLAPSVYPP 412
 Southampto EVFNHPTGDYIGTIEWISQPSTPPGTDINLWEIPDYGSSLSQAANLAPPVFPP 423
  Chiba VP1 ENVS-SGGDYIGTIQWTSPPSDSGGANTNFWKIPDYGSSLAEASQLAPAVYPP 422

Composite GFGEVLVYFMSAFPGPNNRGAPNDVPCLLPQEYITHFVSEQAPTMGEAALLHY 477
 Norwalk VP GFGEVLVFFMSKMPGP----GAYN-LPCLLPQEYISHLASEQAPTVGEAALLHY 461
 Southampto GFGEALVYFVSAFPGPNNRSAPNDVPCLLPQEYITHFVSEQAPTMGDAALLHY 476
  Chiba VP1 GFNEVIVYFMASIPGPNQSGSPNLVPCLLPQEYITHFISEQAPIQGEAALLHY 475
```

```
                                   -continued
Composite   VDPDTNRNLGEFKLYPGGYLTCVPNGVSAGPQQLPLNGVFVFVSWVSRFYQLK 530
Norwalk VP  VDPDTGRNLGEFKAYPDGFLTCVPNGASSGPQQLPINGVFVFVSWVSRFYQLK 514
Southampto  VDPDTNRNLGEFKLYPGGYLTCVPNGVGAGPQQLPLNGVFLFVSWVSRFYQLK 529
Chiba VP1   VDPDTNRNLGEFKLYPGGYLTCVPNSSSTGPQQLPLDGVFVFASWVSRFYQLK 528

Composite   PVGTASTARGRLGVRR (SEQ ID NO: 16)                     546
Norwalk VP  PVGTASSARGRLGLRR (SEQ ID NO: 13)                     530
Southampto  PVGTASTARGRLGVRR (SEQ ID NO: 14)                     545
Chiba VP1   PVGTAGPARGRLGVRR (SEQ ID NO: 15)                     544
```

Example 12

Design of a Human Papillomavirus Consensus Gene for L1

The methods of the present invention may also be used to generate consensus sequences amongst other non-enveloped viruses. The following alignment was generated from three Human Papillomavirus (HPV): HPV-11, HPV-16, and HPV-18. The consensus L1 capsid protein sequence (SEQ ID NO: 17) determined from the homology comparison of the three HPV strains is shown in FIG. 22.

A composite sequence is derived from the consensus sequence by selecting amino acids from a sequence of one of the strains for variable positions of the consensus sequence where two or more strains differ. Preferably the sequence from which amino acids are selected is a recently circulating strain, or a strain that is more commonly associated with disease or more commonly occurring amongst the strains being evaluated. In this Example, amino acids were selected from the HPV-18 sequence at variable positions of the consensus sequence at which all three strains differed to generate a composite L1 HPV sequence. The composite HPV sequence is used for production of a synthetic gene encoding a composite L1 polypeptide for induction of cross-immunity amongst a variety of HPV strains.

The composite HPV L1 amino acid sequence (Composite) is shown in the alignment below as SEQ ID NO: 21 with the amino acid sequences of the L1 proteins from HPV-11, HPV-16, and HPV-18 virus (SEQ ID NOs: 18, 19, and 20, respectively).

```
Composite  MCLYTRVLILHYHLLPLYGPLYHPRPLPHSILVYMVHIIICGHYIILFLRNV 53
HPV16 L1                              MQVTFIYIL-VITC-----YENDV 18
HPV18 L1   MCLYTRVLILHYHLLPLYGPLYHPRPLPHSILBYMVHIIICGHYIILFLRNV 53

Composite  NVFPIFLQMALWRPSDNTVYLPPP-PVSKVVNTDDYVTRTNIFYHAGSSRLLA 106
HPV11 L1              MWRPSDSTVYVPPPNPVSKVVATDAYVKRTNIFYHASSSRLLA 43
HPV16 L1   NVYHIFFQMSLWLPSEATVYLPPV-PVSKVVSTDEYVARTNIYYHAGTSRLLA 70
HPV18 L1   NVFPIFLQMALWRPSDNTVYLPPP-SVARVVNTDDYVTPTSIFYHAGSSRLLT 105

Composite  VGHPYFRIKKGGGNKQDVPKVSGYQYRVFRVQLPDPNKFGLPDTSIYNPETQR 159
HPV11 L1   VGHPYYSIKK--VNKTVVPKVSGYQYRVFKVVLPDPNKFALPDSSLFDPTTQR 94
HPV16 L1   VGHPYFPIKKPNNNKILVPKVSGLQYRVFRIHLPDPNKFGFPDTSFYNPDTQR 123
HPV18 L1   VGNPYFRVPAGGGNKQDIPKVSAYQYRVFRVQLPDPNKFGLPDTSIYNPETQR 158

Composite  LVWACAGVEVGRGQPLGVGLSGHPLLNKLDDTENSHAYTSNVGEDNRDNVSMD 212
HPV11 L1   LVWACTGLEVGRGQPLGVGVSGHPLLNKYDDVENSGGYGGNPGQDNRVNVGMD 147
HPV16 L1   LVWACVGVEVGRGQPLGVGISGHPLLNKLDDTENASAYAANAGVDNRECISMD 176
HPV18 L1   LVWACAGVEIGRGQPLGVGLSGHPFYNKLDDTESSHAATSNVSEDVRDNVSVD 211

Composite  YKQTQLCILGCAPPIGEHWGKGTACKNRPVSQGDCPPLELINTVIQDGDMVDT 265
HPV11 L1   YKQTQLCMVGCAPPLGEHWGKGTQCSNTSVQNGDCPPLELITSVIQDGDMVDT 200
HPV16 L1   YKQTQLCLIGCKPPIGEHWGKGSPCTNVAVNPGDCPPLELINTVIQDGDMVDT 229
HPV18 L1   YKQTQLCILGCAPAIGEHWAKGTACKSRPLSQGDCPPLELKNTVLEDGDMVDT 264

Composite  GFGAMDFSTLQDNKSEVPLDICQSICKYPDYLQMSADPYGDSLFFYLRREQMF 318
HPV11 L1   GFGAMNFADLQINKSDVPLDICGTVCKYPDYLQMAADPYGDRLFFYLRKEQMF 253
HPV16 L1   GFGAMDFTTLQANKSEVPLDICTSICKYPDYIKMVSEPYGDSLFFYLRREQMF 282
HPV18 L1   GYGAMDFSTLQDTKCEVPLDICQSICKYPDYLQMSADPYGDSMFFCLRREQLF 317

Composite  ARHFFNRAGTVGETVPDDLYIKGTGMPASPASSVYSPTPSGSIVTSDAQLFNK 371
HPV11 L1   ARHFFNRAGTVGEPVPDDLLVKGGNNRSSVASSIYVHTPSGSLVSSEAQLFNK 306
HPV16 L1   VRHLFNRAGSNYPDDLYIKGSGSTANLASSNYFPTPSGSMVTSDAQIFNK 335
HPV18 L1   ARHFWNRAGTMGDTVPQSLYIKGTGMPASPGSCVYSPSPSGSIVTSDSQLFNK 370

Composite  PYWLQKAQGHNNGICWGNQLFVTVVDTTRSTNMTLCAS-QSPSPGTYDNTKFK 424
HPV11 L1   PYWLQKAQGHNNGICWGNHLFVTVVDTTRSTNMTLCAS-VSKSA-TYTNSDYK 357
HPV16 L1   PYWLQRAQGHNNGICWGNQLFVTVVDTTRSTNMSLCAA-ISTSETTYKNTNFK 387
HPV18 L1   PYWLHKAQGHNNGVCWHNQLFVTVVDTTPSTNLTICASTQSPVPGQYDATKFK 423

Composite  EYSRHVEEYDLQFIFQLCTITLTADVMSYIHSMNSSILEDWNFGLPPPPTGTL 477
HPV11 L1   EYMRHVEEFDLQFIFQLCSITLSAEVMAYIHTMNPSVLEDWNFGLSPPPNGTL 410
HPV16 L1   EYLRHGEEYDLQFIFQLCKITLTADVMTYIHSMNSTILEDWNFGLQPPPGGTL 440
HPV18 L1   QYSRHVEEYDLQFIFQLCTITLTADVMSYIHSMNSSILEDWNFGVPPPPTTSL 476

Composite  EDTYRFVQSQAITCQKDTPPAEKKDPYKKLKFWEVNLKEKFSLDLDQFPLGRK 530
HPV11 L1   EDTYRYVQSQAITCQKPTPEKEKQDPYKDMSFWEVNLKEKFSSELDQFPLGRK 463
HPV16 L1   EDTYRFVTSQAIACQKHTPPAPKEDPLKKYTFWEVNLKEKFSADLDQFPLGRK 493
HPV18 L1   VDTYRFVQSVAITCQKDAAPAENKDPYDKLKFWNVDLKEKFSLDLDQYPLGRK 529

Composite  FLLQAGLRRKPTI--GGRKRSAPSASTSSTPAKRKRVKAR (SEQ ID NO: 21) 569
HPV11 L1   FLLQSGYRGRTSARTGIKR--PAVSKPSTAPKRKRTKTK  (SEQ ID NO: 18) 500
HPV16 L1   FLLQAGLKAKPKPTLGKRKATPTTSSTSTTAKRKKRKL   (SEQ ID NO: 19) 531
HPV18 L1   FLVQAGLRRKPTI--GPRKRSAPSATTSSKPAKRVRVRAR (SEQ ID NO: 20) 567
```

Example 13

Dose Escalation Safety Study of Composite VLP Vaccine Formulation in Humans

A double-blind, controlled, dose-escalation phase 1 study of the safety and immunogenicity of a Norovirus vaccine is conducted. The vaccine consists of composite Norovirus virus-like particles (VLPs) in a dry powder matrix designed for intranasal administration. The composite VLPs contain a polypeptide having the amino acid sequence of SEQ ID NO: 1. Vaccines include healthy adult volunteers who are H type 1 antigen secretors. The rationale for enrollment of H type 1 antigen secretors is that H type 1 antigen secretors are susceptible to Norovirus infections while non-secretors are resistant. As a control, 2 additional volunteers at each dosage level receive matrix alone. The dry powder matrix includes 25 MPL® adjuvant, 7 mg chitosan, 1.5 mg mannitol, and 1.5 mg sucrose. Volunteers are dosed on days 0 and 21 and are required to keep a 7-day diary of symptoms after each dose. Blood for serology, antibody secreting cells (ASC), and stool and saliva samples for mucosal antibody evaluation are collected.

The components of the vaccine are listed in Table 2. The vaccine is packaged in an intranasal delivery device. Single administrations of the composite VLP vaccine are packaged in a single dose Bespak (Milton Keynes, UK) UniDose DP dry powder intranasal delivery device. Each device delivers 10 mg of the dry powder vaccine formulation. Each dose of vaccine consists of two delivery devices, one in each nostril. The total vaccine dose is 20 mg of dry power. The formulation of Adjuvant/Excipient is the same as the composite VLP vaccine except that no composite VLP antigen is included in the formulation. The formulation of the Adjuvant/Excipient (also referred to as dry powder matrix) is summarized in Table 3.

TABLE 2

Composite VLP Vaccine Composition

| Component | Molecular class | Quantity per 10 mg dry powder | % of Final Formulation |
|---|---|---|---|
| Composite VLP | Recombinant protein | 2.5, 7.5 or 25, 50 μg | 0.025, 0.075, 0.25, or 50% |
| Monophosphoryl Lipid A | Phospholipid | 25 μg | 0.25% |
| Chitosan | Polysaccharide | 7.0 mg | 70% |
| Mannitol | Sugar | 1.5 mg | 15%* |
| Sucrose | Sugar | 1.5 mg | 15% |

TABLE 3

Adjuvant/Excipient (dry powder matrix)

| Component | Molecular class | Quantity per 10 mg dry powder | % of Final Formulation |
|---|---|---|---|
| Monophosphoryl Lipid A | Phospholipid | 25 μg | 0.25% |
| Chitosan | Polysaccharide | 7.0 mg | 70% |
| Mannitol | Sugar | 1.5 mg | 15% |
| Sucrose | Sugar | 1.5 mg | 15% |

Specifically, the dose escalation of the vaccine is conducted as follows: After appropriate screening for good health, a group of 3 volunteers is randomized to receive either 5 μg of the composite VLP vaccine plus dry powder matrix (n=2) or dry powder matrix alone (n=1) by the intranasal route. These 3 volunteers are followed for safety for 21 days, and the Independent Safety Monitor (ISM) reviews their safety data. After approval of the ISM, these individuals receive their second dose of vaccine or matrix on day 21, and 4 additional volunteers are randomized to receive either 5 μg VLP protein plus dry powder matrix (n=3) or matrix alone (n=1) by the intranasal route. The ISM reviews the safety data from this second group and after approval of the ISM, the second intranasal dose is given 21 days after the first dose. Volunteers keep a 7-day diary of symptoms after each dose. After the ISM determines that escalation to the next higher dose is acceptable, another group of 7 volunteers is randomized to receive either the composite VLP vaccine containing 15 μg VLP protein (n=5) or dry powder matrix alone (n=2) by the intranasal route at day 0 and day 21. Again, 7-day symptom diaries are recorded and reviewed by the ISM before the second dose at day 21. Finally, after review of the safety data from the first two dosage cohorts, the ISM determines if dose escalation is acceptable and a final group of 7 volunteers is randomized to receive either the composite VLP vaccine containing 50 μg VLP protein (n=5) or dry powder matrix alone (n=2) by the intranasal route on day 0 and day 21. Again, the ISM reviews seven-day symptom diaries and other safety data before the second dose at day 21.

The volunteers keep a daily diary of symptoms (including local symptoms such as: nasal discharge, nasal pain/discomfort, nasal congestion, runny nose, nasal itching, nose bleed, headache and systemic symptoms such as: daily oral temperature, myalgia, nausea, vomiting, abdominal cramps, diarrhea, and loss of appetite) for 7 days after receiving the composite VLP vaccine or dry powder matrix alone. Interim medical histories are obtained at each follow-up visit (days 7±1, 21±2, 28±2, 56±2 and 180±14); volunteers are queried about interim illness, medications, and doctor's visits. Volunteers are asked to report all serious or severe adverse events including events that are not solicited during follow up visits. Volunteers have CBC and serum creatinine, glucose, AST, and ALT assessed on days 7 and 28 (7 days after each immunization) and, if abnormal, the abnormal laboratory test is followed until the test becomes normal or stabilizes.

Blood is collected before immunization and on days 7±1, 21±2, 28±2, 56±2, and 180±14 to measure serum antibodies to the composite VLP vaccine by enzyme-linked immunosorbent assays (ELISA). Before and on day 7 after administration of each dose of vaccine or dry powder matrix alone peripheral blood lymphocytes are collected to detect antibody secreting cells by ELISPOT assay. Before and on days 21±2, 56±2 and 180±14 after vaccination, whole blood is obtained to separate cells and freeze for future studies of cell mediated immunity, including cytokine production in response to composite VLP antigen, and lymphoproliferation. Whole stool samples are collected before immunization and on days 7±1, 21±2, 28±2, 56±2, and day 180±14 for anti-composite VLP sIgA screening. Saliva is collected with a commercially available device (Salivette, Sarstedt, Newton, N.C.) before immunization and on days 7±1, 21±2, 28±2, 56±2, and if positive for mucosal antibodies at day 56, a day 180±14 sample is collected and screened for anti-composite VLP sIgA. Finally blood from volunteers receiving the highest dose of composite VLPs (50 μg, third cohort described above) is screened for memory B-cells on days 0, 21, 56 and 180.

The following methods are used to analyze the blood, stool, and saliva samples collected from immunized individuals or individuals receiving the dry powder matrix alone:

A. Serum Antibody Measurements by ELISA

Twenty mL of blood are collected before and at multiple time points after vaccination for measurement of antibodies to the composite VLP by ELISA, using purified recombinant composite VLPs as target antigen to screen the coded specimens. Briefly, composite VLPs in carbonate coating buffer pH 9.6 are used to coat microtiter plates. Coated plates are washed, blocked, and incubated with serial two-fold dilutions of test serum followed by washing and incubation with enzyme-conjugated secondary antibody reagents specific for human IgG, IgM, and IgA. Appropriate substrate solutions are added, color developed, plates read, and the IgG, IgM, and IgA endpoint titers are determined in comparison to a reference standard curve for each antibody class. A positive response is defined as a 4-fold rise in titer after vaccination.

B. Antibody Secreting Cell Assays

Peripheral blood mononuclear cells (PMBCs) are collected from thirty mL of heparinized blood for ASC assays to detect cells secreting antibodies to composite VLPs. These assays are performed on days 0, 7±1, 21±2, and 28±2 after administration of the composite VLP vaccine or dry powder matrix alone. A positive response is defined as a post-vaccination ASC count per $10^6$ PBMCs that is at least 3 standard deviations (SD) above the mean pre-vaccination count for all subjects (in the log metric) and at least 8 ASC spots, which corresponds to the mean of medium-stimulated negative control wells (2 spots) plus 3 SD as determined in similar assays.

C. Measurement of Composite VLP-Specific Memory B-Cells

Heparinized blood is collected from cohort 3 (30 mL days 0 and 21, 50 mL days 56 and 180) to measure memory B cells on days 0, 21, 56 and 180 after vaccination using an ELISpot assay preceded by an in vitro antigen stimulation. A similar assay was successfully used to measure frequency of memory B cells elicited by Norwalk VLP formulations in rabbits (See WO 2008/042789, herein incorporated by reference in its entirety). Peripheral blood mononuclear cells ($5\times10^6$ cells/mL, 1 mL/well in 24-well plates) are incubated for 4 days with composite VLP antigen (2-10 µg/mL) to allow for clonal expansion of antigen-specific memory B cells and differentiation into antibody secreting cells. Controls include cells incubated in the same conditions in the absence of antigen and/or cells incubated with an unrelated antigen. Following stimulation, cells are washed, counted and transferred to ELISpot plates coated with composite VLP. To determine frequency of VLP-specific memory B cells per total Ig-secreting B lymphocytes, expanded B cells are also added to wells coated with anti-human IgG and anti-human IgA antibodies. Bound antibodies are revealed with HRP-labeled anti-human IgG or anti-human IgA followed by True Blue substrate. Conjugates to IgA and IgG subclasses (IgA1, IgA2 and IgG1-4) may also be used to determine antigen-specific subclass responses which may be related with distinct effector mechanisms and locations of immune priming. Spots are counted with an ELISpot reader. The expanded cell populations for each volunteer are examined by flow cytometry to confirm their memory B cell phenotype, i.e. CD19+, CD27+, IgG+, IgM+, CD38+, IgD D. Cellular Immune Responses Heparinized blood (50 mL cohorts 1 and 2, 25 mL cohort 3) is collected as coded specimens and the PBMCs isolated and cryopreserved in liquid nitrogen for possible future evaluation of cell-mediated immune (CMI) responses to composite VLP antigen. Assays that may be performed include PBMC proliferative and cytokine responses to composite VLP antigen and can be determined by measuring interferon (IFN)-γ and interleukin (IL)-4 levels according to established techniques.

E. Collections of Stool and Saliva for Anti-Composite VLP sIgA

Anti-composite VLP IgA is measured in stool and saliva samples. Saliva specimens are treated with protease inhibitors (i.e. AEBSF, leupeptin, bestatin, and aprotinin) (Sigma, St. Louis, Mo.), stored at −70° C., and assayed using a modification of a previously described assay (Mills et al. (2003) Infect. Immun. 71: 726-732). Stool is collected on multiple days after vaccination and specimens stored at −70° C. until analysis. The specimens are thawed, and protease inhibitor buffer added to prepare a 10% w/v stool suspension. Stool supernatants are assayed for composite VLP-specific mucosal IgA by ELISA, as described below.

Approximately 2-3 mL of whole saliva is collected before and at multiple time points after vaccination. Saliva is collected by a commercially available device (Salivette, Sarstedt, Newton, N.C.), in which a Salivette swab is chewed or placed under the tongue for 30-45 seconds until saturated with saliva. Saliva is collected from the swab by centrifugation.

F. Measurement of Anti-Composite VLP in Stool and Saliva

ELISAs, utilizing plates coated with either anti-human IgA antibody reagents or target composite VLP antigen coatings, are performed to determine total IgA and to titer the specific anti-VLP IgA responses for each specimen. Total or specific IgA are revealed with HRP-labeled anti-human IgA as described above. An internal total IgA standard curve is included to quantify the IgA content. Response is defined as a 4-fold rise in specific antibody.

Example 14

Safety and Immunogenicity Study of Two Dosages of Intranasal Composite VLP Vaccine in Humans A randomized, double blind study in healthy adults is conducted to compare the safety and immunogenicity of two dosage levels of a composite Norovirus virus-like particle (VLP) vaccine with adjuvant/excipients and placebo controls (empty device). The vaccine consists of composite Norovirus virus-like particles (VLPs) in a dry powder matrix designed for intranasal administration as described in Example 13. Vaccines include healthy adult volunteers who are H type 1 antigen secretors. The human volunteers are randomly assigned to one of four groups and each group receives one of the following treatments: a 50 mg dose of the composite VLP vaccine, a 100 µg dose of the composite VLP vaccine, the adjuvant/excipient, or placebo. Volunteers are dosed on days 0 and 21 and are required to keep a 7-day diary of symptoms after each dose. Blood for serology, antibody secreting cells (ASC), and stool and saliva samples for mucosal antibody evaluation are collected.

The components of the vaccine are listed in Table 2 in Example 13. The vaccine is packaged in an intranasal delivery device. Single administrations of the composite VLP vaccine are packaged in a single dose Bespak (Milton Keynes, UK) UniDose DP dry powder intranasal delivery device. Each device delivers 10 mg of the dry powder vaccine formulation. Each dose of vaccine consists of two delivery devices, one in each nostril. The total vaccine dose is 20 mg of dry power. Therefore, the 50 µg vaccine dose consists of two devices that each deliver 10 mg of dry powder formulation, wherein each 10 mg of dry powder formulation consists of 25 µg of composite VLP, 25 µg MPL® adjuvant, 7 mg chitosan, 1.5 mg mannitol, and 1.5 mg sucrose. Similarly, the 100 μg vaccine dose consists of two devices that each deliver 10 mg of dry powder formulation, wherein each 10 mg of dry powder formulation consists of 50 μg of composite VLP, 25 μg MPL® adjuvant, 7 mg chitosan, 1.5 mg mannitol, and 1.5 mg sucrose. The formulation of Adjuvant/Excipient is the same as the composite VLP vaccine except that no composite VLP antigen is included in the formulation. The formulation of the Adjuvant/Excipient (also referred to as dry powder matrix) is summarized in Table 3 in Example 13. The placebo group receives two empty devices.

The volunteers keep a daily diary of symptoms (including local symptoms such as: nasal discharge, nasal pain/discomfort, nasal congestion, runny nose, nasal itching, nose bleed, headache and systemic symptoms such as: daily oral temperature, myalgia, nausea, vomiting, abdominal cramps, diarrhea, and loss of appetite) for 7 days after receiving either one of two doses of the composite VLP vaccine, dry powder matrix alone, or the placebo. Interim medical histories are obtained at each follow-up visit (days 7±1, 21±2, 28±2, 56±2 and 180±14); volunteers are queried about interim illness, medications, and doctor's visits. Volunteers are asked to report all serious or severe adverse events including events that are not solicited during follow up visits. Volunteers have CBC and serum creatinine, glucose, AST, and ALT assessed on days 7 and 28 (7 days after each immunization) and, if abnormal, the abnormal laboratory test is followed until the test becomes normal or stabilizes.

Blood is collected before immunization and on days 7±1, 21±2, 28±2, 56±2, and 180±14 to measure serum antibodies to the composite VLP vaccine by enzyme-linked immunosorbent assays (ELISA). Before and on day 7 after administration of each dose of vaccine, dry powder matrix alone, or placebo, peripheral blood lymphocytes are collected to detect antibody secreting cells by ELISPOT assay. Before and on days 21±2, 56±2 and 180±14 after vaccination, whole blood is obtained to separate cells and freeze for future studies of cell mediated immunity, including cytokine production in response to composite VLP antigen, and lymphoproliferation. Whole stool samples are collected before immunization and on days 7±1, 21±2, 28±2, 56±2, and day 180±14 for anti-composite VLP sIgA screening. Saliva is collected with a commercially available device (Salivette, Sarstedt, Newton, N.C.) before immunization and on days 7±1, 21±2, 28±2, 56±2, and if positive for mucosal antibodies at day 56, a day 180±14 sample is collected and screened for anti-composite VLP sIgA. Blood is also screened for memory B-cells on days 0, 21, 56 and 180.

Methods used to analyze the blood, stool, and saliva samples collected from immunized individuals, or individuals receiving the dry powder matrix alone or placebo are described in detail in Example 13.

Example 15

Experimental Human Challenge Study with Infectious Norovirus Following Vaccination with Composite Norovirus VLP Vaccine A multi-site, randomized, double-blind, placebo-controlled Phase 1-2 challenge study is conducted in 80 human volunteers immunized with the composite Norovirus VLP vaccine. Eligible subjects include those 18-50 years of age, in good health, who express the H type-1 oligosaccharide (as measured by positive salivary secretor status) and who are other than Type B or AB blood type. Subjects who are non H type-1 secretors or who have Type B or AB blood are reported to be more resistant to infection with Norwalk virus and are excluded from the study. At least 80% of volunteers are expected to be eligible based on these two criteria.

Following screening, eligible volunteers who meet all acceptance criteria are randomized (1:1) into one of two equal sized cohorts with approximately 40 volunteers in each cohort. Cohort 1 is immunized with composite VLP and cohort 2 receives placebo. Volunteers are immunized with 10 mg composite VLP vaccine in each nostril (20 mg total dry powder) or placebo. Each 10 mg of composite VLP vaccine contains 50 μg of Composite VLP, 7 mg chitosan, 25 μg MPL®, 1.5 mg of sucrose and approximately 1.5 mg of mannitol. Thus, each volunteer in cohort 1 receives a total dosage of 100 μg of composite VLP antigen at each immunization. Volunteers receive vaccine or placebo on study days 0 and 21.

The safety of the composite virus VLP vaccine compared to placebo is assessed. Volunteers keep a diary for 7 days following each immunization with the vaccine or placebo to document the severity and duration of adverse events. Serious adverse events (SAEs) and the occurrence of any significant new medical conditions is followed for 6 months after the last dose of vaccine or placebo and for 4 months after the challenge with infectious virus.

All volunteers are challenged with infectious Norovirus between 21 to 42 days after the second dose of vaccine or placebo (between study days 42 and 56). Each volunteer receives at or >than the 50% Human Infectious Dose (HID 50), i.e. the amount of infectious virus that is expected to cause disease in at least 50% of volunteers in the placebo group. The HID 50 is between about 48 and about 480 viral equivalents of the challenge virus strain. The challenge Norovirus is mixed with sterile water and given orally. The inoculation is preceded by ingestion of 500 mg sodium bicarbonate in water, to prevent breakdown of the virus by stomach acid and pepsin. A second ingestion of sodium bicarbonate solution (500 mg sodium bicarbonate in water) is taken 5 minutes after oral inoculation of the infectious virus. The volunteers remain at the challenge facility for at least 4 days and at least 18 hours after symptoms/signs of acute gastroenteritis (vomiting, diarrhea, loose stool, abdominal pain, nausea, and fever) are absent.

Several metrics are monitored to determine the efficacy of the composite VLP vaccine in preventing or reducing symptoms/signs of acute gastroenteritis induced by the viral challenge. All volunteers record their clinical symptoms of acute gastroenteritis and these symptoms are documented by the research staff at the study sites. Disease symptoms/signs from cohort 1 receiving the vaccine are compared to cohort 2 placebo recipients.

Sera and stool samples are routinely collected from all volunteers prior to immunization with the vaccine or placebo, and after challenge. Serum samples are analyzed by ELISA for IgA and IgG, titers against the challenge VLPs. The challenge virus antigen and challenge virus RNA are tested in stool samples by ELISA and PCR, respectively, which indicate the presence of virus, the amount of virus shed from the intestines, and the duration of viral shedding. Subjects who become ill after challenge, are subject to additional laboratory studies including serum chemistries, BUN, creatinine, and liver function tests until symptoms/signs resolve.

Results from the vaccine group (cohort 1) and the placebo group (cohort 2) are compared to assess the protective efficacy of the vaccine against Norovirus disease overall (primary endpoint), and/or its efficacy in ameliorating the symptoms/signs (severity and # of days of illness) and/or the reduction of the presence, the amount and/or the duration of virus shedding (secondary endpoints).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

```

The invention claimed is:

1. A virus-like particle comprising at least one polypeptide having a composite amino acid sequence, wherein said composite amino acid sequence comprises SEQ ID NO: 1 or SEQ ID NO: 22, and wherein the at least one polypeptide forms a virus-like particle when expressed in a host cell.

2. The virus-like particle of claim 1, wherein the virus-like particle has antigenic properties of two or more circulating strains of a non-enveloped virus.

3. The virus-like particle of claim 1, wherein the virus-like particle provides at least a two-fold increase in antisera cross-reactivity to one or more circulating strains of a non-enveloped virus as compared to the antisera cross-reactivity obtained by immunizing with a virus-like particle containing only protein from said one or more circulating strains.

4. The virus-like particle of claim 1, further comprising a second polypeptide having a second composite amino acid sequence, wherein said second composite amino acid sequence is derived from a consensus sequence representing the capsid proteins of two or more circulating strains of a second Calicivirus, wherein the second composite sequence is derived from the consensus sequence by selecting, at each variable position where the capsid protein sequences of said two or more circulating strains differ, an amino acid present at that position in one of the said capsid protein amino acid sequences, wherein the composite sequence contains at least 1 different amino acid as compared to each of the capsid sequences of said two or more circulating strains of the second Calicivirus.

5. The virus-like particle of claim 4, wherein the composite sequence contains 5-50 different amino acids compared to the capsid sequence of one or more circulating strains of the second Calicivirus.

6. The virus-like particle of claim 4, wherein the second Calicivirus is a Norovirus.

7. The virus-like particle of claim 6, wherein the Norovirus is a genogroup I Norovirus.

8. The virus-like particle of claim 7, wherein the genogroup I Norovirus is selected from the group consisting of Norwalk virus, Southampton virus, Hesse virus, and Chiba virus.

9. The virus-like particle of claim 4, wherein the virus-like particle has antigenic properties of the two or more circulating strains of the first Calicivirus and the two or more circulating strains of the second Calicivirus.

10. The virus-like particle of claim 1, wherein the polypeptide comprises a composite amino acid sequence encoded by a nucleic acid sequence of SEQ ID NO: 3.

11. A vaccine formulation comprising the virus-like particle of claim 1.

12. A vaccine formulation comprising the virus-like particle of claim 1 and a second virus-like particle, wherein said second virus-like particle comprises a capsid protein from a Norovirus.

13. The vaccine formulation of claim 12, wherein said Norovirus is a genogroup I or genogroup II Norovirus.

14. The vaccine formulation of claim 11 further comprising an adjuvant.

15. The vaccine formulation of claim 14, wherein the adjuvant is selected from the group consisting of toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly (lactide-co-glycolides) (PLG) microparticles, poloxamer particles, microparticles, liposomes, oil-in-water emulsion, MF59, and squalene.

16. The vaccine formulation of claim 14, further comprising a delivery agent.

17. The vaccine formulation of claim 16, wherein the delivery agent is a mucoadhesive.

18. The vaccine formulation of claim 17, wherein the mucoadhesive is selected from the group consisting of glycosaminoglycans, carbohydrate polymers, polyvinyl alcohol, polyvinyl pyrollidone, polysaccharides, polyions, cellulose derivatives, proteins, and deoxyribonucleic acid.

19. The vaccine formulation of claim 18, wherein the mucoadhesive is a polysaccharide.

20. The vaccine formulation of claim 19, wherein said polysaccharide is chitosan, chitosan salt, or chitosan base.

21. The vaccine formulation of claim 14, wherein the vaccine formulation is a liquid formulation.

22. The vaccine formulation of claim 14, wherein the vaccine formulation is a dry powder formulation.

23. The dry powder formulation of claim 22 in combination with one or more devices for administering one or more doses of said formulation.

24. The dry powder formulation of claim 23, wherein said one or more doses are unit doses.

25. The dry powder formulation of claim 23, wherein the device is a single-use nasal administration device.

26. The vaccine formulation of claim 11, wherein said formulation is administered to a subject by a route selected from the group consisting of mucosal, intramuscular, intravenous, subcutaneous, intradermal, subdermal, and transdermal routes of administration.

27. The vaccine formulation of claim 26, wherein said mucosal administration is intranasal, oral, or vaginal.

28. The vaccine formulation of claim 27, wherein the formulation is in the form of a nasal spray, nasal drops or dry powder.

29. A method of inducing a protective immunity to a viral infection in a subject comprising administering to the subject the vaccine formulation of claim 11.

30. The method of claim 29, wherein the viral infection is a Norovirus infection.

31. The method of claim 30, wherein said vaccine formulation confers protection from one or more symptoms of Norovirus infection.

32. A method of making a virus-like particle comprising:
aligning amino acid sequences of capsid proteins from two or more circulating strains of a non-enveloped virus;
determining a consensus sequence from said aligned amino acid sequences;
preparing a composite sequence based on said consensus sequence that contains at least 1 different amino acid as compared to each of the capsid sequences of said two or more circulating strains; and
expressing said composite sequence in a host cell, thereby producing a virus-like particle.

33. The method of claim 32, wherein the non-enveloped virus is a Calicivirus.

34. The method of claim 33, wherein the Calicivirus is a Norovirus or Sapovirus.

35. The method of claim 34, wherein the Norovirus is a genogroup I or genogroup II Norovirus.

* * * * *

                              SEQUENCE LISTING

<160> NUMBER OF SEQ ID NOS: 22

<210> SEQ ID NO 1
<211> LENGTH: 539
<212> TYPE: PRT
<213> ORGANISM: Artificial Sequence
<220> FEATURE:
<223> OTHER INFORMATION: Composite GII.4 Norovirus VP1 amino acid
      sequence

<400> SEQUENCE: 1

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270
```

```
Leu Gly Thr Thr Gln Leu Ser Pro Val Asn Ile Cys Thr Phe Arg Gly
            275                 280                 285

Asp Val Thr His Ile Ala Gly Thr Gln Glu Tyr Thr Met Asn Leu Ala
        290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Lys Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala
    530                 535
```

<210> SEQ ID NO 2
<211> LENGTH: 539
<212> TYPE: PRT
<213> ORGANISM: Artificial Sequence
<220> FEATURE:
<223> OTHER INFORMATION: Consensus GII.4 VP1 amino acid sequence
<220> FEATURE:
<221> NAME/KEY: misc_feature
<222> LOCATION: (6)..(6)
<223> OTHER INFORMATION: Xaa may be Ser or Asn
<220> FEATURE:
<221> NAME/KEY: misc_feature
<222> LOCATION: (9)..(9)
<223> OTHER INFORMATION: Xaa may be Ser or Asn
<220> FEATURE:
<221> NAME/KEY: misc_feature
<222> LOCATION: (15)..(15)
<223> OTHER INFORMATION: Xaa may be Thr or Ala
<220> FEATURE:
<221> NAME/KEY: misc_feature
<222> LOCATION: (174)..(174)
<223> OTHER INFORMATION: Xaa may be Ser or Pro
<220> FEATURE:
<221> NAME/KEY: misc_feature
<222> LOCATION: (193)..(193)
<223> OTHER INFORMATION: Xaa may be Asp or Glu
<220> FEATURE:

```
<221> NAME/KEY: misc_feature
<222> LOCATION: (228)..(228)
<223> OTHER INFORMATION: Xaa may be Ser or Thr
<220> FEATURE:
<221> NAME/KEY: misc_feature
<222> LOCATION: (255)..(255)
<223> OTHER INFORMATION: Xaa may be Gly or Ser
<220> FEATURE:
<221> NAME/KEY: misc_feature
<222> LOCATION: (296)..(296)
<223> OTHER INFORMATION: Xaa may be Ser or Thr
<220> FEATURE:
<221> NAME/KEY: misc_feature
<222> LOCATION: (297)..(297)
<223> OTHER INFORMATION: Xaa may be Gln, Arg or His
<220> FEATURE:
<221> NAME/KEY: misc_feature
<222> LOCATION: (298)..(298)
<223> OTHER INFORMATION: Xaa may be Glu, Asp or Asn
<220> FEATURE:
<221> NAME/KEY: misc_feature
<222> LOCATION: (306)..(306)
<223> OTHER INFORMATION: Xaa may be Gln or Leu
<220> FEATURE:
<221> NAME/KEY: misc_feature
<222> LOCATION: (339)..(339)
<223> OTHER INFORMATION: Xaa may be Arg or Lys
<220> FEATURE:
<221> NAME/KEY: misc_feature
<222> LOCATION: (340)..(340)
<223> OTHER INFORMATION: Xaa may be Gly or Arg
<220> FEATURE:
<221> NAME/KEY: misc_feature
<222> LOCATION: (352)..(352)
<223> OTHER INFORMATION: Xaa may be Ser or Tyr
<220> FEATURE:
<221> NAME/KEY: misc_feature
<222> LOCATION: (356)..(356)
<223> OTHER INFORMATION: Xaa may be Val or Ala
<220> FEATURE:
<221> NAME/KEY: misc_feature
<222> LOCATION: (357)..(357)
<223> OTHER INFORMATION: Xaa may be Pro or His
<220> FEATURE:
<221> NAME/KEY: misc_feature
<222> LOCATION: (364)..(364)
<223> OTHER INFORMATION: Xaa may be Ser or Arg
<220> FEATURE:
<221> NAME/KEY: misc_feature
<222> LOCATION: (365)..(365)
<223> OTHER INFORMATION: Xaa may be Val or Ile
<220> FEATURE:
<221> NAME/KEY: misc_feature
<222> LOCATION: (368)..(368)
<223> OTHER INFORMATION: Xaa may be Ser or Thr
<220> FEATURE:
<221> NAME/KEY: misc_feature
<222> LOCATION: (372)..(372)
<223> OTHER INFORMATION: Xaa may be Ser, Glu or Asn
<220> FEATURE:
<221> NAME/KEY: misc_feature
<222> LOCATION: (375)..(375)
<223> OTHER INFORMATION: Xaa may be Phe or Leu
<220> FEATURE:
<221> NAME/KEY: misc_feature
<222> LOCATION: (378)..(378)
<223> OTHER INFORMATION: Xaa may be Gly or His
<220> FEATURE:
<221> NAME/KEY: misc_feature
<222> LOCATION: (382)..(382)
<223> OTHER INFORMATION: Xaa may be Arg or Lys
<220> FEATURE:
<221> NAME/KEY: misc_feature
<222> LOCATION: (389)..(389)
<223> OTHER INFORMATION: Xaa may be Val or Ile
<220> FEATURE:
<221> NAME/KEY: misc_feature
<222> LOCATION: (393)..(393)
<223> OTHER INFORMATION: Xaa may be Ser or Asn
```

```
<220> FEATURE:
<221> NAME/KEY: misc_feature
<222> LOCATION: (394)..(394)
<223> OTHER INFORMATION: Xaa may be Ser or Thr
<220> FEATURE:
<221> NAME/KEY: misc_feature
<222> LOCATION: (395)..(395)
<223> OTHER INFORMATION: Xaa may be Ala or Thr
<220> FEATURE:
<221> NAME/KEY: misc_feature
<222> LOCATION: (397)..(397)
<223> OTHER INFORMATION: Xaa may be Gln or Arg
<220> FEATURE:
<221> NAME/KEY: misc_feature
<222> LOCATION: (407)..(407)
<223> OTHER INFORMATION: Xaa may be Asp, Ser or Asn
<220> FEATURE:
<221> NAME/KEY: misc_feature
<222> LOCATION: (412)..(412)
<223> OTHER INFORMATION: Xaa may be Asp, Asn or Thr
<220> FEATURE:
<221> NAME/KEY: misc_feature
<222> LOCATION: (413)..(413)
<223> OTHER INFORMATION: Xaa may be Ser, Val or Gly
<220> FEATURE:
<221> NAME/KEY: misc_feature
<222> LOCATION: (425)..(425)
<223> OTHER INFORMATION: Xaa may be Ser or Thr
<220> FEATURE:
<221> NAME/KEY: misc_feature
<222> LOCATION: (448)..(448)
<223> OTHER INFORMATION: Xaa may be Asn or Asp
<220> FEATURE:
<221> NAME/KEY: misc_feature
<222> LOCATION: (459)..(459)
<223> OTHER INFORMATION: Xaa may be Gln or Leu
<220> FEATURE:
<221> NAME/KEY: misc_feature
<222> LOCATION: (504)..(504)
<223> OTHER INFORMATION: Xaa may be Gln or Pro
<220> FEATURE:
<221> NAME/KEY: misc_feature
<222> LOCATION: (534)..(534)
<223> OTHER INFORMATION: Xaa may be Thr or Ala

<400> SEQUENCE: 2

Met Lys Met Ala Ser Xaa Asp Ala Xaa Pro Ser Asp Gly Ser Xaa Ala
1               5                   10                  15

Asn Leu Val Pro Glu Val Asn Glu Val Met Ala Leu Glu Pro Val
                20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
        50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Xaa Thr Ile
                165                 170                 175
```

Lys Leu Ile Ala Met Leu Tyr Thr Pro Leu Arg Ala Asn Asn Ala Gly
            180                 185                 190

Xaa Asp Val Phe Thr Val Ser Cys Arg Val Leu Thr Arg Pro Ser Pro
    195                 200                 205

Asp Phe Asp Phe Ile Phe Leu Val Pro Thr Val Glu Ser Arg Thr
210                 215                 220

Lys Pro Phe Xaa Val Pro Ile Leu Thr Val Glu Glu Met Thr Asn Ser
225                 230                 235                 240

Arg Phe Pro Ile Pro Leu Glu Lys Leu Phe Thr Gly Pro Ser Xaa Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Xaa Xaa Xaa Tyr Thr Met Asn Leu Ala
    290                 295                 300

Ser Xaa Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Xaa Xaa Asp Gly Ser Thr Arg Gly His Lys Ala Thr Val Xaa
            340                 345                 350

Thr Gly Ser Xaa Xaa Phe Thr Pro Lys Leu Gly Xaa Xaa Gln Phe Xaa
        355                 360                 365

Thr Asp Thr Xaa Asn Asp Xaa Glu Thr Xaa Gln Asn Thr Xaa Phe Thr
    370                 375                 380

Pro Val Gly Val Xaa Gln Asp Gly Xaa Xaa Xaa His Xaa Asn Glu Pro
385                 390                 395                 400

Gln Gln Trp Val Leu Pro Xaa Tyr Ser Gly Arg Xaa Xaa His Asn Val
                405                 410                 415

His Leu Ala Pro Ala Val Ala Pro Xaa Phe Pro Gly Glu Gln Leu Leu
            420                 425                 430

Phe Phe Arg Ser Thr Met Pro Gly Cys Ser Gly Tyr Pro Asn Met Xaa
        435                 440                 445

Leu Asp Cys Leu Leu Pro Gln Glu Trp Val Xaa His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Xaa His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Xaa Gly Arg Arg Arg Ala
    530                 535

<210> SEQ ID NO 3
<211> LENGTH: 1789
<212> TYPE: DNA
<213> ORGANISM: Artificial Sequence
<220> FEATURE:
<223> OTHER INFORMATION: Composite GII.4 Norovirus VP1 DNA sequence

<400> SEQUENCE: 3

-continued

```
ttaattaagc ggccgccccc ttcaccatga agatggcttc ctccgacgct aaccccctccg      60 acggttccac cgctaacctg gtgcccgagg tgaacaacga ggtgatggct ctcgagcccg     120
tggtgggcgc tgctatcgct gctcccgtgg ctggccagca gaacgtgatc gaccccctgga   180 tccgtaacaa cttcgtgcag gctcccgtgg gcgagttcac cgtgtccccc gtaacgctc     240 ccggcgagat cctgtggtcc gctcccctgg tcccgacct gaaccccctac ctgtcccacc    300 tggctcgtat gtacaacggt tacgctggcg gtttcgaggt gcaggtgatc ctggctggta   360
acgctttcac cgctggcaag atcatcttcg ctgctgtgcc ccccaacttc cccaccgagg   420
gcctgagccc ctcccaggtg accatgttcc cccacatcat cgtggacgtg cgccagctcg   480
agcctgtgct gatcccctg cccgacgtgc gcaacaactt ctaccactac aaccagtcca   540
acgaccccac catcaagctg atcgctatgc tgtacacccc cctgcgtgct aacaacgctg   600
gtgacgacgt gttcactgtg tcctgccgtg tgctgacccg tccctccccc gacttcgact   660
tcatcttcct ggtgccccct accgtggagt cccgtaccaa gcccttcacc gtgcccatcc    720
tgaccgtgga ggagatgacc aactcccgtt tccccatccc cctcgagaag ctgttcaccg   780
gtccctccgg tgctttcgtg gtgcagcccc agaacggtcg ttgcaccacc gacggtgtcc   840
tgctgggcac cactcagctg tcccccgtga acatctgcac cttccgtggt gacgtgaccc   900
acatcgctgg cacccaagag tacaccatga acctggcctc ccagaactgg aacaactacg    960
accctaccga ggagatcccc gctcctctgg gcacccctga cttcgtgggc aagatccagg   1020
gtgtcctgac ccagaccacc cgcggtgacg gctccacccg tggtcacaag gctaccgtgt   1080
ccaccggttc cgtgcacttc acccccaagc tgggttccgt ccagttctcc accgacacct   1140
ccaacgactt cgagactggc cagaacacca agttcacccc cgtgggtgtg gtgcaggacg   1200
gttctaccac ccaccagaac gagccccagc agtgggtgct gctgactac tccggtcgtg     1260 actcccacaa cgtgcacctg ctcccgctg tggctcccac cttccccggc gagcagctgc    1320
tgttcttccg ttccaccatg cccggttgct ccggttaccc caacatgaac ctcgactgcc   1380
tgctgcctca ggagtgggtc cagcacttct accaggaggc tgctccccgct cagtccgacg   1440 tggctctgct gcgtttcgtg aaccccgaca ccggtcgtgt gctgttcgag tgcaagctgc   1500
acaagtccgg ttacgtgacc gtggctcaca ccggccagca cgacctggtg atccctccca   1560
acggttactt ccgtttcgac tcctgggtga ccagttcta cacctggct cccatgggta    1620 acggcaccgg tcgtcgtcgt gctctgtaat ggctggagct ttctttgctg gattggcatc   1680
tgatgtcctt ggctctggac ttggttccct aatcaatgc ggggctgggg ccatcaacca   1740
aaaagttgaa tttgaaaata acagaaaatt gcaacaagct tggcgcgcc              1789
```

<210> SEQ ID NO 4
<211> LENGTH: 539
<212> TYPE: PRT
<213> ORGANISM: Norovirus Norwalk virus sp.

<400> SEQUENCE: 4

```
Met Lys Met Ala Ser Ser Asp Ala Ser Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
```

```
            50                  55                  60
Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
                100                 105                 110

Ala Phe Thr Ala Gly Lys Ile Ile Phe Ala Ala Val Pro Pro Asn Phe
                115                 120                 125

Pro Thr Glu Gly Leu Ser Pro Ser Gln Val Thr Met Phe Pro His Ile
            130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
                195                 200                 205

Asp Phe Asp Phe Ile Phe Leu Val Pro Pro Thr Val Glu Ser Arg Thr
            210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
            275                 280                 285

Asp Val Thr His Ile Ala Gly Thr His Asp Tyr Thr Met Asn Leu Ala
            290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
                340                 345                 350

Thr Gly Ser Val His Phe Thr Pro Lys Leu Gly Ser Val Gln Phe Thr
            355                 360                 365

Thr Asp Thr Asn Asn Asp Leu Glu Thr Gly Gln Asn Thr Lys Phe Thr
            370                 375                 380

Pro Val Gly Val Val Gln Asp Gly Asn Ser Ala His Gln Asn Glu Pro
385                 390                 395                 400

Gln Gln Trp Val Leu Pro Asn Tyr Ser Gly Arg Thr Gly His Asn Val
                405                 410                 415

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asn
            435                 440                 445

Leu Asp Cys Leu Leu Pro Gln Glu Trp Val Leu His Phe Tyr Gln Glu
            450                 455                 460

Ala Ala Pro Ala Gln Ser Asp Val Ala Leu Leu Arg Phe Val Asn Pro
465                 470                 475                 480
```

```
Asp Thr Gly Arg Val Leu Phe Glu Cys Lys Leu His Lys Ser Gly Tyr
            485                 490                 495

Val Thr Val Ala His Thr Gly Pro His Asp Leu Val Ile Pro Pro Asn
            500                 505                 510

Gly Tyr Phe Arg Phe Asp Ser Trp Val Asn Gln Phe Tyr Thr Leu Ala
            515                 520                 525

Pro Met Gly Asn Gly Ala Gly Arg Arg Arg Ala
            530                 535

<210> SEQ ID NO 5
<211> LENGTH: 539
<212> TYPE: PRT
<213> ORGANISM: Norovirus Norwalk virus sp.

<400> SEQUENCE: 5

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
            35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
            85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
            115                 120                 125

Pro Thr Glu Gly Leu Ser Pro Ser Gln Val Thr Met Phe Pro His Ile
            130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
            165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
            195                 200                 205

Asp Phe Asp Phe Ile Phe Leu Val Pro Pro Thr Val Glu Ser Arg Thr
            210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
            245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
            275                 280                 285

Asp Val Thr His Ile Ala Gly Thr Gln Glu Tyr Thr Met Asn Leu Ala
            290                 295                 300

Ser Gln Asn Trp Asn Asn Tyr Asp Pro Thr Glu Glu Ile Pro Ala Pro
```

```
                305                 310                 315                 320
Leu Gly Thr Pro Asp Phe Val Gly Lys Ile Gln Gly Val Leu Thr Gln
                325                 330                 335
Thr Thr Arg Arg Asp Gly Ser Thr Arg Gly His Lys Ala Thr Val Ser
                340                 345                 350
Thr Gly Ser Val His Phe Thr Pro Lys Leu Gly Arg Ile Gln Phe Ser
                355                 360                 365
Thr Asp Thr Ser Asn Asp Phe Glu Thr Gly Gln Asn Thr Arg Phe Thr
                370                 375                 380
Pro Val Gly Val Val Gln Asp Gly Ser Thr Thr His Gln Asn Glu Pro
385                 390                 395                 400
Gln Gln Trp Val Leu Pro Asp Tyr Ser Gly Arg Asp Ser His Asn Val
                405                 410                 415
His Leu Ala Pro Ala Val Ala Pro Ser Phe Pro Gly Glu Gln Leu Leu
                420                 425                 430
Phe Phe Arg Ser Thr Met Pro Gly Cys Ser Gly Tyr Pro Asn Met Asn
                435                 440                 445
Leu Asp Cys Leu Leu Pro Gln Glu Trp Val Gln His Phe Tyr Gln Glu
                450                 455                 460
Ala Ala Pro Ala Gln Ser Asp Val Ala Leu Leu Arg Phe Val Asn Pro
465                 470                 475                 480
Asp Thr Gly Arg Val Leu Phe Glu Cys Lys Leu His Lys Ser Gly Tyr
                485                 490                 495
Val Thr Val Ala His Thr Gly Gln His Asp Leu Val Ile Pro Pro Asn
                500                 505                 510
Gly Tyr Phe Arg Phe Asp Ser Trp Val Asn Gln Phe Tyr Thr Leu Ala
                515                 520                 525
Pro Met Gly Asn Gly Thr Gly Arg Arg Arg Ala
                530                 535

<210> SEQ ID NO 6
<211> LENGTH: 539
<212> TYPE: PRT
<213> ORGANISM: Norovirus Norwalk virus sp.

<400> SEQUENCE: 6

Met Lys Met Ala Ser Asn Asp Ala Asn Pro Ser Asp Gly Ser Ala Ala
1               5                   10                  15
Asn Leu Val Pro Glu Val Asn Asn Glu Val Met Ala Leu Glu Pro Val
                20                  25                  30
Val Gly Ala Ala Ile Ala Ala Pro Val Ala Gly Gln Gln Asn Val Ile
                35                  40                  45
Asp Pro Trp Ile Arg Asn Asn Phe Val Gln Ala Pro Gly Gly Glu Phe
                50                  55                  60
Thr Val Ser Pro Arg Asn Ala Pro Gly Glu Ile Leu Trp Ser Ala Pro
65                  70                  75                  80
Leu Gly Pro Asp Leu Asn Pro Tyr Leu Ser His Leu Ala Arg Met Tyr
                85                  90                  95
Asn Gly Tyr Ala Gly Gly Phe Glu Val Gln Val Ile Leu Ala Gly Asn
                100                 105                 110
Ala Phe Thr Ala Gly Lys Ile Ile Phe Ala Ala Val Pro Pro Asn Phe
                115                 120                 125
Pro Thr Glu Gly Leu Ser Pro Ser Gln Val Thr Met Phe Pro His Ile
                130                 135                 140
```

-continued

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
            165                 170                 175

Lys Leu Ile Ala Met Leu Tyr Thr Pro Leu Arg Ala Asn Asn Ala Gly
        180                 185                 190

Glu Asp Val Phe Thr Val Ser Cys Arg Val Leu Thr Arg Pro Ser Pro
    195                 200                 205

Asp Phe Asp Phe Ile Phe Leu Val Pro Pro Thr Val Glu Ser Arg Thr
210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
            245                 250                 255

Phe Val Val Gln Pro Gln Asn Gly Arg Cys Thr Thr Asp Gly Val Leu
        260                 265                 270

Leu Gly Thr Thr Gln Leu Ser Pro Val Asn Ile Cys Thr Phe Arg Gly
    275                 280                 285

Asp Val Thr His Ile Ala Gly Ser Arg Asn Tyr Thr Met Asn Leu Ala
290                 295                 300

Ser Leu Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
            325                 330                 335

Thr Thr Lys Gly Asp Gly Ser Thr Arg Gly His Lys Ala Thr Val Tyr
        340                 345                 350

Thr Gly Ser Ala Pro Phe Thr Pro Lys Leu Gly Ser Val Gln Phe Ser
    355                 360                 365

Thr Asp Thr Glu Asn Asp Phe Glu Thr His Gln Asn Thr Lys Phe Thr
370                 375                 380

Pro Val Gly Val Ile Gln Asp Gly Ser Thr Thr His Arg Asn Glu Pro
385                 390                 395                 400

Gln Gln Trp Val Leu Pro Ser Tyr Ser Gly Arg Asn Val His Asn Val
            405                 410                 415

His Leu Ala Pro Ala Val Ala Pro Thr Phe Pro Gly Glu Gln Leu Leu
        420                 425                 430

Phe Phe Arg Ser Thr Met Pro Gly Cys Ser Gly Tyr Pro Asn Met Asp
    435                 440                 445

Leu Asp Cys Leu Leu Pro Gln Glu Trp Val Gln His Phe Tyr Gln Glu
450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
            485                 490                 495

Val Thr Val Ala His Thr Gly Gln His Asp Leu Val Ile Pro Pro Asn
        500                 505                 510

Gly Tyr Phe Arg Phe Asp Ser Trp Val Asn Gln Phe Tyr Thr Leu Ala
    515                 520                 525

Pro Met Gly Asn Gly Thr Gly Arg Arg Ala
530                 535

<210> SEQ ID NO 7
<211> LENGTH: 539
<212> TYPE: PRT

```
<213> ORGANISM: Artificial Sequence
<220> FEATURE:
<223> OTHER INFORMATION: Consensus GII VP1 amino acid sequence
<220> FEATURE:
<221> NAME/KEY: misc_feature
<222> LOCATION: (22)..(22)
<223> OTHER INFORMATION: Xaa may be Val, Ser or Thr
<220> FEATURE:
<221> NAME/KEY: misc_feature
<222> LOCATION: (26)..(26)
<223> OTHER INFORMATION: Xaa may be Thr, Val or Ala
<220> FEATURE:
<221> NAME/KEY: misc_feature
<222> LOCATION: (45)..(45)
<223> OTHER INFORMATION: Xaa may be Asn, Thr or Gln
<220> FEATURE:
<221> NAME/KEY: misc_feature
<222> LOCATION: (54)..(54)
<223> OTHER INFORMATION: Xaa may be Met, Ala, or Asn
<220> FEATURE:
<221> NAME/KEY: misc_feature
<222> LOCATION: (103)..(103)
<223> OTHER INFORMATION: Xaa may be Val, Met or Phe
<220> FEATURE:
<221> NAME/KEY: misc_feature
<222> LOCATION: (108)..(108)
<223> OTHER INFORMATION: Xaa may be Leu, Met or Val
<220> FEATURE:
<221> NAME/KEY: misc_feature
<222> LOCATION: (131)..(131)
<223> OTHER INFORMATION: Xaa may be Gly, Glu or Asp
<220> FEATURE:
<221> NAME/KEY: misc_feature
<222> LOCATION: (136)..(136)
<223> OTHER INFORMATION: Xaa may be Gly, Gln or Ala
<220> FEATURE:
<221> NAME/KEY: misc_feature
<222> LOCATION: (171)..(171)
<223> OTHER INFORMATION: Xaa may be Glu, Lys or Gly
<220> FEATURE:
<221> NAME/KEY: misc_feature
<222> LOCATION: (172)..(172)
<223> OTHER INFORMATION: Xaa may be Pro, Asp or Ser
<220> FEATURE:
<221> NAME/KEY: misc_feature
<222> LOCATION: (248)..(248)
<223> OTHER INFORMATION: Xaa may be Glu, Gln or Ser
<220> FEATURE:
<221> NAME/KEY: misc_feature
<222> LOCATION: (256)..(256)
<223> OTHER INFORMATION: Xaa may be Gly, Val or Asn
<220> FEATURE:
<221> NAME/KEY: misc_feature
<222> LOCATION: (266)..(266)
<223> OTHER INFORMATION: Xaa may be Ser, Cys or Val
<220> FEATURE:
<221> NAME/KEY: misc_feature
<222> LOCATION: (273)..(273)
<223> OTHER INFORMATION: Xaa may be Leu, Gln or Met
<220> FEATURE:
<221> NAME/KEY: misc_feature
<222> LOCATION: (279)..(279)
<223> OTHER INFORMATION: Xaa may be Val, Gln or Leu
<220> FEATURE:
<221> NAME/KEY: misc_feature
<222> LOCATION: (282)..(282)
<223> OTHER INFORMATION: Xaa may be Asn, Gly or Gln
<220> FEATURE:
<221> NAME/KEY: misc_feature
<222> LOCATION: (289)..(289)
<223> OTHER INFORMATION: Xaa may be Glu or Thr
<220> FEATURE:
<221> NAME/KEY: misc_feature
<222> LOCATION: (290)..(290)
<223> OTHER INFORMATION: Xaa may be Val or Leu
<220> FEATURE:
<221> NAME/KEY: misc_feature
<222> LOCATION: (293)..(293)
<223> OTHER INFORMATION: Xaa may be Ile or Ser
```

```
<220> FEATURE:
<221> NAME/KEY: misc_feature
<222> LOCATION: (294)..(294)
<223> OTHER INFORMATION: Xaa may be Asn or Thr
<220> FEATURE:
<221> NAME/KEY: misc_feature
<222> LOCATION: (301)..(301)
<223> OTHER INFORMATION: Xaa may be Asp or Ala
<220> FEATURE:
<221> NAME/KEY: misc_feature
<222> LOCATION: (303)..(303)
<223> OTHER INFORMATION: Xaa may be Gln, Asp or Asn
<220> FEATURE:
<221> NAME/KEY: misc_feature
<222> LOCATION: (310)..(310)
<223> OTHER INFORMATION: Xaa may be Val, Ile or Leu
<220> FEATURE:
<221> NAME/KEY: misc_feature
<222> LOCATION: (321)..(321)
<223> OTHER INFORMATION: Xaa may be Thr, Ser or Ala
<220> FEATURE:
<221> NAME/KEY: misc_feature
<222> LOCATION: (334)..(334)
<223> OTHER INFORMATION: Xaa may be Leu, Gln or Arg
<220> FEATURE:
<221> NAME/KEY: misc_feature
<222> LOCATION: (336)..(336)
<223> OTHER INFORMATION: Xaa may be Asn, Arg or Lys
<220> FEATURE:
<221> NAME/KEY: misc_feature
<222> LOCATION: (341)..(341)
<223> OTHER INFORMATION: Xaa may be Thr, Ile or Ala
<220> FEATURE:
<221> NAME/KEY: misc_feature
<222> LOCATION: (350)..(350)
<223> OTHER INFORMATION: Xaa may be Cys, Asn or Thr
<220> FEATURE:
<221> NAME/KEY: misc_feature
<222> LOCATION: (356)..(356)
<223> OTHER INFORMATION: Xaa may be Ile, Val or Lys
<220> FEATURE:
<221> NAME/KEY: misc_feature
<222> LOCATION: (358)..(358)
<223> OTHER INFORMATION: Xaa may be Ala, Pro or Asp
<220> FEATURE:
<221> NAME/KEY: misc_feature
<222> LOCATION: (360)..(360)
<223> OTHER INFORMATION: Xaa may be Trp, Tyr or Thr
<220> FEATURE:
<221> NAME/KEY: misc_feature
<222> LOCATION: (362)..(362)
<223> OTHER INFORMATION: Xaa may be Pro, Ala, or Asp
<220> FEATURE:
<221> NAME/KEY: misc_feature
<222> LOCATION: (363)..(363)
<223> OTHER INFORMATION: Xaa may be Lys, Gln or Arg
<220> FEATURE:
<221> NAME/KEY: misc_feature
<222> LOCATION: (372)..(372)
<223> OTHER INFORMATION: Xaa may be Val, Gln or Glu
<220> FEATURE:
<221> NAME/KEY: misc_feature
<222> LOCATION: (378)..(378)
<223> OTHER INFORMATION: Xaa may be Asp, Thr or Ser
<220> FEATURE:
<221> NAME/KEY: misc_feature
<222> LOCATION: (379)..(379)
<223> OTHER INFORMATION: Xaa may be Arg, Asp or Gly
<220> FEATURE:
<221> NAME/KEY: misc_feature
<222> LOCATION: (383)..(383)
<223> OTHER INFORMATION: Xaa may be Ile, Val or Thr
<220> FEATURE:
<221> NAME/KEY: misc_feature
<222> LOCATION: (395)..(395)
<223> OTHER INFORMATION: Xaa may be Tyr, Asn or Asp
<220> FEATURE:
<221> NAME/KEY: misc_feature
<222> LOCATION: (398)..(398)
```

-continued

<223> OTHER INFORMATION: Xaa may be Asp, Glu or Ala
<220> FEATURE:
<221> NAME/KEY: misc_feature
<222> LOCATION: (407)..(407)
<223> OTHER INFORMATION: Xaa may be Tyr, Arg or Asn
<220> FEATURE:
<221> NAME/KEY: misc_feature
<222> LOCATION: (425)..(425)
<223> OTHER INFORMATION: Xaa may be Leu, Val or Asn
<220> FEATURE:
<221> NAME/KEY: misc_feature
<222> LOCATION: (437)..(437)
<223> OTHER INFORMATION: Xaa may be His, Tyr or Gln
<220> FEATURE:
<221> NAME/KEY: misc_feature
<222> LOCATION: (444)..(444)
<223> OTHER INFORMATION: Xaa may be Tyr, Thr or Arg
<220> FEATURE:
<221> NAME/KEY: misc_feature
<222> LOCATION: (469)..(469)
<223> OTHER INFORMATION: Xaa may be Ser Met or Gln
<220> FEATURE:
<221> NAME/KEY: misc_feature
<222> LOCATION: (471)..(471)
<223> OTHER INFORMATION: Xaa may be Asp, Glu or Gln
<220> FEATURE:
<221> NAME/KEY: misc_feature
<222> LOCATION: (478)..(478)
<223> OTHER INFORMATION: Xaa may be Thr, Ile or Val
<220> FEATURE:
<221> NAME/KEY: misc_feature
<222> LOCATION: (494)..(494)
<223> OTHER INFORMATION: Xaa may be Gln, Ala or Leu
<220> FEATURE:
<221> NAME/KEY: misc_feature
<222> LOCATION: (501)..(501)
<223> OTHER INFORMATION: Xaa may be Asn, Ser or Lys
<220> FEATURE:
<221> NAME/KEY: misc_feature
<222> LOCATION: (505)..(505)
<223> OTHER INFORMATION: Xaa may be Arg, Ala or Ser

<400> SEQUENCE: 7

Met Lys Met Ala Ser Asn Asp Ala Ala Pro Ser Asn Asp Gly Ala Ala
1               5                   10                  15

Gly Leu Val Pro Glu Xaa Asn Asn Glu Xaa Met Ala Leu Glu Pro Val
            20                  25                  30

Ala Gly Ala Ala Ile Ala Ala Pro Leu Thr Gly Gln Xaa Asn Ile Ile
        35                  40                  45

Asp Pro Trp Ile Arg Xaa Asn Phe Val Gln Ala Pro Asn Gly Glu Phe
50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Xaa Glu Val Gln Val Xaa Leu Ala Gly Asn
            100                 105                 110

Ala Phe Thr Ala Gly Lys Leu Val Phe Ala Ala Ile Pro Pro His Phe
        115                 120                 125

Pro Ile Xaa Asn Leu Ser Pro Xaa Gln Ile Thr Met Phe Pro His Val
130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Xaa Xaa Asp Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
210                 215                 220

Lys Pro Phe Thr Leu Pro Ile Leu Thr Ile Gly Glu Leu Ser Asn Ser
225                 230                 235                 240

Arg Phe Pro Val Pro Ile Asp Xaa Leu Tyr Thr Ser Pro Asn Glu Xaa
                245                 250                 255

Ile Val Val Gln Cys Gln Asn Gly Arg Xaa Thr Leu Asp Gly Glu Leu
                260                 265                 270

Xaa Gly Thr Thr Gln Leu Xaa Pro Ser Xaa Ile Cys Ala Phe Arg Gly
            275                 280                 285

Xaa Xaa Thr Arg Xaa Xaa Ala His Leu Ser Asp Gln Xaa Asn Xaa His
        290                 295                 300

Arg Trp Asn Ile Gln Xaa Thr Asn Leu Asn Gly Thr Pro Phe Asp Pro
305                 310                 315                 320

Xaa Glu Asp Ile Pro Ala Pro Leu Gly Thr Pro Asp Phe Xaa Gly Xaa
                325                 330                 335

Val Phe Gly Val Xaa Ser Gln Arg Asn Pro Asp Asn Thr Xaa Arg Ala
            340                 345                 350

His Asp Ala Xaa Val Xaa Thr Xaa Ser Xaa Xaa Phe Thr Pro Lys Leu
        355                 360                 365

Gly Ser Val Xaa Ile Gly Thr Trp Glu Xaa Xaa Asp Phe Asp Xaa Asn
        370                 375                 380

Gln Pro Thr Lys Phe Thr Pro Val Gly Leu Xaa Asp Thr Xaa His Phe
385                 390                 395                 400

Asn Gln Trp Val Leu Pro Xaa Tyr Ser Gly Ala Leu Thr Leu Asn Met
                405                 410                 415

Asn Leu Ala Pro Ser Val Ala Pro Xaa Phe Pro Gly Glu Gln Leu Leu
                420                 425                 430

Phe Phe Arg Ser Xaa Leu Pro Leu Lys Gly Gly Xaa Ser Asn Gly Ala
            435                 440                 445

Ile Asp Cys Leu Leu Pro Gln Glu Trp Val Gln His Phe Tyr Gln Glu
        450                 455                 460

Ser Ala Pro Ser Xaa Thr Xaa Val Ala Leu Val Arg Tyr Xaa Asn Pro
465                 470                 475                 480

Asp Thr Gly Arg Val Leu Phe Glu Ala Lys Leu His Arg Xaa Gly Phe
                485                 490                 495

Met Thr Val Ala Xaa Asn Gly Ser Xaa Pro Ile Val Val Pro Pro Asn
                500                 505                 510

Gly Tyr Phe Arg Phe Asp Ser Trp Val Asn Gln Phe Tyr Ser Leu Ala
                515                 520                 525

Pro Met Gly Thr Gly Asn Gly Arg Arg Arg Ile
        530                 535

<210> SEQ ID NO 8
<211> LENGTH: 534
<212> TYPE: PRT
<213> ORGANISM: Norovirus Norwalk virus sp.

<400> SEQUENCE: 8

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val

-continued

```
                20                  25                  30
Ala Gly Ala Ser Ile Ala Ala Pro Leu Thr Gly Gln Asn Asn Val Ile
            35                  40                  45
Asp Pro Trp Ile Arg Met Asn Phe Val Gln Ala Pro Asn Gly Glu Phe
        50                  55                  60
Thr Val Ser Pro Arg Asn Ser Pro Gly Glu Ile Leu Leu Asn Leu Glu
 65                  70                  75                  80
Leu Gly Pro Glu Leu Asn Pro Phe Leu Ala His Leu Ser Arg Met Tyr
                85                  90                  95
Asn Gly Tyr Ala Gly Gly Val Glu Val Gln Val Leu Leu Ala Gly Asn
            100                 105                 110
Ala Phe Thr Ala Gly Lys Leu Val Phe Ala Ala Ile Pro Pro His Phe
        115                 120                 125
Pro Ile Gly Asn Leu Ser Pro Gly Gln Ile Ala Met Phe Pro His Val
        130                 135                 140
Ile Ile Asp Val Arg Thr Leu Glu Pro Val Leu Leu Pro Leu Pro Asp
145                 150                 155                 160
Val Arg Asn Asn Phe Phe His Tyr Asn Gln Glu Pro Glu Pro Arg Met
                165                 170                 175
Arg Leu Val Ala Met Leu Tyr Thr Pro Leu Arg Ser Asn Gly Ser Gly
            180                 185                 190
Asp Asp Val Phe Thr Val Ser Cys Arg Val Leu Thr Arg Pro Ser Pro
        195                 200                 205
Asp Phe Asp Phe Asn Tyr Leu Val Pro Pro Thr Val Glu Ser Lys Thr
        210                 215                 220
Lys Pro Phe Thr Leu Pro Ile Leu Thr Ile Gly Glu Leu Ser Asn Ser
225                 230                 235                 240
Arg Phe Pro Val Pro Ile Asp Glu Leu Tyr Thr Ser Pro Asn Glu Gly
                245                 250                 255
Leu Val Val Gln Pro Gln Asn Gly Arg Ser Thr Leu Asp Gly Glu Leu
            260                 265                 270
Leu Gly Thr Thr Gln Leu Val Pro Ser Asn Ile Cys Ser Leu Arg Gly
        275                 280                 285
Arg Ile Asn Ala His Leu Ser Asp Asn Gln His Arg Trp Asn Met Gln
        290                 295                 300
Val Thr Asn Ala Asn Gly Thr Pro Phe Asp Pro Thr Glu Asp Val Pro
305                 310                 315                 320
Ala Pro Leu Gly Thr Pro Asp Phe Leu Ala Asn Ile Tyr Gly Val Thr
                325                 330                 335
Ser Gln Arg Asn Pro Asp Asn Thr Cys Arg Ala His Asp Gly Ile Leu
            340                 345                 350
Ala Thr Trp Ser Pro Lys Phe Thr Pro Lys Leu Gly Ser Val Val Leu
        355                 360                 365
Gly Thr Trp Glu Asp Arg Asp Phe Asp Ile Asn Gln Pro Thr Arg Phe
        370                 375                 380
Thr Pro Val Gly Leu Tyr Asp Thr Asp His Phe Asn Gln Trp Val Leu
385                 390                 395                 400
Pro Tyr Tyr Ser Gly Ala Leu Thr Leu Asn Met Asn Leu Ala Pro Ser
                405                 410                 415
Val Ala Pro Leu Phe Pro Gly Glu Gln Leu Leu Phe Phe Arg Ser His
            420                 425                 430
Val Pro Leu Lys Gly Gly Thr Ser Asn Gly Ala Ile Asp Cys Leu Leu
        435                 440                 445
```

```
Pro Gln Glu Trp Val Gln His Phe Tyr Gln Glu Ser Ala Pro Ser Ser
    450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495

Ser Gly Ser Arg Pro Ile Val Val Pro Pro Asn Gly Tyr Phe Arg Phe
                500                 505                 510

Asp Ser Trp Val Asn Gln Phe Tyr Ser Leu Ala Pro Met Gly Thr Gly
                515                 520                 525

Asn Gly Arg Arg Arg Val
                530

<210> SEQ ID NO 9
<211> LENGTH: 541
<212> TYPE: PRT
<213> ORGANISM: Norovirus Norwalk virus sp.

<400> SEQUENCE: 9

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
                20                  25                  30

Ala Gly Ala Ala Leu Ala Ala Pro Val Thr Gly Gln Thr Asn Ile Ile
            35                  40                  45

Asp Pro Trp Ile Arg Ala Asn Phe Val Gln Ala Pro Asn Gly Glu Phe
50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
```

```
            275                 280                 285
Glu Val Thr Ala His Leu Gln Asp Asn Asp His Leu Tyr Asn Ile Thr
290                 295                 300
Ile Thr Asn Leu Asn Gly Ser Pro Phe Asp Pro Ser Glu Asp Ile Pro
305                 310                 315                 320
Ala Pro Leu Gly Val Pro Asp Phe Gln Gly Arg Val Phe Gly Val Ile
                325                 330                 335
Thr Gln Arg Asp Lys Gln Asn Ala Ala Gly Gln Ser Gln Pro Ala Asn
            340                 345                 350
Arg Gly His Asp Ala Val Val Pro Thr Tyr Thr Ala Gln Tyr Thr Pro
        355                 360                 365
Lys Leu Gly Gln Val Gln Ile Gly Thr Trp Gln Thr Asp Asp Leu Lys
370                 375                 380
Val Asn Gln Pro Val Lys Phe Thr Pro Val Gly Leu Asn Asp Thr Glu
385                 390                 395                 400
His Phe Asn Gln Trp Val Val Pro Arg Tyr Ala Gly Ala Leu Asn Leu
                405                 410                 415
Asn Thr Asn Leu Ala Pro Ser Val Ala Pro Val Phe Pro Gly Glu Arg
            420                 425                 430
Leu Leu Phe Phe Arg Ser Tyr Leu Pro Leu Lys Gly Gly Tyr Gly Asn
        435                 440                 445
Pro Ala Ile Asp Cys Leu Leu Pro Gln Glu Trp Val Gln His Phe Tyr
    450                 455                 460
Gln Glu Ala Ala Pro Ser Met Ser Glu Val Ala Leu Val Arg Tyr Ile
465                 470                 475                 480
Asn Pro Asp Thr Gly Arg Ala Leu Phe Glu Ala Lys Leu His Arg Ala
                485                 490                 495
Gly Phe Met Thr Val Ser Ser Asn Thr Ser Ala Pro Val Val Val Pro
            500                 505                 510
Ala Asn Gly Tyr Phe Arg Phe Asp Ser Trp Val Asn Gln Phe Tyr Ser
        515                 520                 525
Leu Ala Pro Met Gly Thr Gly Asn Gly Arg Arg Ile
530                 535                 540

<210> SEQ ID NO 10
<211> LENGTH: 547
<212> TYPE: PRT
<213> ORGANISM: Norovirus Norwalk virus sp.

<400> SEQUENCE: 10

Met Lys Met Ala Ser Asn Asp Ala Ala Pro Ser Asn Asp Gly Ala Ala
1               5                   10                  15
Gly Leu Val Pro Glu Ile Asn Asn Glu Ala Met Ala Leu Glu Pro Val
            20                  25                  30
Ala Gly Ala Ala Ile Ala Ala Pro Leu Thr Gly Gln Gln Asn Ile Ile
        35                  40                  45
Asp Pro Trp Ile Met Asn Asn Phe Val Gln Ala Pro Gly Gly Glu Phe
    50                  55                  60
Thr Val Ser Pro Arg Asn Ser Pro Gly Glu Val Leu Leu Asn Leu Glu
65                  70                  75                  80
Leu Gly Pro Glu Ile Asn Pro Tyr Leu Ala His Leu Ala Arg Met Tyr
                85                  90                  95
Asn Gly Tyr Ala Gly Gly Phe Glu Val Gln Ala Val Leu Ala Gly Asn
            100                 105                 110
```

```
Ala Phe Thr Ala Gly Lys Val Ile Phe Ala Ala Ile Pro Pro Asn Phe
            115                 120                 125

Pro Ile Asp Asn Leu Ser Ala Ala Gln Ile Thr Met Cys Pro His Val
130                 135                 140

Ile Val Asp Val Arg Gln Leu Glu Pro Ile Asn Leu Pro Met Pro Asp
145                 150                 155                 160

Val Arg Asn Asn Phe Phe His Tyr Asn Gln Gly Ser Asp Ser Arg Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
            195                 200                 205

Asp Phe Ser Phe Asn Phe Leu Val Pro Pro Thr Val Glu Ser Lys Thr
            210                 215                 220

Lys Leu Phe Thr Leu Pro Ile Leu Thr Ile Ser Glu Met Ser Asn Ser
225                 230                 235                 240

Arg Phe Pro Val Pro Ile Asp Ser Leu His Thr Ser Pro Thr Glu Asn
                245                 250                 255

Ile Val Val Gln Cys Gln Asn Gly Arg Val Thr Leu Asp Gly Glu Leu
            260                 265                 270

Met Gly Thr Thr Gln Leu Leu Pro Ser Gln Ile Cys Ala Phe Arg Gly
            275                 280                 285

Thr Leu Thr Arg Ser Thr Ser Arg Ala Ser Asp Gln Ala Asp Thr Pro
            290                 295                 300

Thr Pro Arg Leu Phe Asn His Arg Trp His Ile Gln Leu Asp Asn Leu
305                 310                 315                 320

Asn Gly Thr Pro Tyr Asp Pro Ala Glu Asp Ile Pro Ala Pro Leu Gly
                325                 330                 335

Thr Pro Asp Phe Arg Gly Lys Val Phe Gly Val Ala Ser Gln Arg Asn
            340                 345                 350

Pro Asp Ser Thr Thr Arg Ala His Glu Ala Lys Val Asp Thr Thr Ser
            355                 360                 365

Asp Arg Phe Thr Pro Lys Leu Gly Ser Leu Glu Ile Ile Thr Glu Ser
370                 375                 380

Gly Asp Phe Asp Thr Asn Gln Ser Thr Lys Phe Thr Pro Val Gly Ile
385                 390                 395                 400

Gly Val Asp Asn Glu Ala Gly Phe Gln Gln Trp Ser Leu Pro Asn Tyr
                405                 410                 415

Ser Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
            435                 440                 445

Ser Gly Gly Arg Ser Asn Gly Val Leu Asp Cys Leu Val Pro Gln Glu
450                 455                 460

Trp Val Gln His Phe Tyr Gln Glu Ser Ala Pro Ala Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Gly Phe Met Thr Ile Ala Lys Asn Gly Asp
            500                 505                 510

Ser Pro Ile Thr Val Pro Pro Asn Gly Tyr Phe Arg Phe Glu Ser Trp
            515                 520                 525

Val Asn Pro Phe Tyr Thr Leu Ala Pro Met Gly Thr Gly Asn Gly Arg
```

Arg Arg Ile
545

<210> SEQ ID NO 11
<211> LENGTH: 537
<212> TYPE: PRT
<213> ORGANISM: Artificial Sequence
<220> FEATURE:
<223> OTHER INFORMATION: Composite GII VP1 amino acid sequence

<400> SEQUENCE: 11

Met Lys Met Ala Ser Asn Asp Ala Ala Pro Ser Asn Asp Gly Ala Ala
1               5                   10                  15

Gly Leu Val Pro Glu Ser Asn Asn Glu Val Met Ala Leu Glu Pro Val

```
                340             345             350
Ala Val Val Pro Thr Tyr Ser Ala Gln Phe Thr Pro Lys Leu Gly Ser
            355                 360                 365

Val Gln Ile Gly Thr Trp Glu Thr Asp Asp Phe Asp Val Asn Gln Pro
        370                 375                 380

Thr Lys Phe Thr Pro Val Gly Leu Asn Asp Thr Glu His Phe Asn Gln
385                 390                 395                 400

Trp Val Leu Pro Arg Tyr Ser Gly Ala Leu Thr Leu Asn Met Asn Leu
                405                 410                 415

Ala Pro Ser Val Ala Pro Val Phe Pro Gly Glu Gln Leu Leu Phe Phe
            420                 425                 430

Arg Ser Tyr Leu Pro Leu Lys Gly Gly Tyr Ser Asn Gly Ala Ile Asp
            435                 440                 445

Cys Leu Leu Pro Gln Glu Trp Val Gln His Phe Tyr Gln Glu Ser Ala
        450                 455                 460

Pro Ser Met Thr Glu Val Ala Leu Val Arg Tyr Ile Asn Pro Asp Thr
465                 470                 475                 480

Gly Arg Val Leu Phe Glu Ala Lys Leu His Arg Ala Gly Phe Met Thr
                485                 490                 495

Val Ala Ser Asn Gly Ser Ala Pro Ile Val Val Pro Pro Asn Gly Tyr
            500                 505                 510

Phe Arg Phe Asp Ser Trp Val Asn Gln Phe Tyr Ser Leu Ala Pro Met
            515                 520                 525

Gly Thr Gly Asn Gly Arg Arg Arg Ile
        530                 535

<210> SEQ ID NO 12
<211> LENGTH: 544
<212> TYPE: PRT
<213> ORGANISM: Artificial Sequence
<220> FEATURE:
<223> OTHER INFORMATION: Consensus GI sequence
<220> FEATURE:
<221> NAME/KEY: misc_feature
<222> LOCATION: (10)..(10)
<223> OTHER INFORMATION: Xaa may be Ser Gln or Pro
<220> FEATURE:
<221> NAME/KEY: misc_feature
<222> LOCATION: (51)..(51)
<223> OTHER INFORMATION: Xaa may be Pro, Met or Leu
<220> FEATURE:
<221> NAME/KEY: misc_feature
<222> LOCATION: (112)..(112)
<223> OTHER INFORMATION: Xaa may be Met, Leu or Val
<220> FEATURE:
<221> NAME/KEY: misc_feature
<222> LOCATION: (133)..(133)
<223> OTHER INFORMATION: Xaa may be Gly, Thr or Gln
<220> FEATURE:
<221> NAME/KEY: misc_feature
<222> LOCATION: (135)..(135)
<223> OTHER INFORMATION: Xaa may be His, Ser or Arg
<220> FEATURE:
<221> NAME/KEY: misc_feature
<222> LOCATION: (136)..(136)
<223> OTHER INFORMATION: Xaa may be Asn, Ser or Thr
<220> FEATURE:
<221> NAME/KEY: misc_feature
<222> LOCATION: (197)..(197)
<223> OTHER INFORMATION: Xaa may be Asn or Gly
<220> FEATURE:
<221> NAME/KEY: misc_feature
<222> LOCATION: (198)..(198)
<223> OTHER INFORMATION: Xaa may be Ser or Thr
<220> FEATURE:
<221> NAME/KEY: misc_feature
```

```
<222> LOCATION: (240)..(240)
<223> OTHER INFORMATION: Xaa may be Ser, Gln or Lys
<220> FEATURE:
<221> NAME/KEY: misc_feature
<222> LOCATION: (241)..(241)
<223> OTHER INFORMATION: Xaa may be Ser, Thr or Tyr
<220> FEATURE:
<221> NAME/KEY: misc_feature
<222> LOCATION: (247)..(247)
<223> OTHER INFORMATION: Xaa may be Ala, Phe or Ile
<220> FEATURE:
<221> NAME/KEY: misc_feature
<222> LOCATION: (249)..(249)
<223> OTHER INFORMATION: Xaa may be Leu, Ser or Asn
<220> FEATURE:
<221> NAME/KEY: misc_feature
<222> LOCATION: (252)..(252)
<223> OTHER INFORMATION: Xaa may be Ser, Gln, or Glu
<220> FEATURE:
<221> NAME/KEY: misc_feature
<222> LOCATION: (255)..(255)
<223> OTHER INFORMATION: Xaa may be Gly, Ile or Ser
<220> FEATURE:
<221> NAME/KEY: misc_feature
<222> LOCATION: (260)..(260)
<223> OTHER INFORMATION: Xaa may be Asn, Ala or Gln
<220> FEATURE:
<221> NAME/KEY: misc_feature
<222> LOCATION: (261)..(261)
<223> OTHER INFORMATION: Xaa may be Val, Ser or Thr
<220> FEATURE:
<221> NAME/KEY: misc_feature
<222> LOCATION: (263)..(263)
<223> OTHER INFORMATION: Xaa may be Ser, Val or Asn
<220> FEATURE:
<221> NAME/KEY: misc_feature
<222> LOCATION: (285)..(285)
<223> OTHER INFORMATION: Xaa may be Leu, Ser or Val
<220> FEATURE:
<221> NAME/KEY: misc_feature
<222> LOCATION: (289)..(289)
<223> OTHER INFORMATION: Xaa may be Ala, Phe or Cys
<220> FEATURE:
<221> NAME/KEY: misc_feature
<222> LOCATION: (291)..(291)
<223> OTHER INFORMATION: Xaa may be Ile, Val or Phe
<220> FEATURE:
<221> NAME/KEY: misc_feature
<222> LOCATION: (294)..(294)
<223> OTHER INFORMATION: Xaa may be Lys or Arg
<220> FEATURE:
<221> NAME/KEY: misc_feature
<222> LOCATION: (299)..(299)
<223> OTHER INFORMATION: Xaa may be Gly, Ala or Gln
<220> FEATURE:
<221> NAME/KEY: misc_feature
<222> LOCATION: (310)..(310)
<223> OTHER INFORMATION: Xaa may be Thr, Lys or Ser
<220> FEATURE:
<221> NAME/KEY: misc_feature
<222> LOCATION: (316)..(316)
<223> OTHER INFORMATION: Xaa may be Glu, Asp or Ala
<220> FEATURE:
<221> NAME/KEY: misc_feature
<222> LOCATION: (317)..(317)
<223> OTHER INFORMATION: Xaa may be Gly, Ser or Ala
<220> FEATURE:
<221> NAME/KEY: misc_feature
<222> LOCATION: (321)..(321)
<223> OTHER INFORMATION: Xaa may be Ile, Val or Ala
<220> FEATURE:
<221> NAME/KEY: misc_feature
<222> LOCATION: (328)..(328)
<223> OTHER INFORMATION: Xaa may be Gly, Lys or Ser
<220> FEATURE:
<221> NAME/KEY: misc_feature
<222> LOCATION: (334)..(334)
<223> OTHER INFORMATION: Xaa may be Asn, Arg or Glu
<220> FEATURE:
```

```
<221> NAME/KEY: misc_feature
<222> LOCATION: (338)..(338)
<223> OTHER INFORMATION: Xaa may be Phe, Thr or Ile
<220> FEATURE:
<221> NAME/KEY: misc_feature
<222> LOCATION: (343)..(343)
<223> OTHER INFORMATION: Xaa may be Gly or Thr
<220> FEATURE:
<221> NAME/KEY: misc_feature
<222> LOCATION: (345)..(345)
<223> OTHER INFORMATION: Xaa may be Thr, Gly or Asn
<220> FEATURE:
<221> NAME/KEY: misc_feature
<222> LOCATION: (346)..(346)
<223> OTHER INFORMATION: Xaa may be Gln, Asp or Asn
<220> FEATURE:
<221> NAME/KEY: misc_feature
<222> LOCATION: (348)..(348)
<223> OTHER INFORMATION: Xaa may be Met or Ile
<220> FEATURE:
<221> NAME/KEY: misc_feature
<222> LOCATION: (349)..(349)
<223> OTHER INFORMATION: Xaa may be Arg or Val
<220> FEATURE:
<221> NAME/KEY: misc_feature
<222> LOCATION: (350)..(350)
<223> OTHER INFORMATION: Xaa may be Ser or Thr
<220> FEATURE:
<221> NAME/KEY: misc_feature
<222> LOCATION: (351)..(351)
<223> OTHER INFORMATION: Xaa may be Tyr, Val or Asn
<220> FEATURE:
<221> NAME/KEY: misc_feature
<222> LOCATION: (354)..(354)
<223> OTHER INFORMATION: Xaa may be Asp, Gln or Lys
<220> FEATURE:
<221> NAME/KEY: misc_feature
<222> LOCATION: (357)..(357)
<223> OTHER INFORMATION: Xaa may be Pro, Val or Ser
<220> FEATURE:
<221> NAME/KEY: misc_feature
<222> LOCATION: (359)..(359)
<223> OTHER INFORMATION: Xaa may be Thr, Gly or Gln
<220> FEATURE:
<221> NAME/KEY: misc_feature
<222> LOCATION: (369)..(369)
<223> OTHER INFORMATION: Xaa may be Ala, Phe or Leu
<220> FEATURE:
<221> NAME/KEY: misc_feature
<222> LOCATION: (372)..(372)
<223> OTHER INFORMATION: Xaa may be Ile, Val or Asn
<220> FEATURE:
<221> NAME/KEY: misc_feature
<222> LOCATION: (373)..(373)
<223> OTHER INFORMATION: Xaa may be Gly, Phe or Val
<220> FEATURE:
<221> NAME/KEY: misc_feature
<222> LOCATION: (375)..(375)
<223> OTHER INFORMATION: Xaa may be Pro or Ser
<220> FEATURE:
<221> NAME/KEY: misc_feature
<222> LOCATION: (376)..(376)
<223> OTHER INFORMATION: Xaa may be Thr or Gly
<220> FEATURE:
<221> NAME/KEY: misc_feature
<222> LOCATION: (384)..(384)
<223> OTHER INFORMATION: Xaa may be Ser, Glu or Gln
<220> FEATURE:
<221> NAME/KEY: misc_feature
<222> LOCATION: (391)..(391)
<223> OTHER INFORMATION: Xaa may be His, Thr or Asp
<220> FEATURE:
<221> NAME/KEY: misc_feature
<222> LOCATION: (393)..(393)
<223> OTHER INFORMATION: Xaa may be Ser, Pro or Gly
<220> FEATURE:
<221> NAME/KEY: misc_feature
<222> LOCATION: (395)..(395)
<223> OTHER INFORMATION: Xaa may be Ser, Thr or Ala
```

```
<220> FEATURE:
<221> NAME/KEY: misc_feature
<222> LOCATION: (396)..(396)
<223> OTHER INFORMATION: Xaa may be Gln, Asp or Asn
<220> FEATURE:
<221> NAME/KEY: misc_feature
<222> LOCATION: (397)..(397)
<223> OTHER INFORMATION: Xaa may be Val, Ile or Thr
<220> FEATURE:
<221> NAME/KEY: misc_feature
<222> LOCATION: (410)..(410)
<223> OTHER INFORMATION: Xaa may be Thr, Ser or Ala
<220> FEATURE:
<221> NAME/KEY: misc_feature
<222> LOCATION: (413)..(413)
<223> OTHER INFORMATION: Xaa may be Thr, Ala or Ser
<220> FEATURE:
<221> NAME/KEY: misc_feature
<222> LOCATION: (414)..(414)
<223> OTHER INFORMATION: Xaa may be His, Asn or Gln
<220> FEATURE:
<221> NAME/KEY: misc_feature
<222> LOCATION: (418)..(418)
<223> OTHER INFORMATION: Xaa may be Ser, Pro or Ala
<220> FEATURE:
<221> NAME/KEY: misc_feature
<222> LOCATION: (434)..(434)
<223> OTHER INFORMATION: Xaa may be Lys, Ala or Ser
<220> FEATURE:
<221> NAME/KEY: misc_feature
<222> LOCATION: (435)..(435)
<223> OTHER INFORMATION: Xaa may be Met, Phe or Ile
<220> FEATURE:
<221> NAME/KEY: misc_feature
<222> LOCATION: (440)..(440)
<223> OTHER INFORMATION: Xaa may be Asn or Gln
<220> FEATURE:
<221> NAME/KEY: misc_feature
<222> LOCATION: (441)..(441)
<223> OTHER INFORMATION: Xaa may be Arg or Ser
<220> FEATURE:
<221> NAME/KEY: misc_feature
<222> LOCATION: (446)..(446)
<223> OTHER INFORMATION: Xaa may be Asp or Leu
<220> FEATURE:
<221> NAME/KEY: misc_feature
<222> LOCATION: (460)..(460)
<223> OTHER INFORMATION: Xaa may be Ala, Val or Ile
<220> FEATURE:
<221> NAME/KEY: misc_feature
<222> LOCATION: (467)..(467)
<223> OTHER INFORMATION: Xaa may be Val, Met or Gln
<220> FEATURE:
<221> NAME/KEY: misc_feature
<222> LOCATION: (502)..(502)
<223> OTHER INFORMATION: Xaa may be Ala, Val or Ser
<220> FEATURE:
<221> NAME/KEY: misc_feature
<222> LOCATION: (504)..(504)
<223> OTHER INFORMATION: Xaa may be Ser, Ala or Thr
<220> FEATURE:
<221> NAME/KEY: misc_feature
<222> LOCATION: (535)..(535)
<223> OTHER INFORMATION: Xaa may be Ser, Thr or Pro

<400> SEQUENCE: 12

Met Met Met Ala Ser Lys Asp Ala Thr Xaa Ser Ala Asp Gly Ala Ser
1               5                   10                  15

Gly Ala Gly Gln Leu Val Pro Glu Val Asn Thr Ala Asp Pro Leu Pro
            20                  25                  30

Met Asp Pro Val Ala Gly Ser Ser Thr Ala Val Ala Thr Ala Gly Gln
        35                  40                  45

Val Asn Xaa Ile Asp Pro Trp Ile Ile Asn Asn Phe Val Gln Ala Pro
    50                  55                  60
```

```
Gln Gly Glu Phe Thr Ile Ser Pro Asn Asn Thr Pro Gly Asp Val Leu
 65                  70                  75                  80

Phe Asp Leu Gln Leu Gly Pro His Leu Asn Pro Phe Leu Ser His Leu
                 85                  90                  95

Ser Gln Met Tyr Asn Gly Trp Val Gly Asn Met Arg Val Arg Ile Xaa
            100                 105                 110

Leu Ala Gly Asn Ala Phe Thr Ala Gly Lys Ile Ile Val Cys Cys Val
        115                 120                 125

Pro Pro Gly Phe Xaa Ser Xaa Xaa Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Tyr His Asn Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Xaa Xaa Asp Ser Phe Val Val Ala Gly Arg Val Leu
        195                 200                 205

Thr Cys Pro Ser Pro Asp Phe Asn Phe Leu Phe Leu Val Pro Pro Thr
210                 215                 220

Val Glu Gln Lys Thr Arg Pro Phe Thr Val Pro Asn Ile Pro Leu Xaa
225                 230                 235                 240

Xaa Leu Ser Asn Ser Arg Xaa Pro Xaa Pro Ile Xaa Gly Met Xaa Leu
                245                 250                 255

Ser Pro Asp Xaa Xaa Gln Xaa Val Gln Phe Gln Asn Gly Arg Cys Thr
            260                 265                 270

Ile Asp Gly Gln Leu Leu Gly Thr Thr Pro Val Ser Xaa Ser Gln Leu
        275                 280                 285

Xaa Lys Xaa Arg Gly Xaa Ile Thr Ser Gly Xaa Arg Val Leu Asn Leu
    290                 295                 300

Thr Glu Leu Asp Gly Xaa Pro Phe Met Ala Phe Xaa Xaa Pro Ala Pro
305                 310                 315                 320

Xaa Gly Phe Pro Asp Leu Gly Xaa Cys Asp Trp His Ile Xaa Met Ser
                325                 330                 335

Lys Xaa Pro Asn Ser Ser Xaa Gln Xaa Xaa Pro Xaa Xaa Xaa Xaa Ser
            340                 345                 350

Val Xaa Thr Asn Xaa Gln Xaa Phe Val Pro His Leu Gly Ser Ile Gln
        355                 360                 365

Xaa Asp Glu Xaa Xaa Ser Xaa Xaa Gly Asp Tyr Ile Gly Thr Ile Xaa
    370                 375                 380

Trp Ile Ser Pro Pro Ser Xaa Pro Xaa Gly Xaa Xaa Xaa Asn Leu Trp
385                 390                 395                 400

Lys Ile Pro Asp Tyr Gly Ser Ser Leu Xaa Glu Ala Xaa Xaa Leu Ala
                405                 410                 415

Pro Xaa Val Tyr Pro Pro Gly Phe Gly Glu Val Leu Val Tyr Phe Met
            420                 425                 430

Ser Xaa Xaa Pro Gly Pro Asn Xaa Xaa Gly Ala Pro Asn Xaa Val Pro
        435                 440                 445

Cys Leu Leu Pro Gln Glu Tyr Ile Thr His Phe Xaa Ser Glu Gln Ala
    450                 455                 460

Pro Thr Xaa Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
```

```
                    485                 490                 495
Cys Val Pro Asn Gly Xaa Ser Xaa Gly Pro Gln Gln Leu Pro Leu Asn
                500                 505                 510

Gly Val Phe Val Phe Val Ser Trp Val Ser Arg Phe Tyr Gln Leu Lys
            515                 520                 525

Pro Val Gly Thr Ala Ser Xaa Ala Arg Gly Arg Leu Gly Val Arg Arg
        530                 535                 540

<210> SEQ ID NO 13
<211> LENGTH: 530
<212> TYPE: PRT
<213> ORGANISM: Norovirus Norwalk virus sp.

<400> SEQUENCE: 13

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65              70                  75                  80

Phe Asp Leu Ser Leu Gly Pro His Leu Asn Pro Phe Leu His Leu
                85                  90                  95

Ser Gln Met Tyr Asn Gly Trp Val Gly Asn Met Arg Val Arg Ile Met
                100                 105                 110

Leu Ala Gly Asn Ala Phe Thr Ala Gly Lys Ile Ile Val Ser Cys Ile
            115                 120                 125

Pro Pro Gly Phe Gly Ser His Asn Leu Thr Ile Ala Gln Ala Thr Leu
        130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Ile Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320
```

```
Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
            355                 360                 365

Tyr Val Gly Val Leu Ser Trp Ile Ser Pro Pro Ser His Pro Ser Gly
        370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
            435                 440                 445

Gln Ala Pro Thr Val Gly Glu Ala Ala Leu Leu His Tyr Val Asp Pro
        450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
            515                 520                 525

Arg Arg
    530

<210> SEQ ID NO 14
<211> LENGTH: 545
<212> TYPE: PRT
<213> ORGANISM: Norovirus Norwalk virus sp.

<400> SEQUENCE: 14

Met Met Met Ala Ser Lys Asp Ala Pro Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
            115                 120                 125

Pro Pro Gly Phe Thr Ser Ser Ser Leu Thr Ile Ala Gln Ala Thr Leu
        130                 135                 140

Phe Pro His Val Ile Ala Asp Val Arg Thr Leu Glu Pro Ile Glu Met
145                 150                 155                 160
```

```
Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255

Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Gly Ser Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Ile Thr His Phe Val Ser Glu Gln
450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Gly Arg Leu Gly Val Arg
    530                 535                 540

Arg
545

<210> SEQ ID NO 15
<211> LENGTH: 544
```

<212> TYPE: PRT
<213> ORGANISM: Norovirus Norwalk virus sp.

<400> SEQUENCE: 15

```
Met Met Met Ala Ser Lys Asp Ala Thr Pro Ser Ala Asp Gly Ala Thr
1               5                   10                  15

Gly Ala Gly Gln Leu Val Pro Glu Val Asn Thr Ala Asp Pro Ile Pro
            20                  25                  30

Ile Asp Pro Val Ala Gly Ser Ser Thr Ala Leu Ala Thr Ala Gly Gln
        35                  40                  45

Val Asn Leu Ile Asp Pro Trp Ile Ile Asn Asn Phe Val Gln Ala Pro
50                  55                  60

Gln Gly Glu Phe Thr Ile Ser Pro Asn Asn Thr Pro Gly Asp Val Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Val Val
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
130                 135                 140

Phe Pro His Val Ile Ala Asp Val Arg Thr Leu Asp Pro Val Glu Val
145                 150                 155                 160

Pro Leu Glu Asp Val Arg Asn Val Leu Tyr His Asn Asn Asp Thr Gln
                165                 170                 175

Pro Thr Met Arg Leu Leu Cys Met Leu Tyr Thr Pro Leu Arg Thr Gly
            180                 185                 190

Gly Ala Ser Gly Gly Thr Asp Ser Phe Val Val Ala Gly Arg Val Leu
        195                 200                 205

Thr Cys Pro Gly Pro Asp Phe Asn Phe Leu Phe Leu Val Pro Pro Thr
210                 215                 220

Val Glu Gln Lys Thr Arg Pro Phe Thr Val Pro Asn Ile Pro Leu Lys
225                 230                 235                 240

Tyr Leu Ser Asn Ser Arg Ile Pro Asn Pro Ile Glu Gly Met Ser Leu
                245                 250                 255

Ser Pro Asp Gln Thr Gln Asn Val Gln Phe Gln Asn Gly Arg Cys Thr
            260                 265                 270

Ile Asp Gly Gln Pro Leu Gly Thr Thr Pro Val Ser Val Ser Gln Leu
        275                 280                 285

Cys Lys Phe Arg Gly Arg Ile Thr Ser Gly Gln Arg Val Leu Asn Leu
290                 295                 300

Thr Glu Leu Asp Gly Ser Pro Phe Met Ala Phe Ala Ala Pro Ala Pro
305                 310                 315                 320

Ala Gly Phe Pro Asp Leu Gly Ser Cys Asp Trp His Ile Glu Met Ser
                325                 330                 335

Lys Ile Pro Asn Ser Ser Thr Gln Asn Asn Pro Ile Val Thr Asn Ser
            340                 345                 350

Val Lys Pro Asn Ser Gln Gln Phe Val Pro His Leu Ser Ser Ile Thr
        355                 360                 365

Leu Asp Glu Asn Val Ser Ser Gly Asp Tyr Ile Gly Thr Ile Gln
370                 375                 380

Trp Thr Ser Pro Pro Ser Asp Ser Gly Gly Ala Asn Thr Asn Phe Trp
385                 390                 395                 400
```

```
Lys Ile Pro Asp Tyr Gly Ser Ser Leu Ala Glu Ala Ser Gln Leu Ala
                405                 410                 415

Pro Ala Val Tyr Pro Pro Gly Phe Asn Glu Val Ile Val Tyr Phe Met
            420                 425                 430

Ala Ser Ile Pro Gly Pro Asn Gln Ser Gly Ser Pro Asn Leu Val Pro
        435                 440                 445

Cys Leu Leu Pro Gln Glu Tyr Ile Thr His Phe Ile Ser Gln Ala
    450                 455                 460

Pro Ile Gln Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
                485                 490                 495

Cys Val Pro Asn Ser Ser Thr Gly Pro Gln Gln Leu Pro Leu Asp
            500                 505                 510

Gly Val Phe Val Phe Ala Ser Trp Val Ser Arg Phe Tyr Gln Leu Lys
        515                 520                 525

Pro Val Gly Thr Ala Gly Pro Ala Arg Gly Arg Leu Gly Val Arg Arg
            530                 535                 540
```

```
<210> SEQ ID NO 16
<211> LENGTH: 544
<212> TYPE: PRT
<213> ORGANISM: Artificial Sequence
<220> FEATURE:
<223> OTHER INFORMATION: Composite GI VP1 amino acid sequence
<220> FEATURE:
<221> NAME/KEY: misc_feature
<222> LOCATION: (285)..(285)
<223> OTHER INFORMATION: Xaa may be Leu, Ser OR Val

<400> SEQUENCE: 16

Met Met Met Ala Ser Lys Asp Ala Thr Gln Ser Ala Asp Gly Ala Ser
1               5                   10                  15

Gly Ala Gly Gln Leu Val Pro Glu Val Asn Thr Ala Asp Pro Leu Pro

|   |   |   | 195 |   |   |   | 200 |   |   |   | 205 |   |   |
|---|---|---|---|---|---|---|---|---|---|---|---|---|---|

Thr Cys Pro Ser Pro Asp Phe Asn Phe Leu Phe Leu Val Pro Pro Thr
210                 215                 220

Val Glu Gln Lys Thr Arg Pro Phe Thr Val Pro Asn Ile Pro Leu Gln
225                 230                 235                 240

Thr Leu Ser Asn Ser Arg Phe Pro Ser Pro Ile Gln Gly Met Ile Leu
            245                 250                 255

Ser Pro Asp Ala Ser Gln Val Val Gln Phe Gln Asn Gly Arg Cys Thr
        260                 265                 270

Ile Asp Gly Gln Leu Leu Gly Thr Thr Pro Val Ser Xaa Ser Gln Leu
    275                 280                 285

Phe Lys Val Arg Gly Lys Ile Thr Ser Gly Ala Arg Val Leu Asn Leu
290                 295                 300

Thr Glu Leu Asp Gly Lys Pro Phe Met Ala Phe Asp Ser Pro Ala Pro
305                 310                 315                 320

Val Gly Phe Pro Asp Leu Gly Lys Cys Asp Trp His Ile Arg Met Ser
            325                 330                 335

Lys Thr Pro Asn Ser Ser Gly Gln Gly Asp Pro Met Arg Ser Val Ser
            340                 345                 350

Val Gln Thr Asn Val Gln Gly Phe Val Pro His Leu Gly Ser Ile Gln
        355                 360                 365

Phe Asp Glu Val Phe Ser Pro Thr Gly Asp Tyr Ile Gly Thr Ile Glu
    370                 375                 380

Trp Ile Ser Pro Pro Ser Thr Pro Pro Gly Thr Asp Ile Asn Leu Trp
385                 390                 395                 400

Lys Ile Pro Asp Tyr Gly Ser Ser Leu Ser Glu Ala Ala Asn Leu Ala
            405                 410                 415

Pro Pro Val Tyr Pro Pro Gly Phe Gly Glu Val Leu Val Tyr Phe Met
            420                 425                 430

Ser Ala Phe Pro Gly Pro Asn Asn Arg Gly Ala Pro Asn Asp Val Pro
            435                 440                 445

Cys Leu Leu Pro Gln Glu Tyr Ile Thr His Phe Val Ser Glu Gln Ala
450                 455                 460

Pro Thr Met Gly Glu Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
            485                 490                 495

Cys Val Pro Asn Gly Val Ser Ala Gly Pro Gln Gln Leu Pro Leu Asn
            500                 505                 510

Gly Val Phe Val Phe Val Ser Trp Val Ser Arg Phe Tyr Gln Leu Lys
        515                 520                 525

Pro Val Gly Thr Ala Ser Thr Ala Arg Gly Arg Leu Gly Val Arg Arg
        530                 535                 540

<210> SEQ ID NO 17
<211> LENGTH: 567
<212> TYPE: PRT
<213> ORGANISM: Artificial Sequence
<220> FEATURE:
<223> OTHER INFORMATION: Consensus L1 amino acid sequence
<220> FEATURE:
<221> NAME/KEY: misc_feature
<222> LOCATION: (29)..(29)
<223> OTHER INFORMATION: Xaa may be Met or Leu
<220> FEATURE:
<221> NAME/KEY: misc_feature
<222> LOCATION: (30)..(30)

```
<223> OTHER INFORMATION: Xaa may be Gln or His
<220> FEATURE:
<221> NAME/KEY: misc_feature
<222> LOCATION: (31)..(31)
<223> OTHER INFORMATION: Xaa may be Val or Ser
<220> FEATURE:
<221> NAME/KEY: misc_feature
<222> LOCATION: (32)..(32)
<223> OTHER INFORMATION: Xaa may be Thr or Ile
<220> FEATURE:
<221> NAME/KEY: misc_feature
<222> LOCATION: (33)..(33)
<223> OTHER INFORMATION: Xaa may be Phe or Leu
<220> FEATURE:
<221> NAME/KEY: misc_feature
<222> LOCATION: (34)..(34)
<223> OTHER INFORMATION: Xaa may be Ile or Val
<220> FEATURE:
<221> NAME/KEY: misc_feature
<222> LOCATION: (36)..(36)
<223> OTHER INFORMATION: Xaa may be Ile or Met
<220> FEATURE:
<221> NAME/KEY: misc_feature
<222> LOCATION: (37)..(37)
<223> OTHER INFORMATION: Xaa may be Leu or Val
<220> FEATURE:
<221> NAME/KEY: misc_feature
<222> LOCATION: (38)..(38)
<223> OTHER INFORMATION: Xaa may be Absent or His
<220> FEATURE:
<221> NAME/KEY: misc_feature
<222> LOCATION: (39)..(39)
<223> OTHER INFORMATION: Xaa may be val or Ile
<220> FEATURE:
<221> NAME/KEY: misc_feature
<222> LOCATION: (41)..(41)
<223> OTHER INFORMATION: Xaa may be Thr or Ile
<220> FEATURE:
<221> NAME/KEY: misc_feature
<222> LOCATION: (43)..(43)
<223> OTHER INFORMATION: Xaa may be Absent or Gly
<220> FEATURE:
<221> NAME/KEY: misc_feature
<222> LOCATION: (44)..(44)
<223> OTHER INFORMATION: Xaa may be Absent or His
<220> FEATURE:
<221> NAME/KEY: misc_feature
<222> LOCATION: (45)..(45)
<223> OTHER INFORMATION: Xaa may be Absent or Tyr
<220> FEATURE:
<221> NAME/KEY: misc_feature
<222> LOCATION: (46)..(46)
<223> OTHER INFORMATION: Xaa may be Absent or Ile
<220> FEATURE:
<221> NAME/KEY: misc_feature
<222> LOCATION: (47)..(47)
<223> OTHER INFORMATION: Xaa may be Absent or Ile
<220> FEATURE:
<221> NAME/KEY: misc_feature
<222> LOCATION: (48)..(48)
<223> OTHER INFORMATION: Xaa may be Absent or Leu
<220> FEATURE:
<221> NAME/KEY: misc_feature
<222> LOCATION: (49)..(49)
<223> OTHER INFORMATION: Xaa may be Tyr or Phe
<220> FEATURE:
<221> NAME/KEY: misc_feature
<222> LOCATION: (50)..(50)
<223> OTHER INFORMATION: Xaa may be Glu or Leu
<220> FEATURE:
<221> NAME/KEY: misc_feature
<222> LOCATION: (51)..(51)
<223> OTHER INFORMATION: Xaa may be Asn or Arg
<220> FEATURE:
<221> NAME/KEY: misc_feature
<222> LOCATION: (52)..(52)
<223> OTHER INFORMATION: Xaa may be Asp or Asn
<220> FEATURE:
<221> NAME/KEY: misc_feature
```

```
<222> LOCATION: (56)..(56)
<223> OTHER INFORMATION: Xaa may be Tyr or Phe
<220> FEATURE:
<221> NAME/KEY: misc_feature
<222> LOCATION: (57)..(57)
<223> OTHER INFORMATION: Xaa may be His or Pro
<220> FEATURE:
<221> NAME/KEY: misc_feature
<222> LOCATION: (60)..(60)
<223> OTHER INFORMATION: Xaa may be Phe or Leu
<220> FEATURE:
<221> NAME/KEY: misc_feature
<222> LOCATION: (63)..(63)
<223> OTHER INFORMATION: Xaa may be Ser or Ala
<220> FEATURE:
<221> NAME/KEY: misc_feature
<222> LOCATION: (70)..(70)
<223> OTHER INFORMATION: Xaa may be Ser, Ala or Asn
<220> FEATURE:
<221> NAME/KEY: misc_feature
<222> LOCATION: (84)..(84)
<223> OTHER INFORMATION: Xaa may be Ala, Ser or Asn
<220> FEATURE:
<221> NAME/KEY: misc_feature
<222> LOCATION: (87)..(87)
<223> OTHER INFORMATION: Xaa may be Ala, Glu or Asp
<220> FEATURE:
<221> NAME/KEY: misc_feature
<222> LOCATION: (90)..(90)
<223> OTHER INFORMATION: Xaa may be Lys, Ala or Thr
<220> FEATURE:
<221> NAME/KEY: misc_feature
<222> LOCATION: (112)..(112)
<223> OTHER INFORMATION: Xaa may be Ser, Pro or Arg
<220> FEATURE:
<221> NAME/KEY: misc_feature
<222> LOCATION: (116)..(116)
<223> OTHER INFORMATION: Xaa may be Pro or Gly
<220> FEATURE:
<221> NAME/KEY: misc_feature
<222> LOCATION: (117)..(117)
<223> OTHER INFORMATION: Xaa may be Asn or Gly
<220> FEATURE:
<221> NAME/KEY: misc_feature
<222> LOCATION: (118)..(118)
<223> OTHER INFORMATION: Xaa may be Val or Asn
<220> FEATURE:
<221> NAME/KEY: misc_feature
<222> LOCATION: (121)..(121)
<223> OTHER INFORMATION: Xaa may be Thr, Ile or Gln
<220> FEATURE:
<221> NAME/KEY: misc_feature
<222> LOCATION: (122)..(122)
<223> OTHER INFORMATION: Xaa may be Val, Leu or Asp
<220> FEATURE:
<221> NAME/KEY: misc_feature
<222> LOCATION: (137)..(137)
<223> OTHER INFORMATION: Xaa may be Val, His or Gln
<220> FEATURE:
<221> NAME/KEY: misc_feature
<222> LOCATION: (151)..(151)
<223> OTHER INFORMATION: Xaa may be Leu, Phe or Ile
<220> FEATURE:
<221> NAME/KEY: misc_feature
<222> LOCATION: (155)..(155)
<223> OTHER INFORMATION: Xaa may be Thr, Asp or Glu
<220> FEATURE:
<221> NAME/KEY: misc_feature
<222> LOCATION: (164)..(164)
<223> OTHER INFORMATION: Xaa may be Thr, Val or Ala
<220> FEATURE:
<221> NAME/KEY: misc_feature
<222> LOCATION: (178)..(178)
<223> OTHER INFORMATION: Xaa may be Val, Ile or Leu
<220> FEATURE:
<221> NAME/KEY: misc_feature
<222> LOCATION: (194)..(194)
<223> OTHER INFORMATION: Xaa may be Gly, Ser or His
<220> FEATURE:
```

```
<221> NAME/KEY: misc_feature
<222> LOCATION: (197)..(197)
<223> OTHER INFORMATION: Xaa may be Gly, Ala or Thr
<220> FEATURE:
<221> NAME/KEY: misc_feature
<222> LOCATION: (198)..(198)
<223> OTHER INFORMATION: Xaa may be Gly, Ala or Ser
<220> FEATURE:
<221> NAME/KEY: misc_feature
<222> LOCATION: (200)..(200)
<223> OTHER INFORMATION: Xaa may be Pro, Ala or Val
<220> FEATURE:
<221> NAME/KEY: misc_feature
<222> LOCATION: (202)..(202)
<223> OTHER INFORMATION: Xaa may be Gln, Val or Glu
<220> FEATURE:
<221> NAME/KEY: misc_feature
<222> LOCATION: (206)..(206)
<223> OTHER INFORMATION: Xaa may be Val, Glu or Asp
<220> FEATURE:
<221> NAME/KEY: misc_feature
<222> LOCATION: (219)..(219)
<223> OTHER INFORMATION: Xaa may be Met, Leu or Ile
<220> FEATURE:
<221> NAME/KEY: misc_feature
<222> LOCATION: (220)..(220)
<223> OTHER INFORMATION: Xaa may be Val, Ile or Leu
<220> FEATURE:
<221> NAME/KEY: misc_feature
<222> LOCATION: (235)..(235)
<223> OTHER INFORMATION: Xaa may be Gln, Pro or Ala
<220> FEATURE:
<221> NAME/KEY: misc_feature
<222> LOCATION: (237)..(237)
<223> OTHER INFORMATION: Xaa may be Ser, Thr or Ala
<220> FEATURE:
<221> NAME/KEY: misc_feature
<222> LOCATION: (239)..(239)
<223> OTHER INFORMATION: Xaa may be Thr, Val or Arg
<220> FEATURE:
<221> NAME/KEY: misc_feature
<222> LOCATION: (240)..(240)
<223> OTHER INFORMATION: Xaa may be Ser, Ala or Pro
<220> FEATURE:
<221> NAME/KEY: misc_feature
<222> LOCATION: (242)..(242)
<223> OTHER INFORMATION: Xaa may be Gln, Asn or Ser
<220> FEATURE:
<221> NAME/KEY: misc_feature
<222> LOCATION: (243)..(243)
<223> OTHER INFORMATION: Xaa may be Asn, Pro or Gln
<220> FEATURE:
<221> NAME/KEY: misc_feature
<222> LOCATION: (272)..(272)
<223> OTHER INFORMATION: Xaa may be Ala, Thr or Ser
<220> FEATURE:
<221> NAME/KEY: misc_feature
<222> LOCATION: (276)..(276)
<223> OTHER INFORMATION: Xaa may be Thr, Ala or Asp
<220> FEATURE:
<221> NAME/KEY: misc_feature
<222> LOCATION: (287)..(287)
<223> OTHER INFORMATION: Xaa may be Gly, Thr or Gln
<220> FEATURE:
<221> NAME/KEY: misc_feature
<222> LOCATION: (299)..(299)
<223> OTHER INFORMATION: Xaa may be Ala, Val or Ser
<220> FEATURE:
<221> NAME/KEY: misc_feature
<222> LOCATION: (331)..(331)
<223> OTHER INFORMATION: Xaa may be Pro, Asn or Thr
<220> FEATURE:
<221> NAME/KEY: misc_feature
<222> LOCATION: (341)..(341)
<223> OTHER INFORMATION: Xaa may be Gly, Ser or Thr
<220> FEATURE:
<221> NAME/KEY: misc_feature
<222> LOCATION: (343)..(343)
<223> OTHER INFORMATION: Xaa may be Asn, Ser or Met
```

```
<220> FEATURE:
<221> NAME/KEY: misc_feature
<222> LOCATION: (344)..(344)
<223> OTHER INFORMATION: Xaa may be Arg, Thr or Pro
<220> FEATURE:
<221> NAME/KEY: misc_feature
<222> LOCATION: (347)..(347)
<223> OTHER INFORMATION: Xaa may be Val, Leu or Pro
<220> FEATURE:
<221> NAME/KEY: misc_feature
<222> LOCATION: (351)..(351)
<223> OTHER INFORMATION: Xaa may be Ile, Asn or Val
<220> FEATURE:
<221> NAME/KEY: misc_feature
<222> LOCATION: (353)..(353)
<223> OTHER INFORMATION: Xaa may be Val, Phe or Ser
<220> FEATURE:
<221> NAME/KEY: misc_feature
<222> LOCATION: (360)..(360)
<223> OTHER INFORMATION: Xaa may be Leu, Met and Ile
<220> FEATURE:
<221> NAME/KEY: misc_feature
<222> LOCATION: (409)..(409)
<223> OTHER INFORMATION: Xaa may be Val, Ile or Gln
<220> FEATURE:
<221> NAME/KEY: misc_feature
<222> LOCATION: (411)..(411)
<223> OTHER INFORMATION: Xaa may be Lys, Thr or Pro
<220> FEATURE:
<221> NAME/KEY: misc_feature
<222> LOCATION: (413)..(413)
<223> OTHER INFORMATION: Xaa may be Ala, Glu or Pro
<220> FEATURE:
<221> NAME/KEY: misc_feature
<222> LOCATION: (414)..(414)
<223> OTHER INFORMATION: Xaa may be Thr or Gly
<220> FEATURE:
<221> NAME/KEY: misc_feature
<222> LOCATION: (417)..(417)
<223> OTHER INFORMATION: Xaa may be Thr or Lys
<220> FEATURE:
<221> NAME/KEY: misc_feature
<222> LOCATION: (420)..(420)
<223> OTHER INFORMATION: Xaa may be Asp, Asn or Lys
<220> FEATURE:
<221> NAME/KEY: misc_feature
<222> LOCATION: (425)..(425)
<223> OTHER INFORMATION: Xaa may be Met, Leu or Ser
<220> FEATURE:
<221> NAME/KEY: misc_feature
<222> LOCATION: (441)..(441)
<223> OTHER INFORMATION: Xaa may be Ser, Lys or Thr
<220> FEATURE:
<221> NAME/KEY: misc_feature
<222> LOCATION: (450)..(450)
<223> OTHER INFORMATION: Xaa may be Ala, Thr or Ser
<220> FEATURE:
<221> NAME/KEY: misc_feature
<222> LOCATION: (468)..(468)
<223> OTHER INFORMATION: Xaa may be Ser, Gln or Pro
<220> FEATURE:
<221> NAME/KEY: misc_feature
<222> LOCATION: (472)..(472)
<223> OTHER INFORMATION: Xaa may be Asn, Gly or Thr
<220> FEATURE:
<221> NAME/KEY: misc_feature
<222> LOCATION: (492)..(492)
<223> OTHER INFORMATION: Xaa may be Pro, His or Asp
<220> FEATURE:
<221> NAME/KEY: misc_feature
<222> LOCATION: (499)..(499)
<223> OTHER INFORMATION: Xaa may be Gln, Glu or Lys
<220> FEATURE:
<221> NAME/KEY: misc_feature
<222> LOCATION: (505)..(505)
<223> OTHER INFORMATION: Xaa may be Met, Tyr or Leu
<220> FEATURE:
<221> NAME/KEY: misc_feature
<222> LOCATION: (506)..(506)
```

```
<223> OTHER INFORMATION: Xaa may be Ser, Thr or Lys
<220> FEATURE:
<221> NAME/KEY: misc_feature
<222> LOCATION: (518)..(518)
<223> OTHER INFORMATION: Xaa may be Ser, Ala or Leu
<220> FEATURE:
<221> NAME/KEY: misc_feature
<222> LOCATION: (537)..(537)
<223> OTHER INFORMATION: Xaa may be Gly, Ala or Arg
<220> FEATURE:
<221> NAME/KEY: misc_feature
<222> LOCATION: (540)..(540)
<223> OTHER INFORMATION: Xaa may be Ser, Lys or Thr
<220> FEATURE:
<221> NAME/KEY: misc_feature
<222> LOCATION: (541)..(541)
<223> OTHER INFORMATION: Xaa may be Ala, Phe or Ile
<220> FEATURE:
<221> NAME/KEY: misc_feature
<222> LOCATION: (542)..(542)
<223> OTHER INFORMATION: Xaa may be absent, Arg or Thr
<220> FEATURE:
<221> NAME/KEY: misc_feature
<222> LOCATION: (543)..(543)
<223> OTHER INFORMATION: Xaa may be Thr, Leu or Gly
<220> FEATURE:
<221> NAME/KEY: misc_feature
<222> LOCATION: (545)..(545)
<223> OTHER INFORMATION: Xaa may be Ile, Lys or Arg
<220> FEATURE:
<221> NAME/KEY: misc_feature
<222> LOCATION: (548)..(548)
<223> OTHER INFORMATION: Xaa may be Ala or Ser
<220> FEATURE:
<221> NAME/KEY: misc_feature
<222> LOCATION: (549)..(549)
<223> OTHER INFORMATION: Xaa may be Thr or Ala
<220> FEATURE:
<221> NAME/KEY: misc_feature
<222> LOCATION: (551)..(551)
<223> OTHER INFORMATION: Xaa may be Ala, Thr or Ser
<220> FEATURE:
<221> NAME/KEY: misc_feature
<222> LOCATION: (552)..(552)
<223> OTHER INFORMATION: Xaa may be Val, Thr or Ala
<220> FEATURE:
<221> NAME/KEY: misc_feature
<222> LOCATION: (554)..(554)
<223> OTHER INFORMATION: Xaa may be Lys, Ser or Thr
<220> FEATURE:
<221> NAME/KEY: misc_feature
<222> LOCATION: (555)..(555)
<223> OTHER INFORMATION: Xaa may be Pro, Thr or Ser
<220> FEATURE:
<221> NAME/KEY: misc_feature
<222> LOCATION: (558)..(558)
<223> OTHER INFORMATION: Xaa may be Ala, Thr or Pro
<220> FEATURE:
<221> NAME/KEY: misc_feature
<222> LOCATION: (564)..(564)
<223> OTHER INFORMATION: Xaa may be Thr, Arg or Val
<220> FEATURE:
<221> NAME/KEY: misc_feature
<222> LOCATION: (566)..(566)
<223> OTHER INFORMATION: Xaa may be Thr, Leu or Ala
<220> FEATURE:
<221> NAME/KEY: misc_feature
<222> LOCATION: (567)..(567)
<223> OTHER INFORMATION: Xaa may be Lys or Arg

<400> SEQUENCE: 17

Met Cys Leu Tyr Thr Arg Val Leu Ile Leu His Tyr His Leu Leu Pro
 1               5                  10                  15

Leu Tyr Gly Pro Leu Tyr His Pro Arg Pro Leu Pro Xaa Xaa Xaa Xaa
            20                  25                  30

Xaa Xaa Tyr Xaa Xaa Xaa Xaa Ile Xaa Cys Xaa Xaa Xaa Xaa Xaa Xaa
```

```
            35                  40                  45
Xaa Xaa Xaa Xaa Val Asn Val Xaa Xaa Ile Phe Xaa Gln Met Xaa Leu
 50                  55                  60

Trp Arg Pro Ser Asp Xaa Thr Val Tyr Leu Pro Pro Pro Val Ser
 65                  70                  75                  80

Lys Val Val Xaa Thr Asp Xaa Tyr Val Xaa Arg Thr Asn Ile Phe Tyr
                 85                  90                  95

His Ala Gly Ser Ser Arg Leu Leu Ala Val Gly His Pro Tyr Phe Xaa
                100                 105                 110

Ile Lys Lys Xaa Xaa Xaa Asn Lys Xaa Xaa Val Pro Lys Val Ser Gly
                115                 120                 125

Tyr Gln Tyr Arg Val Phe Arg Val Xaa Leu Pro Asp Pro Asn Lys Phe
130                 135                 140

Gly Leu Pro Asp Thr Ser Xaa Tyr Asn Pro Xaa Thr Gln Arg Leu Val
145                 150                 155                 160

Trp Ala Cys Xaa Gly Val Glu Val Gly Arg Gly Gln Pro Leu Gly Val
                165                 170                 175

Gly Xaa Ser Gly His Pro Leu Leu Asn Lys Leu Asp Asp Thr Glu Asn
                180                 185                 190

Ser Xaa Ala Tyr Xaa Xaa Asn Xaa Gly Xaa Asp Asn Arg Xaa Asn Val
                195                 200                 205

Ser Met Asp Tyr Lys Gln Thr Gln Leu Cys Xaa Xaa Gly Cys Ala Pro
210                 215                 220

Pro Ile Gly Glu His Trp Gly Lys Gly Thr Xaa Cys Xaa Asn Xaa Xaa
225                 230                 235                 240

Val Xaa Xaa Gly Asp Cys Pro Pro Leu Glu Leu Ile Asn Thr Val Ile
                245                 250                 255

Gln Asp Gly Asp Met Val Asp Thr Gly Phe Gly Ala Met Asp Phe Xaa
                260                 265                 270

Thr Leu Gln Xaa Asn Lys Ser Glu Val Pro Leu Asp Ile Cys Xaa Ser
                275                 280                 285

Ile Cys Lys Tyr Pro Asp Tyr Leu Gln Met Xaa Ala Asp Pro Tyr Gly
290                 295                 300

Asp Ser Leu Phe Phe Tyr Leu Arg Arg Glu Gln Met Phe Ala Arg His
305                 310                 315                 320

Phe Phe Asn Arg Ala Gly Thr Val Gly Glu Xaa Val Pro Asp Asp Leu
                325                 330                 335

Tyr Ile Lys Gly Xaa Gly Xaa Xaa Ala Ser Xaa Ala Ser Ser Xaa Tyr
                340                 345                 350

Xaa Pro Thr Pro Ser Gly Ser Xaa Val Thr Ser Asp Ala Gln Leu Phe
                355                 360                 365

Asn Lys Pro Tyr Trp Leu Gln Lys Ala Gln Gly His Asn Asn Gly Ile
                370                 375                 380

Cys Trp Gly Asn Gln Leu Phe Val Thr Val Val Asp Thr Thr Arg Ser
385                 390                 395                 400

Thr Asn Met Thr Leu Cys Ala Ser Xaa Ser Xaa Ser Xaa Xaa Thr Tyr
                405                 410                 415

Xaa Asn Thr Xaa Phe Lys Glu Tyr Xaa Arg His Val Glu Glu Tyr Asp
                420                 425                 430

Leu Gln Phe Ile Phe Gln Leu Cys Xaa Ile Thr Leu Thr Ala Asp Val
                435                 440                 445

Met Xaa Tyr Ile His Ser Met Asn Ser Ser Ile Leu Glu Asp Trp Asn
                450                 455                 460
```

-continued

Phe Gly Leu Xaa Pro Pro Xaa Gly Thr Leu Glu Asp Thr Tyr Arg
465                 470             475                 480

Phe Val Gln Ser Gln Ala Ile Thr Cys Gln Lys Xaa Thr Pro Pro Ala
            485                 490             495

Glu Lys Xaa Asp Pro Tyr Lys Lys Xaa Xaa Phe Trp Glu Val Asn Leu
        500             505                 510

Lys Glu Lys Phe Ser Xaa Asp Leu Asp Gln Phe Pro Leu Gly Arg Lys
            515             520                 525

Phe Leu Leu Gln Ala Gly Leu Arg Xaa Lys Pro Xaa Xaa Xaa Xaa Gly
        530             535             540

Xaa Lys Arg Xaa Xaa Pro Xaa Xaa Ser Xaa Xaa Ser Thr Xaa Ala Lys
545             550             555                 560

Arg Lys Arg Xaa Lys Xaa Xaa
            565

<210> SEQ ID NO 18
<211> LENGTH: 500
<212> TYPE: PRT
<213> ORGANISM: Human papillomavirus type 11

<400> SEQUENCE: 18

Met Trp Arg Pro Ser Asp Ser Thr Val Tyr Val Pro Pro Asn Pro
1               5                   10                  15

Val Ser Lys Val Val Ala Thr Asp Ala Tyr Val Lys Arg Thr Asn Ile
            20                  25                  30

Phe Tyr His Ala Ser Ser Ser Arg Leu Leu Ala Val Gly His Pro Tyr
        35                  40                  45

Tyr Ser Ile Lys Lys Val Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Leu Leu Asn Lys Tyr Asp Asp Val Glu Asn
        115                 120                 125

Ser Gly Gly Tyr Gly Gly Asn Pro Gly Gln Asp Asn Arg Val Asn Val
    130                 135                 140

Gly Met Asp Tyr Lys Gln Thr Gln Leu Cys Met Val Gly Cys Ala Pro
145                 150                 155                 160

Pro Leu Gly Glu His Trp Gly Lys Gly Thr Gln Cys Ser Asn Thr Ser
                165                 170                 175

Val Gln Asn Gly Asp Cys Pro Pro Leu Glu Leu Ile Thr Ser Val Ile
            180                 185                 190

Gln Asp Gly Asp Met Val Asp Thr Gly Phe Gly Ala Met Asn Phe Ala
        195                 200                 205

Asp Leu Gln Thr Asn Lys Ser Asp Val Pro Leu Asp Ile Cys Gly Thr
    210                 215                 220

Val Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
                245                 250                 255

Phe Phe Asn Arg Ala Gly Thr Val Gly Glu Pro Val Pro Asp Asp Leu

```
            260                 265                 270
Leu Val Lys Gly Gly Asn Asn Arg Ser Ser Val Ala Ser Ser Ile Tyr
            275                 280                 285

Val His Thr Pro Ser Gly Ser Leu Val Ser Ser Glu Ala Gln Leu Phe
            290                 295                 300

Asn Lys Pro Tyr Trp Leu Gln Lys Ala Gln Gly His Asn Asn Gly Ile
305                 310                 315                 320

Cys Trp Gly Asn His Leu Phe Val Thr Val Asp Thr Thr Arg Ser
                325                 330                 335

Thr Asn Met Thr Leu Cys Ala Ser Val Ser Lys Ser Ala Thr Tyr Thr
                340                 345                 350

Asn Ser Asp Tyr Lys Glu Tyr Met Arg His Val Glu Glu Phe Asp Leu
            355                 360                 365

Gln Phe Ile Phe Gln Leu Cys Ser Ile Thr Leu Ser Ala Glu Val Met
            370                 375                 380

Ala Tyr Ile His Thr Met Asn Pro Ser Val Leu Glu Asp Trp Asn Phe
385                 390                 395                 400

Gly Leu Ser Pro Pro Asn Gly Thr Leu Glu Asp Thr Tyr Arg Tyr
                405                 410                 415

Val Gln Ser Gln Ala Ile Thr Cys Gln Lys Pro Thr Pro Glu Lys Glu
            420                 425                 430

Lys Gln Asp Pro Tyr Lys Asp Met Ser Phe Trp Glu Val Asn Leu Lys
            435                 440                 445

Glu Lys Phe Ser Ser Glu Leu Asp Gln Phe Pro Leu Gly Arg Lys Phe
450                 455                 460

Leu Leu Gln Ser Gly Tyr Arg Gly Arg Thr Ser Ala Arg Thr Gly Ile
465                 470                 475                 480

Lys Arg Pro Ala Val Ser Lys Pro Ser Thr Ala Pro Lys Arg Lys Arg
                485                 490                 495

Thr Lys Thr Lys
            500

<210> SEQ ID NO 19
<211> LENGTH: 531
<212> TYPE: PRT
<213> ORGANISM: Human papillomavirus type 16

<400> SEQUENCE: 19

Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
                20                  25                  30

Ser Glu Ala Thr Val Tyr Leu Pro Pro Val Pro Val Ser Lys Val Val
            35                  40                  45

Ser Thr Asp Glu Tyr Val Ala Arg Thr Asn Ile Tyr Tyr His Ala Gly
        50                  55                  60

Thr Ser Arg Leu Leu Ala Val Gly His Pro Tyr Phe Pro Ile Lys Lys
65                  70                  75                  80

Pro Asn Asn Asn Lys Ile Leu Val Pro Lys Val Ser Gly Leu Gln Tyr
                85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
        115                 120                 125
```

-continued

```
Val Gly Val Glu Val Gly Arg Gly Gln Pro Leu Gly Val Gly Ile Ser
    130                 135                 140
Gly His Pro Leu Leu Asn Lys Leu Asp Asp Thr Glu Asn Ala Ser Ala
145                 150                 155                 160
Tyr Ala Ala Asn Ala Gly Val Asp Asn Arg Glu Cys Ile Ser Met Asp
                165                 170                 175
Tyr Lys Gln Thr Gln Leu Cys Leu Ile Gly Cys Lys Pro Pro Ile Gly
                180                 185                 190
Glu His Trp Gly Lys Gly Ser Pro Cys Thr Asn Val Ala Val Asn Pro
            195                 200                 205
Gly Asp Cys Pro Pro Leu Glu Leu Ile Asn Thr Val Ile Gln Asp Gly
210                 215                 220
Asp Met Val Asp Thr Gly Phe Gly Ala Met Asp Phe Thr Thr Leu Gln
225                 230                 235                 240
Ala Asn Lys Ser Glu Val Pro Leu Asp Ile Cys Thr Ser Ile Cys Lys
                245                 250                 255
Tyr Pro Asp Tyr Ile Lys Met Val Ser Glu Pro Tyr Gly Asp Ser Leu
                260                 265                 270
Phe Phe Tyr Leu Arg Arg Glu Gln Met Phe Val Arg His Leu Phe Asn
            275                 280                 285
Arg Ala Gly Ala Val Gly Glu Asn Val Pro Asp Asp Leu Tyr Ile Lys
290                 295                 300
Gly Ser Gly Ser Thr Ala Asn Leu Ala Ser Ser Asn Tyr Phe Pro Thr
305                 310                 315                 320
Pro Ser Gly Ser Met Val Thr Ser Asp Ala Gln Ile Phe Asn Lys Pro
                325                 330                 335
Tyr Trp Leu Gln Arg Ala Gln Gly His Asn Asn Gly Ile Cys Trp Gly
                340                 345                 350
Asn Gln Leu Phe Val Thr Val Asp Thr Thr Arg Ser Thr Asn Met
            355                 360                 365
Ser Leu Cys Ala Ala Ile Ser Thr Ser Glu Thr Thr Tyr Lys Asn Thr
370                 375                 380
Asn Phe Lys Glu Tyr Leu Arg His Gly Glu Glu Tyr Asp Leu Gln Phe
385                 390                 395                 400
Ile Phe Gln Leu Cys Lys Ile Thr Leu Thr Ala Asp Val Met Thr Tyr
                405                 410                 415
Ile His Ser Met Asn Ser Thr Ile Leu Glu Asp Trp Asn Phe Gly Leu
                420                 425                 430
Gln Pro Pro Pro Gly Gly Thr Leu Glu Asp Thr Tyr Arg Phe Val Thr
            435                 440                 445
Ser Gln Ala Ile Ala Cys Gln Lys His Thr Pro Pro Ala Pro Lys Glu
450                 455                 460
Asp Pro Leu Lys Lys Tyr Thr Phe Trp Glu Val Asn Leu Lys Glu Lys
465                 470                 475                 480
Phe Ser Ala Asp Leu Asp Gln Phe Pro Leu Gly Arg Lys Phe Leu Leu
                485                 490                 495
Gln Ala Gly Leu Lys Ala Lys Pro Lys Phe Thr Leu Gly Lys Arg Lys
                500                 505                 510
Ala Thr Pro Thr Thr Ser Ser Thr Ser Thr Thr Ala Lys Arg Lys Lys
            515                 520                 525
Arg Lys Leu
    530
```

<210> SEQ ID NO 20
<211> LENGTH: 567
<212> TYPE: PRT
<213> ORGANISM: Human papillomavirus type 18

<400> SEQUENCE: 20

```
Met Cys Leu Tyr Thr Arg Val Leu Ile Leu His Tyr His Leu Leu Pro
1               5                   10                  15

Leu Tyr Gly Pro Leu Tyr His Pro Arg Pro Leu Pro Leu His Ser Ile
            20                  25                  30

Leu Val Tyr Met Val His Ile Ile Cys Gly His Tyr Ile Ile Leu
        35                  40                  45

Phe Leu Arg Asn Val Asn Val Phe Pro Ile Phe Leu Gln Met Ala Leu
50                  55                  60

Trp Arg Pro Ser Asp Asn Thr Val Tyr Leu Pro Pro Pro Ser Val Ala
65                  70                  75                  80

Arg Val Val Asn Thr Asp Asp Tyr Val Thr Pro Thr Ser Ile Phe Tyr
                85                  90                  95

His Ala Gly Ser Ser Arg Leu Leu Thr Val Gly Asn Pro Tyr Phe Arg
            100                 105                 110

Val Pro Ala Gly Gly Gly Asn Lys Gln Asp Ile Pro Lys Val Ser Ala
        115                 120                 125

Tyr Gln Tyr Arg Val Phe Arg Val Gln Leu Pro Asp Pro Asn Lys Phe
130                 135                 140

Gly Leu Pro Asp Thr Ser Ile Tyr Asn Pro Glu Thr Gln Arg Leu Val
145                 150                 155                 160

Trp Ala Cys Ala Gly Val Glu Ile Gly Arg Gly Gln Pro Leu Gly Val
                165                 170                 175

Gly Leu Ser Gly His Pro Phe Tyr Asn Lys Leu Asp Asp Thr Glu Ser
            180                 185                 190

Ser His Ala Ala Thr Ser Asn Val Ser Glu Asp Val Arg Asp Asn Val
        195                 200                 205

Ser Val Asp Tyr Lys Gln Thr Gln Leu Cys Ile Leu Gly Cys Ala Pro
210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
            260                 265                 270

Thr Leu Gln Asp Thr Lys Cys Glu Val Pro Leu Asp Ile Cys Gln Ser
        275                 280                 285

Ile Cys Lys Tyr Pro Asp Tyr Leu Gln Met Ser Ala Asp Pro Tyr Gly
290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335

Tyr Ile Lys Gly Thr Gly Met Pro Ala Ser Pro Gly Ser Cys Val Tyr
            340                 345                 350

Ser Pro Ser Pro Ser Gly Ser Ile Val Thr Ser Asp Ser Gln Leu Phe
        355                 360                 365

Asn Lys Pro Tyr Trp Leu His Lys Ala Gln Gly His Asn Asn Gly Val
370                 375                 380
```

-continued

```
Cys Trp His Asn Gln Leu Phe Val Thr Val Val Asp Thr Thr Pro Ser
385                 390                 395                 400

Thr Asn Leu Thr Ile Cys Ala Ser Thr Gln Ser Pro Val Pro Gly Gln
                405                 410                 415

Tyr Asp Ala Thr Lys Phe Lys Gln Tyr Ser Arg His Val Glu Glu Tyr
            420                 425                 430

Asp Leu Gln Phe Ile Phe Gln Leu Cys Thr Ile Thr Leu Thr Ala Asp
            435                 440                 445

Val Met Ser Tyr Ile His Ser Met Asn Ser Ser Ile Leu Glu Asp Trp
        450                 455                 460

Asn Phe Gly Val Pro Pro Pro Thr Thr Ser Leu Val Asp Thr Tyr
465                 470                 475                 480

Arg Phe Val Gln Ser Val Ala Ile Thr Cys Gln Lys Asp Ala Ala Pro
                485                 490                 495

Ala Glu Asn Lys Asp Pro Tyr Asp Lys Leu Lys Phe Trp Asn Val Asp
            500                 505                 510

Leu Lys Glu Lys Phe Ser Leu Asp Leu Asp Gln Tyr Pro Leu Gly Arg
        515                 520                 525

Lys Phe Leu Val Gln Ala Gly Leu Arg Arg Lys Pro Thr Ile Gly Pro
530                 535                 540

Arg Lys Arg Ser Ala Pro Ser Ala Thr Thr Ser Ser Lys Pro Ala Lys
545                 550                 555                 560

Arg Val Arg Val Arg Ala Arg
                565

<210> SEQ ID NO 21
<211> LENGTH: 566
<212> TYPE: PRT
<213> ORGANISM: Artificial Sequence
<220> FEATURE:
<223> OTHER INFORMATION: Consensus L1 capsid amino acid sequence

<400> SEQUENCE: 21

Met Cys Leu Tyr Thr Arg Val Leu Ile Leu His Tyr His Leu Leu Pro
1               5                   10                  15

Leu Tyr Gly Pro Leu Tyr His Pro Arg Pro Leu Pro Leu His Ser Ile
            20                  25                  30

Leu Val Tyr Met Val His Ile Ile Ile Cys Gly His Tyr Ile Ile Leu
        35                  40                  45

Phe Leu Arg Asn Val Asn Val Phe Pro Ile Phe Leu Gln Met Ala Leu
    50                  55                  60

Trp Arg Pro Ser Asp Asn Thr Val Tyr Leu Pro Pro Pro Val Ser
65                  70                  75                  80

Lys Val Val Asn Thr Asp Asp Tyr Val Thr Arg Thr Asn Ile Phe Tyr
                85                  90                  95

His Ala Gly Ser Ser Arg Leu Leu Ala Val Gly His Pro Tyr Phe Arg
            100                 105                 110

Ile Lys Lys Gly Gly Gly Asn Lys Gln Asp Val Pro Lys Val Ser Gly
        115                 120                 125

Tyr Gln Tyr Arg Val Phe Arg Val Gln Leu Pro Asp Pro Asn Lys Phe
    130                 135                 140

Gly Leu Pro Asp Thr Ser Ile Tyr Asn Pro Glu Thr Gln Arg Leu Val
145                 150                 155                 160

Trp Ala Cys Ala Gly Val Glu Val Gly Arg Gly Gln Pro Leu Gly Val
                165                 170                 175
```

```
Gly Leu Ser Gly His Pro Leu Leu Asn Lys Leu Asp Asp Thr Glu Asn
                180                 185                 190
Ser His Ala Tyr Thr Ser Asn Val Gly Glu Asp Asn Arg Asp Asn Val
            195                 200                 205
Ser Met Asp Tyr Lys Gln Thr Gln Leu Cys Ile Leu Gly Cys Ala Pro
        210                 215                 220
Pro Ile Gly Glu His Trp Gly Lys Gly Thr Ala Cys Lys Asn Arg Pro
225                 230                 235                 240
Val Ser Gln Gly Asp Cys Pro Leu Glu Leu Ile Asn Thr Val Ile
                245                 250                 255
Gln Asp Gly Asp Met Val Asp Thr Gly Phe Gly Ala Met Asp Phe Ser
            260                 265                 270
Thr Leu Gln Asp Asn Lys Ser Glu Val Pro Leu Asp Ile Cys Gln Ser
        275                 280                 285
Ile Cys Lys Tyr Pro Asp Tyr Leu Gln Met Ser Ala Asp Pro Tyr Gly
    290                 295                 300
Asp Ser Leu Phe Phe Tyr Leu Arg Arg Glu Gln Met Phe Ala Arg His
305                 310                 315                 320
Phe Phe Asn Arg Ala Gly Thr Val Gly Glu Thr Val Pro Asp Asp Leu
                325                 330                 335
Tyr Ile Lys Gly Thr Gly Met Pro Ala Ser Pro Ala Ser Ser Val Tyr
            340                 345                 350
Ser Pro Thr Pro Ser Gly Ser Ile Val Thr Ser Asp Ala Gln Leu Phe
        355                 360                 365
Asn Lys Pro Tyr Trp Leu Gln Lys Ala Gln His Asn Asn Gly Ile
    370                 375                 380
Cys Trp Gly Asn Gln Leu Phe Val Thr Val Val Asp Thr Thr Arg Ser
385                 390                 395                 400
Thr Asn Met Thr Leu Cys Ala Ser Gln Ser Pro Ser Pro Gly Thr Tyr
                405                 410                 415
Asp Asn Thr Lys Phe Lys Glu Tyr Ser Arg His Val Glu Glu Tyr Asp
            420                 425                 430
Leu Gln Phe Ile Phe Gln Leu Cys Thr Ile Thr Leu Thr Ala Asp Val
        435                 440                 445
Met Ser Tyr Ile His Ser Met Asn Ser Ser Ile Leu Glu Asp Trp Asn
    450                 455                 460
Phe Gly Leu Pro Pro Pro Thr Gly Thr Leu Glu Asp Thr Tyr Arg
465                 470                 475                 480
Phe Val Gln Ser Gln Ala Ile Thr Cys Gln Lys Asp Thr Pro Ala
                485                 490                 495
Glu Lys Lys Asp Pro Tyr Lys Lys Leu Lys Phe Trp Glu Val Asn Leu
            500                 505                 510
Lys Glu Lys Phe Ser Leu Asp Leu Asp Gln Phe Pro Leu Gly Arg Lys
        515                 520                 525
Phe Leu Leu Gln Ala Gly Leu Arg Arg Lys Pro Thr Ile Gly Gly Arg
    530                 535                 540
Lys Arg Ser Ala Pro Ser Ala Ser Thr Ser Ser Thr Pro Ala Lys Arg
545                 550                 555                 560
Lys Arg Val Lys Ala Arg
                565

<210> SEQ ID NO 22
<211> LENGTH: 540
<212> TYPE: PRT
```

<213> ORGANISM: Artificial Sequence
<220> FEATURE:
<223> OTHER INFORMATION: Composite GII.4 Norovirus VP1 amino acid sequence

<400> SEQUENCE: 22

```
Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Lys Phe Thr
    370                 375                 380
```

```
Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
            405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
            485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540
```